(12) United States Patent
McBride et al.

(10) Patent No.: US 7,732,678 B1
(45) Date of Patent: Jun. 8, 2010

(54) COTTON FIBER TRANSCRIPTIONAL FACTORS

(75) Inventors: Kevin McBride, Davis, CA (US); David M. Stalker, Woodland, CA (US); Julie R. Pear, Davis, CA (US); Luis Perez-Grau, Davis, CA (US)

(73) Assignee: Calgene LLC, Davis, CA (US)

( * ) Notice: Subject to any disclaimer, the term of this patent is extended or adjusted under 35 U.S.C. 154(b) by 0 days.

(21) Appl. No.: 08/984,099

(22) Filed: Dec. 3, 1997

Related U.S. Application Data

(63) Continuation-in-part of application No. PCT/US96/09897, filed on Jun. 7, 1996, which is a continuation-in-part of application No. 08/480,178, filed on Jun. 7, 1995, now abandoned.

(51) Int. Cl.
- A01H 5/00 (2006.01)
- C07H 21/04 (2006.01)
- C12N 15/82 (2006.01)

(52) U.S. Cl. .................. 800/314; 435/320.1; 435/419; 536/23.2; 536/23.6; 536/24.1; 800/282

(58) Field of Classification Search ........... 800/282, 800/298, 314, 278; 435/320.1, 419; 536/23.6, 536/24.1, 23.2; 935/64

See application file for complete search history.

(56) References Cited

U.S. PATENT DOCUMENTS

| | | | |
|---|---|---|---|
| 4,801,540 A | 1/1989 | Hiatt et al. | 435/411 |
| 4,943,674 A | 7/1990 | Houck et al. | 800/287 |
| 5,004,863 A | 4/1991 | Umbeck et al. | 800/288 |
| 5,159,135 A | 10/1992 | Umbeck et al. | 800/314 |
| 5,487,991 A * | 1/1996 | Vandekerckhove et al. | 435/172.3 |
| 5,495,070 A * | 2/1996 | John | 800/205 |
| 6,096,950 A * | 8/2000 | John | 800/314 |
| 6,166,301 A * | 12/2000 | Delmer et al. | 800/314 |

FOREIGN PATENT DOCUMENTS

| | | |
|---|---|---|
| EP | 87306739.1 | 2/1988 |
| EP | 89118346.9 | 4/1990 |
| WO | WO 88/09334 | 12/1988 |
| WO | WO 89/12386 | 12/1989 |
| WO | WO 91/13980 | 9/1991 |
| WO | WO 92/15675 | 9/1992 |
| WO | WO 96/40924 | * 12/1996 |

OTHER PUBLICATIONS

T Link (Oct. 22, 1989) Oregonian p. L03.*
PN Benfey et al (1990) Plant Cell 2: 849-856.*
JNM Mol et al (1989) Plant Molecular Biology 13: 287-294.*
MC Deeley et al (1981) J Bacteriology 147: 787-796.*
S Hart et al (1992) J General Microbiology 138: 211-216.*
TM Klein et al (1989) Proc Natl Acad Sci USA 86: 6681-6685.*
John, M. E. et al., "Gene expression in cotton (Gossypium hirsutum L.) fiber: Cloning of the mRNAs." 1992, Proc. Natl. Acad. Sci. USA, vol. 89, pp. 5769-5773.*
Kim, Y. et al., "A 20 nucleotide upstream element is essential for the nopaline synthase (nos) promoter activity." 1994, Plant Molecular Biology, vol. 24, pp. 105-117.*
Benfey, P. N. and Chua N. , "The Cauliflower Mosaic Virus 35S Promoter: Combinatorial Regulation of Transcription in Plants." 1990, Science, vol. 250, pp. 959-966.*
Koziel, M. G. et al., "Optimizing expression of transgenes with an emphasis on post-transcriptional events." 1996, Plant Molecular Biology, vol. 32, pp. 393-405.*
Stam, M. et al., "The Silence of Genes in Transgenic Plants." 1997, Annals of Botany, vol. 79, pp. 3-12.*
Smith, C. J. S. et al., "Antisense RNA inhibition of polygalacturonase gene expression in transgenic tomatoes." 1988, Nature, vol. 334, pp. 724-726.*
An et al. (1988) *Plant Physiol*, 88: 547-552.
Barbacid et al. (1987) *Ann. Rev. Biochem.*, 56: 779-827.
Barker et al. (1983) *Plant Molecular Biology*, 2: 335-350.
Bednarek et al. (1994) *Plant Physiol*, 104: 591-596.
Benfey et al. (1989) *Science*, 244: 174-181.
Bernan et al. (1985) *Gene*, 37: 101-110.
Bird et al. (1988) *Plant Molecular Biology*, 11: 651-662.
Chrispeels et al. (1992) *Cell*, 68: 613-616.
della-Cioppa et al. (1990) *Bio/Technology*, 8: 634-638.
Finch et al. (1986) *Nucleic Acids Research*, 14: 8583-8603.
Gasser et al. (1988) *Journal of Cellular Biochemistry*, 12C: 137.
Goldberg et al. (1988) *Science*, 240: 1460-1467.
Hass et al. (81) *Biochemistry*, 20: 2256-2260.
Hiat et al. (1988) *Journal of Cellular Biochemistry*, 12C: 148.
Larkins et al. (1985) *Journal of Cellular Biochemistry*, 9C: 264.
Marshall et al. (1993) *Reviews*, 18: 250-254.
Martineau et al. (1991) *Mol Gen Genet*, 228: 281-286.
McCormick et al. (1987) *Tomato Biotechnology*, 255-265.
McCormick et al. (1986) *Plant Cell Reports*, 81-84.
Murai et al. (1983) *Science*, 222: 476-482.
Piechulla et al. (1986) *Plant Molecular Biology*, 7: 367-376.
Terryn et al. (1993) *Plant Molecular Biology*, 22: 143-152.
Yang et al. (1993) *Proc. Natl. Acad. Sci.*, 90: 8732-8736.
Grierson et al. (1986) *Nucleic Acids Res.* 14: 8595-8603.
Martineau, B. et al. (1990) *J. of Cellular Biochemistry* 14E: 306.

* cited by examiner

*Primary Examiner*—Amy J. Nelson
(74) *Attorney, Agent, or Firm*—Alissa M. Eagle; Dennis R. Hoerner, Jr.; Grace L. Bonner

(57) ABSTRACT

Novel DNA constructs are provided which may be used as molecular probes or inserted into a plant host to provide for modification of transcription of a DNA sequence of interest in cotton fiber, particularly in very early fiber development. The DNA constructs comprise a cotton fiber transcriptional initiation regulatory region associated with a gene which is expressed in cotton fiber.

47 Claims, 40 Drawing Sheets

```
CTT TCT ATT TGG TTA ACC ATG GCT CAT AAC TTT CGT CAT CCT TTC TTC
Leu Ser Ile Trp Leu Thr Met Ala His Asn Phe Arg His Pro Phe Phe>
                20                      40
CTT TTC CAA CTT TTA CTC ATT ACT GTC TCA CTA ATG ATC GGT AGC CAC
Leu Phe Gln Leu Leu Leu Ile Thr Val Ser Leu Met Ile Gly Ser His>
         60                      80                     140
100
 *
ACC GTC TCG TCA GCG GCT CGA CAT TTA TTC CAC ACA CAA ACA ACC TCA
Thr Val Ser Ser Ala Ala Arg His Leu Phe His Thr Gln Thr Thr Ser>
                 160                     180
TCA GAG CTG CCA CAA TTG GCT TCA AAA TAC GAA AAG CAC GAA GAG TCT
Ser Glu Leu Pro Gln Leu Ala Ser Lys Tyr Glu Lys His Glu Glu Ser>
         200                     220                    240
          *
GAA TAC AAA CAG CCA AAA TAT CAT GAA GAG TAC CCA AAA CAT GAG AAG
Glu Tyr Lys Gln Pro Lys Tyr His Glu Glu Tyr Pro Lys His Glu Lys>
                 260                     280
CCT GAA ATG TAC AAG GAG GAA AAA CAA AAA CCC TGC AAA CAT CAT GAA
Pro Glu Met Tyr Lys Glu Glu Lys Gln Lys Pro Cys Lys His His Glu>
         300                     320
          *
GAG TAC CAC GAG TCA CGC GAA TCG AAG GAG CAC GAA GAG TAC GAT AAA
Glu Tyr His Glu Ser Arg Glu Ser Lys Glu His Glu Glu Tyr Asp Lys>
```

FIGURE 1A

```
                                              380
340                           360
GAA AAA CCC GAT TTC CCC AAA TGG GAA AAG CCT AAA GAG CAC GAG AAA
Glu Lys Pro Asp Phe Pro Lys Trp Glu Lys Pro Lys Glu His Glu Lys>
                    400                 420
                     *
CAC GAA GTC GAA TAT CCG AAA ATA CCC GAG TAC AAG GAC AAA CAA GAT
His Glu Val Glu Tyr Pro Lys Ile Pro Glu Tyr Lys Asp Lys Gln Asp>
            440                 460                         480
GAG AAT AAG AAA CAT AAA GAT GAA GAG TGC CAG GAG TCA CAC GAA TCG
Glu Asn Lys Lys His Lys Asp Glu Glu Cys Gln Glu Ser His Glu Ser>
                        500                 520
                         *
AAA GAG CAC GAA GAG TAC GAG AAA GAA AAA CCC GAT TTC CCC AAA TGG
Lys Glu His Glu Glu Tyr Glu Lys Glu Lys Pro Asp Phe Pro Lys Trp>
            540                 560
GAA AAG CCT AAA GGG CAC GAG AAA CAT AAA GCC GAA TAT CCG AAA ATA
Glu Lys Pro Lys Gly His Glu Lys His Lys Ala Glu Tyr Pro Lys Ile>
                    600                             620
                     *
CCT GAG TGC AAG GAA AAA CTA GAT GAG GAT AAG GAA CAT AAA CAT GAG
Pro Glu Cys Lys Glu Lys Leu Asp Glu Asp Lys Glu His Lys His Glu>
            640                             660
TTC CCA AAG CAT GAA AAA GAA GAG GAG AAG AAA CCT GAG AAA GGC ATA
Phe Pro Lys His Glu Lys Glu Glu Glu Lys Lys Pro Glu Lys Gly Ile>
```

FIGURE 1B

```
                                                                              720
                680                          700
                                              *
GTA CCC TGA GTG GGT TAA AAT GCC TGA ATG GCC GAA GTC CAT GTT TAC
Val Pro *** Val Gly *** Asn Ala *** Met Ala Glu Val His Val Tyr>

740                          760
TCA GTC TGG CTC GAG CTC CAC TAA GCC TTA AGC CAT ATG ACA CTG GTG CAT
Ser Val Trp Leu Glu His *** Ala Leu Ser His Met Thr Leu Val His>

780                          800
                                              *
GTG CCA TCA TCA TGC AGT AAT TTC ATG GGA TAT TGT AAT TAT ATT GTT
Val Pro Ser Ser Cys Ser Asn Phe Met Gly Tyr Cys Asn Tyr Ile Val>

840                          860
AAT AAA AAA GAT GGT GAG TGG GAA ATG TGT GTG TGC ATT CAT CCA TGA
Asn Lys Lys Asp Gly Glu Trp Glu Met Cys Val Cys Ile His Pro ***>

880                          900
                                              *
GCA ATG CTG AAT CTC TTT GCA TGC ATA GAG ATT CTG AAT GGT TAT AGT
Ala Met Leu Asn Leu Phe Ala Cys Ile Glu Ile Leu Asn Gly Tyr Ser>

940                          960
TTA TGT TAT ATC GTT TGT TCT AGT GAA ATT AAT TTT GAA TGT TGT ATG
Leu Cys Tyr Ile Val Cys Ser Ser Glu Ile Asn Phe Glu Cys Cys Met>

920
TAA TGT T
*** Cys Xxx>
```

FIGURE 1C

```
                    20                  40                  60
ACTAAAGGGA ACAAAAGCTG GAGCTCCACC GCGGTGGCGG CCGCTCTAGA ACTAGTGGAT
            80                 100                 120
                                 *
CCCCCGTGGA CTAAACAAAA CATGGGAAGA TTTGCTGTAA AAAAATAAAA GAAGCTTACT
           140                 160                 180
CAATAACACT TTGTGAATTG TATACAAAAG ACTCAATGAA AAACAATAAC TCAATACACT
           200                 220                 240
             *
TTTTTTCACT GATTTACATC CTTTATATAG GCTGAAACTA CAACAACTTT AGCTAAAAAA
           260                 280                 300
                                                       *
ATAGGATAAC CTAATAGCAA AATCACAATC AGATATTAAA CCATGATTTT AGCTAACCAT
           320                 340                 360
TTAACAACTT TATTGAAACT AATTTGAATA TTTCATCTGC TGATATGCCC AAGATTTTAG
           380                 400                 420
                                   *
GCCACTAACC GATTTGGTGG TGAACTTTAA CATGTCATGC ATTTGTAACT GTTTGAAACA
           440                 460                 480
AGTTTTTTGC ATTATTTTAC TATATGAACT GTTGATTAG GTTGAGTTAC ACACTGAGCT
           500                 520                 540
             *
TGTAAGCTCA CTCAAATTTT TCTAAATTCT AAGGTGATCA GCAAACTTAG GACCGGGCGG
           560                 580                 600
                                                       *
CGTACGAGAG CTCGGATTGA TTTTCTAGTT AATAAATAAG ACGATTTATG TTTTTAAACT
```

Figure 2A

```
                     620                                 640                                 660
ATTATGGACT  TTTTGGACTA  TGTAACTGTT  TGGGACTTTA  TTTTTGTTTT  TTATTTGCTT
                     680                                 700                                 720
                                                          *
TTTTTGGATT  TAGTAATTAT  TATTTTTAAA  CTGCAAAATT  ATATGTTTTT  ACAAACTAAG
                     740                                 760                                 780
TCACAGTTTT  CAAAATTCCA  TAACTTAGAA  TTTTTCGCTG  CAAAATAAAG  TAATCATTTA
                     800                                 820                                 840
                     *
AGTGTTTTTT  CTGTAATAAA  ATAAATAAAT  AATTTAACG   AGTATTTTCC  TAAAAATTGG
                     860                                 880                                 900
                                                                                             *
AAATTGATTT  ACCAAAAATTA GTATGTCAAA  ACACATGTTT  ATATGTTACA  GGGCGATATC
                     920                                 940                                 960
GTCTAGGCAA  ATAACATCTA  GGCGGGGTTT  GGAGTGTTAC  AGGGCGAGTG  GGCTCATTTT
                     980                                1000                                1020
                                                          *
GAGTAAGTAT  AGTTAGGGCC  GAGTTTTAGA  TTGCATATTC  AAGGTCAAAG  ATTTTGTAAA
                    1040                                1060                                1080
CTTCGATGAA  TGATATGTAT  GATTGTCCGA  TTAACGAAAT  ATGTTTTTTT  CTTTTGTGTG
                    1100                                1120                                1140
          *
TGTTTTATCT  CGTGTGATAA  GTATATAGTA  TGTTTTATTC  CAATTCTTAT  GGCATGTGAC
                    1160                                1180                                1200
                                                                                             *
ATTGTGGCTA  TTCTAATTAA  ATTGATTTGT  TATTATTGAA  ATCTGATGCA  TCTGTTCTAC

Figur 2B
```

```
                    1220                 1240                 1260
AAAGCATGGA ATCTCATGCC TACTGCTTTC TGTTAAAGAT ACGATTGCAA GTTTAACATG
         1280                 1300                 1320
                               *
CTTACTATTT TGATTTTGTC CTTGCATGCT ATGTCACATT ACATGGGGTT GGGATGATAT
         1340                 1360                 1380
GGTAAGGAGG AAGTTTTGAC AGTTTAATGA TTTGCACTAT CTGGTGGTTT AACCACATAT
         1400                 1420                 1440
         *
TTGTTATGGC ATCTTGACTG CGGTTATGGT GGCTCGACCG CCCATATCTG TTCTGAAAT
         1460                 1480                 1500
                                                  *
TTATCTGTGA CTCTGGTGGC ATTGTCTACA ATTATTTGTT GGTGTGTTTT GGATGGACGA
         1520                 1540                 1560
GTCGTGGGGA ACTCTATTTG GTGTGTTGCG GAGTTGGGTA GGAAATTTTC GAAAAAAATT
         1580                 1600                 1620
                               *
TGCATTGTGT TTTTCTGAAA AATATTGCAT TAACATAAATC ATGCATTCTC AATTTTGGTC
         1640                 1660                 1680
AATTGAACGT TATAAAATTC TCTATGATAT CCTGATCTGT TTATTACATT ATATGTGTTT
         1700                 1720                 1740
         *
ATGCTTGAGT TAAGTCAAAC ATTGAGATTC ATAGCTCACC CAATTATTTA ATCATTTCAG
         1760                 1780                 1800
                                                  *
GCAATCTGCA GACTTAGGAT TGGATGGCGT TCAGGAGCTT GGATTGGTTT TCTCACATCA
         1820                 1840                 1860
TATTTTATTA AATAATTATT AATTAAAATT TATGGACTTT TGGACTGTCT GACTAATTTT
```

Figure 2C

```
                         1880                   1900                   1920
CAGAATTTTA TTTTGGTTTT GGGTTTTGTT GAATTTTTTA GATAATTATT TTAAATATTC
         1940                   1960                   1980
TGCATAATTT TTCTGTTATT TGAAAAGGAT GTTCGAATTT TTTTTCAAAA TTGAAACGTT
         2000                   2020                   2040
          *
TAAGAATTTT TACTACTGCA AATTCAGAAT AAGTGAATTT GTTTTTTAGA AAGATTAAAT
         2060                   2080                   2100
                                                      *
AAGTTAGTAT TACGATTTTT AGTTTGATTT GGTGGAAAGT AATGTATGTT TTTGAACATA
         2120                   2140                   2160
ATTATTTGAC AATAATTAAG TTTTCTAGGG AATAAACGGA AATATCTTCT TCTTTTTTGT
         2180                   2200                   2220
                              *
AAAATTACTA ATGCAAGAAC AAACAACGTT TTGGGGAGCA AATAATCTAG CTTTAAGTAG
         2240                   2260                   2280
TCAGTGTAAC TCTCAAAATC TGGTCATAAC TTCTAGGCTG AGTTTGCTGT GCTACAGTAC
         2300                   2320                   2340
          *
TAAGTCTATA GAAACTTACC TGACAAAACG ACATGACGTC AGGGTCGAAT CTACAACTTT
         2360                   2380                   2400
                                                      *
TCCTTTTTCT TCAATTAACA TATGGTTGAT TCAAGTTCCG ATCTATAATA ATTTATTACG
         2420                   2440                   2460
ATTTATCAAT TTCAATTACC TTATATCATC CTATTATAAA TATAAGTCAG TTCAATTCAG
```

Figure 2D

```
                    2480                    2500                    2520
                                              *
TTTTCGAAAG TTCCCAAAAA TTTTGAATTT TATTAAATTT ATTCCCTAAA ACCGAAATAG
           2540                    2560                    2580
TTATATCTTT CAAATTTAAG TTTCATTTTT CAATCCGATT TCAATTTCAT CCTTTTATAA
  2600                    2620                    2640
    *
CTCTCTATTA TCTATAATTA CATAAATTTC AAATTAATTT TGAAATATTT ACACTTTAGT
                    2660                    2680                    2700
                                                                    *
CCCTAAGTTC AAAACTATAA ATTTTCACTT TAGAAATTAA TCATTTTTCA CATCTAAGCA
           2720                    2740                    2760
TCAAATTTAA CCAAATGACA CAAATTTCAT GATTAGTTAG ATCAAGCTTT TGAGTCTTCA
  2780                    2800                    2820
    *
AAACATAAAA ATTACAAAAA AAAAACAAAC TTAAAATCAT TTATCAATTT GAACAACAAA
                    2840                    2860                    2880
GCTTGGCCGA ATGCTAAGAG CTTAAAAAATG GCTTCTTTTG TTTCTTTTTG TTGCAAACGG
           2900                    2920                    2940
                  *
TGGAGAGAAG AGGGAAATGA AGATTGACCA TATTTTTTTA TTATGTTTTA ACATATAATA
  2960                    2980                    3000
                                              *
TTAATAATTT AATCATAATT ATACTTTGGT GAATGTGACA GTGGGGAGAT ACGTAAAGTA
           3020                    3040                    3060
TTTTAACATT ATACTTTTTG CAAGCAGTTG GCTGGTCTAC CCAAGAGTGA TCAAAGTTTG
  3080                    3100                    3120
```

Figure 2E

```
AGCTGCCTTC AATGAGCCAA TTTTTGCCCA TAATGGAATAA AGGCAATTTG TTTAGTTCAA
                                      *                        3180
CTGCTCACAG AATAATGTTA AAATGAAATT AAAATAAGGT GGCCTGGTCA CACACACAAA
       3200                 3160                3220          3240
           *
AAAAAACTAA TGTTGGTTCG TTGAATTTTA TATTACGGAA TGTAATATTA TATTTTAAAA
       3260                 3280                3300
                                                   *
TAAAATTATG TTATTTAGAT TCTTAATATT TTGGAGCATT CCATACTATA ATTTCGTAAC
       3320                 3340                3360
ATAATATTAA AATATAGTAA TATAAAGTGT AATTAACTTT AAAATTACAAG CATAATATTA
       3380                 3400                3420
                              *
AATTTTTGAAT CAATTAATTT TTATTTCTAT TATTTTAATT AATTTAGTCT ATTTTTTCAA
       3440                 3460                3480
AATAAAAATT AAATCTAAAT AAAAAATAAT TTTCCTTAAT GTTGAAACAA CTCATGTTAT
       3500                 3520                3540
           *
ACTTCAAAAT TATAAGTATT ATATTTACCT TGATGATTTA TTTATTAGTA TATTAATTCT
       3560                 3580                3600
                                                    *
GATTACAAAT ATGGTGGGAT ACAATCGCTT TCCACTAAAT ATTTTAACTA TGATTTATAA
       3620                 3640                3660
ATTTATTTCA ACATCGTATA TTTACTTATT AATACATAAT TTATCATAAT TTTATGGAAA
       3680                 3700                3720
                              *
```

Figure 2F

```
TTGAGACCAA GAAACATTAA GAGAACAAAT TCTATAACAA AGACAATTTA GAAAAAAATG
                                3740                              3760                              3780
           TACTTTTAGG TAATTTTAAG TACTCTTAAC CAAACACAAA AATTCAAATC AAATGAACTA
            3800                              3820                              3840
              *
AATAAGATAA TATAACATAC GGAACATCTT ACTTGTAATC TTACATTCCC ATAATTTTAT
                 3860                              3880                              3900
                                                                  *
TATGAAAAAT AATCTTATAT TACTCGAACT AAATGTTGTC ACAAATTATT ATCTAAATAA
                 3920                              3940                              3960
AGAAAAACAC TTAATTTTTA TAACATTTTT TCATATATTT GAAAGATTAT ATTTTGTATA
            3980                              4000                              4020
                                              *
TTTACGTAAA AATATTTGAC ATAGATTGAG CACCCTTCTTA ACATAATCCC ACCATAAGTC
                                4040                              4060                              4080
AAGTATGTAG ATGAGAAATT GGTACAAAACA ACGTGGGGCC AAATCCCACC AAACCATCTC
            4100                              4120
              *
TCATTCTCTC CTATAAAAGG CTTGCTACAC ATAGACAACA ATCCACACA C AAA TAC
 4140                             4160                                      <Phe Val
ACG TTC TTT TCT TTC TAT TTG ATT AAC CAT GGC TCA TAG CAT TCG TCA
<Arg Glu Lys Arg Gln Ile Asn Val Met Ala *** Leu Met Arg ***
                                                       4180
                   4200                                            4220
CCC TTT CTT CCT TTT CCA ACT TTT ACT CAT AAG TGT CTC ACT AGT GAC
<Gly Lys Lys Arg Lys Trp Ser Lys Met Ser Leu Thr Lys Glu Ser Thr Val

Figure 2G
```

```
                    4240                         4260                              4280
CGG TAG CCA CAC TGT TTC GGC AGC GGC ACG TTT ATT CGA GAC ACA
<Pro Leu Trp Val Thr Ala Ala Arg Arg Lys Asn Ser Val Cys
                              4300
                              *

AGC AAC CTC ATC AGA GCT CCC ACA ATT GGC TTC AAA ATA CGA AAG CAC
<Ala Val Glu Asp Ser Ser Gly Cys Asn Ala Glu Phe Tyr Ser Leu Val
                    4340                         4360

GAG AGT CTG AAT ACG AAA AGC CAG AAT ACA AAC AGC CAA AGT ATC ACG
<Leu Thr Gln Ile Arg Phe Ala Leu Ile Cys Val Ala Leu Thr Asp Arg
          4380                         4400                         4420
                                       *

AAG AGT ACT CAA AAC TTG AGA AGC CTG AAA TGC AAA AGG AGG AAA AAC
<Leu Thr Ser Leu Val Gln Ser Ala Gln Phe Ala Phe Pro Pro Phe Val
                              4440                         4460
                                                           *

AAA AAC CCT GCA AAC AGC ATG AAG AGT ACC ACG AGT CAC ACG AAT CAA
<Phe Val Arg Cys Val Ala His Leu Thr Gly Val Arg Thr Val Arg Ile Leu
          4480                         4500                         4520
                                       *

AGG AGC AAA AAG AGT ACG AGA AAG AAA ATC TCGACGAA                    4580
<Pro Ala Phe Leu Thr Arg Ser Leu Phe Asp
                    4540                4560
                                        *
CGTCGACGGC TAGCGAAGAT CTTCGGGCCC GTCGAGCCTT GAATCATATG ACACTGGTGC
                    4600                                  4640
                    *                                     
ATGTGCCATC ATCATGCAGT AATTTCATGG TATATCGTAA TATATAGTTA ATAAAAAAGA
                    4660                         4700
                                                 *
TGGTGATTGG GAAATGTGTG TGTGCATTCC TCCATGCACT AATGGTGAAT CTCTTTGCAT
```

Figure 2H

```
            4720                  4740                  4760
ACATAGAAAT TCTAAATGGT TATAGTTTAT GTTATAGTGT ATGTTGTAGT GAAATTAATT
            4780                  4800                  4820
                                    *
TTAAATGTTG TATCTAATGT TAACATCACT TGGCTTGATT TATGTTATGT TATGTATTTT
            4840                  4860                  4880
ACTTTAATGA TATTGCATGT ATTGTTAATT TAACATTGCT TGATCATTAT ACTCTTCTAC
            4900                  4920                  4940
              *
TATTAATTAT AAATGGCACT GTTTTGTTTA AACTTTTTAC AAGTTAAGAC ATGTATAAAT
            4960                  4980                  5000
                                                          *
ATATGACAAT ATAATTACAG GTTTTAGTTC AATGTTAGCT ATCTTAGTAT GTTATTGATG
            5020                  5040                  5060
ATCTTAATTA CATTTAAACA AATTCCACTT AAAATTTTAA TAAATAATAA CAAATAATTA
            5080                  5100                  5120
              *                     *
TTGTAATATA ATACATTAAA TGCAACAAAA AATGAAATAA ATAAAATAAA ATAGCAAATA
            5140                  5160                  5180
ATTGTTATAA TATTGTAATA TAATATGTAC CATATTCTTA ACTGAAATAG GGTCTAACCT
            5200                  5220                  5240
              *
ATAATCCCTA AAATTTCAGT TTAAATATTT TTATACCTAC CATATTATTA GAACTCTTTT
            5260                  5280                  5300
                                                          *
TAAAATATATT AAAATTTAA TTATACCAAT TTATACCAAT TTAATTAAAC TATTAATTAT TATTAATTAT CTTAACTAAA
```

Figure 2I

```
                      5320                            5340                            5360
ATCTAAAATT TTATTAACC TATTAATAAA TTCCTAATTA TCTTATCTAA TTTAAAACTC
           5380                            5400                            5420
TAATTATCCT AATTTAATTT AAATTCTTAA TTATCTTAAT TTGTAACCTC CTCCACCCAG
                      5440                            5460                            5480
CTAGATGCTG GACCCGAATC CGGGAGATTA CATCGGCCAT TGAGATGGCG TGATCAGGGT
                      5500                            5520                            5540
TTGGCGCGCC GGTACCCAAT TCGCCCTATA GTGAGTTCGT ATTACGCGCG CTCACTGCGT
CCCGTTT
```

Figure 2J

```
                      20                    40                    60
ACTAAAGGGA ACAAAAGCTG GAGCTCCACC GCGGTGGCGG CCGCTCTAGG ATCCCCCGTG
           80                   100                   120
                                  *
GACTAAACAA AACATGGGAA GATTTGCTGT AAAAAAATAA AAGAAGCTTA CTCAATAACA
          140                   160                   180
CTTTGTGAAT TGTATACAAA AGACTCAATG AAAAACAATA ACTCAATACA CTTTTTTTCA
          200                   220                   240
           *
CTGATTTACA TCCTTTATAT AGGCTGAAAC TACAACAACT TTAGCTAAAA AAATAGGATA
          260                   280                   300
                                                        *
ACCTAATAGC AAAATCACAA TCAGATATTA AACCATGATT TTAGCTAACC ATTTAACAAC
          320                   340                   360
TTTATTGAAA CTAATTTGAA TATTTCATCT GCTGATATGC CCAAGATTTT AGGCCACTAA
          380                   400                   420
                                  *
CCGATTTGGT GGTGAACTTT AACATGTCAT GCATTTGTAA CTGTTTGAAA CAAGTTTTTT
          440                   460                   480
GCATTATTTT ACTATATGAA CTGTTTGATT AGGTTGAGTT ACACACTGAG CTTGTAAGCT
          500                   520                   540
           *
CACTCAAATT TTTCTAATTT CTAAGGTGAT CAGCAAACTT AGGACCGGGC GGCGTACGAG
```

Figure 3A

```
                                560                    580                    600
                                                                                 *
AGCTCGGATT GATTTCTAG TTAATAAATA AGACGATTTA TGTTTTTAAA CTATTATGGA
                 620                    640                    660
CTTTTTGGAC TATGTAACTG TTTGGGACTT TATTTTTGTT TTTTATTTGC TTTTTTTGGA
                 680                    700                    720
                                         *
TTTAGTAATT ATTATTTTTA AACTGCAAAA TTATATGTTT TTACAAAACTA AGTCACAGTT
                 740                    760                    780
TTCAAAATTC CATAACTTAG AATTTTTCGC TGCAAAATAA AGTAATCATT TAAGTGTTTT
                 800                    820                    840
                 *
TTCTGTAATA AAATAAATAA ATAATTTTAA CGAGTATTTT CCTAAAAAATT GGAAATTGAT
                 860                    880                    900
                                                                 *
TTACCAAAAT TAGTATGTCA AAACACATGT TTATATGTTA CAGGGCGATA TCGTCTAGGC
                 920                    940                    960
AAATAACATC TAGGCGGGGT TTGGAGTGTT ACAGGGCGAG TGGGCTCATT TTGAGTAAGT
                 980                    1000                   1020
                                        *
ATAGTTAGGG CCGAGTTTTA GATTGCATAT TCAAGGTCAA AGATTTTGTA AACTTCGATG
                1040                    1060                   1080
AATGATATGT ATGATTGTCC GATTAACGAA ATATGTTTTT TTCTTTTGTG TGTGTTTTAT
```

Figur 3B

```
         1100       1120       1140
          *
CTCGTGTGAT AAGTATATAG TATGTTTTAT TCCAATTCTT ATGGCATGTG ACATTGTGGC
         1160       1180       1200
                                          *
TATTCTAATT AAATTGATTT GTTATTATTG AAATCTGATG CATCTGTTCT ACAAAGCATG
         1220       1240       1260
GAATCTCATG CCTACTGCTT TCTGTTAAAG ATACGATTGC AAGTTTAACA TGCTTACTAT
         1280       1300       1320
                              *
TTTGATTTTG TCCTTGCATG CTATGTCACA TTACATGGGG TTGGGATGAT ATGGTAAGGA
         1340       1360       1380
GGAAGTTTTG ACAGTTTAAT GATTTGCACT ATCTGGTGGT TTAACCACAT ATTTGTTATG
         1400       1420       1440
          *
GCATCTTGAC TGCGGTTATG GTGGCTCGAC CGCCCATATC TGTTCTGGAA ATTTATCTGT
         1460       1480       1500
                                          *
GACTCTGGTG GCATTGTCTA CAATTATTTG TTGGTGTGTT TTGGATGGAC GAGTCGTGGG
         1520       1540       1560
GAACTCTATT TGGTGTGTTG CGGAGTTGGG TAGGAAATTT TCGAAAAAAA TTTGCATTGT
         1580       1600       1620
                              *
GTTTTTCTGA AAAATATTGC ATTAACATAA TCATGCATTC TCAATTTTGG TCAATTGAAC
```

Figure 3C

```
                    1640                1660                1680
GTTATAAAAT TCTCTATGAT ATCCTGATCT GTTTATTACA TTATATGTGT TTATGCTTGA
                    1700*               1720                1740
GTTAAGTCAA ACATTGAGAT TCATAGCTCA CCCAATTATT TAATCATTTC AGGCAATCTG
                    1760                1780                1800*
CAGACTTAGG ATTGGATGGC GTTCAGGAGC TTGGATTGGT TTTCTCACAT CATATTTTAT
                    1820                1840                1860
TAAATAATTA TTAATTAAAA TTTATGGACT TTTGGACTGT CTGACTAATT TTCAGAATTT
                    1880                1900*               1920
TATTTTGGTT TTGGGTTTTG TTGAATTTTT TAGATAATTA TTTTAAATAT TCTGCATAAT
                    1940                1960                1980
TTTTCTGTTA TTTTGAAAAGG ATGTTCGAAT TTTTTTTTCAA AATTGAAACG TTTAAGAATT
                    2000*               2020                2040
TTTACTACTG CAAATTCAGA ATAAGTGAAT TTGTTTTTTA GAAAGATTAA ATAAGTTAGT
                    2060                2080                2100*
ATTACGATTT TTAGTTTGAT TTGGTGGAAA GTAATGTATG TTTTTGAACA TAATTATTTG
                    2120                2140                2160
ACAATAATTA AGTTTTCTAG GGAATAAACG GAAATATCTT CTTCTTTTTT GTAAAATTAC

Figure 3D
```

```
                                          2180                    2200                    2220
                                                                   *
TAATGCAAGA ACAAACAACG TTTTGGGGAG CAAATAATCT AGCTTTAAGT AGTCAGTGTA
                                          2240                    2260                    2280
ACTCTCAAAA TCTGGTCATA ACTTCTAGGC TGAGTTTGCT GTGCTACAGT AGTAAGTCTA
                                          2300                    2320                    2340
                                           *
TAGAAACTTA CCTGACAAAA CGACATGACG TCAGGGTCGA ATCTACAACT TTTCCTTTTT
                                          2360                    2380                    2400
                                                                                           *
CTTCAATTAA CATATGGTTG ATTCAAGTTC CGATCTATAA TAATTTATTA CGATTTATCA
                                          2420                    2440                    2460
ATTTCAATTA CCTTATATCA TCCTATTATA AATATAAGTC AGTTCAATTC AGTTTTCGAA
                                          2480                    2500                    2520
                                                                   *
AGTTCCCAAA AATTTTGAAT TTTATTAAAT TTATTCCCTA AAACCGAAAT AGTTATATCT
                                          2540                    2560                    2580
TTCAAATTTA AGTTTCATTT TTCAATCCGA TTTCAATTTC ATCCTTTTAT AACTCTCTAT
                                          2600                    2620                    2640
                                           *
TATCTATAAT TACATAAATT TCAAATTAAT TTTGAAATAT TTACACTTTA GTCCCTAAGT
                                          2660                    2680                    2700
                                                                                           *
TCAAAACTAT AAATTTTCAC TTTAGAAATT AATCATTTTT CACATCTAAG CATCAAATTT
```

Figure 3E

```
                        2720                      2740                      2760
AACCAAATGA CACAAATTTC ATGATTAGTT AGATCAAGCT TTTGAGTCTT CAAAACATAA
          2780                      2800                      2820
                                       *
AAATTACAAA AAAAAAACAA ACTTAAAATC ATTATCAAT TTGAACAACA AAGCTTGGCC
                        2840                      2860                      2880
GAATGCTAAG AGCTTAAAAA TGGCTTCTTT TGTTTCTTTT TGTTGCAAAC GGTGGAGAGA
          2900                      2920                      2940
             *
AGAGGGAAAT GAAGATTGAC CATATTTTTT TATTATGTTT TAACATATAA TATTAATAAT
                        2960                      2980                      3000
                                                                    *
TTAATCATAA TTATACTTTG GTGAATGTGA CAGTGGGGAG ATACGTAAAG TATTTTAACA
          3020                      3040                      3060
TTTATACTTTT TGCAAGCAGT TGGCTGGTCT ACCCAAGAGT GATCAAAGTT TGAGCTGCCT
                        3080                      3100                      3120
                                       *
TCAATGAGCC AATTTTTGCC CATAATGGAT AAAGGCAATT TGTTTAGTTC AACTGCTCAC
          3140                      3160                      3180
AGAATAATGT TAAAATGAAA TTAAAATAAG GTGGCCTGGT CACACACACA AAAAAAAACT
                        3200                      3220                      3240
                           *
AATGTTGGTT GGTTGAATTT TATATTACGG AATGTAATAT TATATTTTAA AATAAAATTA
```

Figure 3F

```
                              3260                           3280                           3300
                                                                                              *
TGTTATTTAG ATTCTTAATA TTTTGGAGCA TTCCATACTA TAATTCGTA ACATAATATT
                              3320                           3340                           3360
AAAATATAGT AATATAAAGT GTAATTAACT TTAAATTACA AGCATAATAT TAAATTTGA
                              3380                           3400                           3420
                                                              *
ATCAATTAAT TTTTATTTCT ATTATTTAA TTAATTTAGT CTATTTTTC AAAATAAAAT
                              3440                           3460                           3480
TTAAATCTAA ATAAAAATAA TTTTTCCTTA ATGTTGAAAC AACTCATGTT ATACTTCAAA
                              3500                           3520                           3540
                               *
ATTATAAGTA TTATATTTAC CTTGATGATT TATTTATTAG TATATTAATT CTGATTATAA
                              3560                           3580                           3600
                                                                                              *
TTATGGTGGG ATACAATCGC TTTCCACTAA ATATTTTAAC TATGATTTAT AAATTTATTT
                              3620                           3640                           3660
CAACATCGTA TATTTACTTA TTAATACATA ATTTATCATA ATTTTATGGA AATTGAGACC
                              3680                           3700                           3720
                                                              *
AAGAAACATT AAGAGAACAA ATTCTATAAC AAAGACAATT TAGAAAAAAA TGTACTTTTA
                              3740                           3760                           3780
GGTAATTTTA AGTACTCTTA ACCAAACACA AAAATTCAAA TCAAATGAAC TAAATAAGAT
```

Figur 3G

```
                                                                                3840
                                                      3820
                         3800
                           *
AATATAACAT ACGGAACATC TTACTTGTAA TCTTACATTC CCATAATTTT ATTATGAAAA
                                                                                3900
                                                      3880                         *
                         3860
ATAATCTTAT ATTACTCGAA CTAAATGTTG TCACAAATTA TTATCTAAAT AAAGAAAAAC
                                                                                3960
                                                      3940
                         3920
ACTTAATTTT TATAACATTT TTTCATATAT TTGAAAGATT ATATTTGTA TATTTACGTA
                                                                                4020
                                                      4000
                         3980                            *
AAAATATTTG ACATAGATTG AGCACCTTCT TAACATAAATC CCACCATAAG TCAAGTATGT
                                                                                4080
                                                      4060
                         4040
AGATGAGAAA TTGGTACAAA CAACGTGGGG CCAAATCCCA CCAAACCATC TCTCATTCTC
                                                      4120
                         4100
                            *
TCCTATAAAA GGCTTGCTAC ACATAGACAA CAATCCACAC A CA AAT ACA CGT TCT
                                                     <Ile Cys Thr Arg
                                                                4180
                                                4160
 4140
 TTT CTT TCT ATT TGA TTA ACC ATG G CTCATAGCAT TCGTCACCCT TTCTTCCTTT
 <Lys Arg Asn Ser *** Gly His
                                                      4240
                         4200
                            *
TCCAACTTTT ACTCATAAGT GTCTCACTAG TGACCGGTAG CCACACTGTT TCGGCAGCGG
                                                      4300
                         4280                            *
CTCGACGTTT ATTCGAGACA CAAGCAACCT CATCAGAGCT CCCACAATTG GCTTCAAAAT
```

Figure 3H

```
      4320           4340           4360
ACGAAAAGCA CGAAGAGTCT GAATACGAAA AGCCAGAATA CAAACAGCCA AAGTATCACG
      4380           4400           4420
                        *
AAGAGTACTC AAAACTTGAG AAGCCTGAAA TGCAAAAGGA GGAAAAAACAA AAACCCTGCA
      4440           4460           4480
AACAGCATGA AGAGTACCAC GAGTCACACG AATCAAAGGA GCAAAAAGAG TACGAGAAAG
      4500           4520           4540
        *
AAAATCTCGA CGGGCCCGAA GATCTTCGCT AGCCGTCGAC GCCCGGGGA ATTCGTCGAG
      4560           4580           4600
                                      *
CCTTGAATCA TATGACGCTG GTGCATGTGC CATCATCATG CAGTAATTTC ATGGTATATC
      4620           4640           4660
GTAATATATA GTTAATAAAA AAGATGGTGA TTGGGAAATG TGTGTGTGCA TTCCTCCATG
      4680           4700           4720
                        *
CACTAATGGT GAATCTCTTT GCATACACATAG AAATTCTAAA TGGTTATAGT TTATGTTATA
      4740           4760           4780
GTGTATGTTG TAGTGAAAKT AATTTTAAAT GTTGTATCTA ATGTTAACAT CACTTGGCTT
      4800           4820           4840
        *
GATTTATGTT ATGTTATGTA TTTTACTTTA ATGATATTGC ATGTATTGTT AATTTAACAT
      4860           4880           4900
                                      *
TGCTTGATCA TTATACTCTT CTACTATTAA TTATAAATGG CACTGTTTTG TTTAAACTTT

Figure 3I
```

```
                                      4940                          4960
TTACAAGTTA AGACATGTAT AAATATATGA CAATATAATT ACAAGTTTTA GTTCAATGTT
    4980                          5000                          5020
                                    *
AGCTATCTTA GTATGTTATT GATGATCTTA ATTACATTTA AACAAATTCC ACTTAAAATT
    5040                          5060                          5080
TTAATAAATA ATAACAAATA ATTATTGTAA TATAATACAT TAAATGCAAC AAAAAATGAA
    5100                          5120                          5140
       *
ATAAATAAAA TAAAATAGCA AATAATTGTT ATAATATATT AATATAATAT GTACCATATT
    5160                          5180                          5200
                                                            *
CTTAACTGAA ATAGGGTCTA ACCTATAATC CCTAAAATTT CAGTTTAAAT ATTTTTATAC
    5220                          5240                          5260
CTGCCATATT ATTAGAACTC TTTTTAAATA TATTAAAATT TTAATTATAC CAATTTAATT
    5280                          5300                          5320
                           *
TAAACTATTA ATTATCTTAA CTAAAATCTA AAATTTTATT TAACCTATTA ATTAAATTCC
    5340                          5360                          5380
TAATTATCTT ATCTAATTTA AAACTCTAAT TATCCTAATT TGATTTAAAT TCTTGATTAT
    5400                          5420                          5440
   *
CTTAATTTGT AACCTCCTCC ACCCAGCTAG ATGCTGGACC CGAATCCGGG AGATTACATC

Figur    3J
```

```
         5460       5480                            5500
GGCATTGAGA TGGCCTAGTA GTGATCAGGG TTTTCTAGAG GTACCCAATT CGCCCTATAG
                                                   *
TGAGTCGT
```

Figur 3K

| | |
|---|---|
| AAAAAACA ATG AGC ACT GCA AGA TTT ATC AAG TGT GTC ACG GTC GGT GAT<br>Met Ser Thr Ala Arg Phe Ile Lys Cys Val Thr Val Gly Asp<br>1 5 10 | 50 |
| GGA GCT GTG GGG AAA ACT TGT ATG CTC ATT TCA TAT ACC AGC AAT ACT<br>Gly Ala Val Gly Lys Thr Cys Met Leu Ile Ser Tyr Thr Ser Asn Thr<br>15 20 25 30 | 98 |
| TTC CCA ACG GAT TAT GTT CCA ACA GTA TTT GAT AAC TTT AGT GCC AAT<br>Phe Pro Thr Asp Tyr Val Pro Thr Val Phe Asp Asn Phe Ser Ala Asn<br>35 40 45 | 146 |
| GTG GTG GTG GAT AGC ACA GTG AAC CTT GGC CTA TGG GAC ACT GCC<br>Val Val Val Asp Ser Thr Val Asn Leu Gly Leu Trp Asp Thr Ala<br>50 55 60 | 194 |
| GGG CAA GAA GAT TAT AAT AGG CTA AGG CCA CTG AGT TAT AGA GGA GCT<br>Gly Gln Glu Asp Tyr Asn Arg Leu Arg Pro Leu Ser Tyr Arg Gly Ala<br>65 70 75 | 242 |
| GAT GTG TTT TTG GCC TTT CTT ATA AGC AAG GCC AGT TAT GAA<br>Asp Val Phe Leu Ala Phe Ser Leu Ile Ser Lys Ala Ser Tyr Glu<br>80 85 90 | 290 |
| AAC ATC TAC AAA AAG TGG ATC CCA GAG CTA AGA CAT TAT GCT CAT AAT<br>Asn Ile Tyr Lys Lys Trp Ile Pro Glu Leu Arg His Tyr Ala His Asn<br>95 100 105 110 | 338 |
| GTA CCA GTT GTG CTT GGA CTT GTT GGA ACC AAA CTA GAT TTG CGA GAT GAC AAG<br>Val Pro Val Val Leu Gly Val Gly Thr Lys Leu Asp Leu Arg Asp Asp Lys<br>115 120 125 | 386 |
| CAG TTC CTC ATT GAT CAC CCT GGA GCA ACA CCA ATA TCA ACA TCT CAG<br>Gln Phe Leu Ile Asp His Pro Gly Ala Thr Pro Ile Ser Thr Ser Gln<br>130 135 140 | 434 |

FIGURE 4A

```
GGA GAA GAA CTA AAG AAG ATG ATA GGA GCA GTT ACT TAT ATA GAA TGC    482
Gly Glu Glu Leu Lys Lys Met Ile Gly Ala Val Thr Tyr Ile Glu Cys
            145                 150                 155

AGC TCC AAA ACC CAA CAG AAT GTG AAG GCT GTT TTC GAT GCT GCA ATA    530
Ser Ser Lys Thr Gln Gln Asn Val Lys Ala Val Phe Asp Ala Ala Ile
        160                 165                 170

AAA GTA GCT TTG AGG CCA CCA AAA AGA AAG CCT TGC AAA AGG            578
Lys Val Ala Leu Arg Pro Pro Lys Arg Lys Pro Cys Lys Arg
175                 180                 185         190

AGA ACA TGT GCT TTC CTT TGAATATTGG ATCATTATTA CAGTCAAAAA            626
Arg Thr Cys Ala Phe Leu
                195

CAGTTAACAA AAGCTGTTGC AGATAAACAC TGAATCTGCT ATAGTTTGTT TTTGGTTTAC   686

ATATGTTCCA CGTGAAACTA TGAAGCATCT CTAAGAAAAC CCAAACTATC ATATCAACCC   746

ATCGATCAAT GAATCGATTT CAATTTTCGC AGTATAAGTT CCTTTTAATC CTTTCTTTT    806

ACTTCATTTT ATAACGAATT CTATGGATAA TGTTCCCTAC AAACATGTCA TTACAATGTT   866

TAATTATAAA TTCCATTCTT CTATTTTACT AAAAAAAAAA AAAA                   910
```

FIGURE 4B

```
                20                    40                    60
TTGGATGAGAGA ACCAATTTTT AATAGTAAAN CCTAACCAAT TTTTAATAAT AAAGCTGACT 80                   100                   120
                                       *
CCTAGTACAA GAGCTTTTAT TCATTCTTCT ATTTTGCTTT CCTCTAGGCT TGGCAATCGA 140                   160                   180
GAATTTCTT GTGTTACAAT ATAATAAATA CATCGTAGAA ATAAATTTTA TTCAAATTGA 200                   220                   240
                *
AGTCTTAACC ATCTTTAATA TTTGTAGATG TAATTTAAAT GAAAGATAAA TACATATTCT 260                   280                   300
                                                              *
TGGACATGTA TTTTCATCTT AATGTTTGTG GCTTTGGTGA TAGGTGTATT GATGTACGAT 320                   340                   360
GTCTTTTAAA TCACATATCA CATTTTGAGT TTGTATGATG ATAAGTCGAC ATAANCGAAA 380                   400                   420
                                       *
TATGGTGTGA TCTTCACTTT TGAACTTTGA TAAGTCACCA AACTTTAACA AAGTTTGATT 440                   460                   480
GTGTACATAT ATATATATAT CTTCAAATTT TATAATAAAA ATTGTGTTTA AATAATTTAC 500                   520                   540
                *
AGTTATATTA TTTTTTTATC TCTAATTTTA TTTGTCGCCA AATTTTTAGT TGATATTTTA 560                   580                   600
                                                              *
ACATAAAAAA AATTGTACAC ATTACAAGC CCATATACAA ATAATTATAT AAATATTCAT
```

FIGURE 5A

```
          620                   640                   660
TAAAAAATAT ATTTAAATAT AGGATATAAA TATAACTATT TTAGAATTAT TCTACTTTAA
          680                   700                   720
                                  *
GATAACATAG GTTAAAATGTA TAATTAATAA GGTTAGTTTA TTGTAAAGAT GAGTATATAT
          740                   760                   780
GTCGTAAACA TAATCACTAA CCATTTTTAT TAACTTCTTG GTTTTGAAGT TCCAAAAAGA
          800                   820                   840
            *
AAATGGAAGG GAAATTTGAG AGTAAGTTCA TGTTTATATT ATACATAATG AAGTTGATGT
          860                   880                   900
                                                        *
TTTCTTCTTT TTAATATTTT TATACAAAAT ATTTAAATAA AATAATTAAG GATTGAATGA
          920                   940                   960
AAAATATAAT GAAAGTCGTT TTACTAATAG TCATATTGCA TTTTGTCGCA TCTACTTAAA
          980                   1000                  1020
            *
TAATAGATAA ATTAATTGTG GTACATTAGA TCAAAGAACA AACTAGATTT TGTCCCATTC
          1040                  1060                  1080
TATTGTTAAA AGCTGGTCCG TTTACATTAA AATAAGGTAC ATGTTACATG CCACGTATAA
          1100                  1120                  1140
            *
CTATCTGGTT ATTCTATCAA TCACGCTAAT TTTTAACAGT AGAAATGAAT GTAATTTTTA
          1160                  1180                  1200
                                                        *
AATAGAAAGG GTCAAATTGT TATTTGATCT AACACGTAGG GATTAATTTA CTTATTTTCC
```

FIGURE 5B

```
                        1220                      1240                      1260
TAAAGAAATA AGTAAAATAT AATTTGAATC TTAATACAAA AACTTTCATG ATACTTTTAT
                        1280                      1300                      1320
                                                   *
CATATTTTAC TTATAATTTA ATATTGTGAG AGTAACAAAR TTAAAAAACA TAGAAACACC
                        1340                      1360                      1380
AAAAGTTAGT TATGGTGTGA CTCATATACA CAGTTAAAAT TTGAATAAAT TTTTTTCTTC
                        1400                      1420                      1440
                         *
GTCATTAAATT CCATCATGGG TTTTTTTTTT TCTAGTTAAG CCATAATTAT CAAAATAATC
                        1460                      1480                      1500
                                                                             *
ATCATTAAATC CTATCAATAC CCCGCCCTGC CTCCCTCCCT CAATACTTAA ACCCAACTAA
                        1520                      1540                      1560
CACCCAGCAC CAAACGCACT TTAATAGCCA CCTATTTCTA GCCATGTCCT TGCACTTAAA
                        1580                      1600                      1620
                                                   *
GAAAAGTAAA GCTAACCTGC AATCATTCCA TATCGAGGCC TCAACAGATA AAGTTGGTTG
                        1640                      1660                      1680
ATGGGTTTGC ACCAAGTTGT TAAAACCCGG CCCTCAACTT CCCTTTTCTT TTCATCCTCC
                        1700                      1720                      1740
                         *
CCACTCCACA CCCTCCAATT TTCTTCATAT GGTTCTATTA TAAGTTCTTT ATAATCACAG
                        1760                      1780                      1800
                                                                             *
AATCAAGATA AGTCCTCAGC AAACAAAAAA CCATGGCTCT CGAGCAAGAT CTGGACTAGT
```

FIGURE 5C

```
                1820       1840       1860
CAGAGCTCTG AATATTGGAT CATTATTACA GTCAAAAACA GTTAACAAAAA GCTGTTGCAG
           1880       1900       1920
                       *
ATAAACACTG AATCTGCTAT AGTTTGTTTT TGGTTTACAT ATGTTCCACG TGAAACTATG
           1940       1960       1980
AAGCATCTCT AAGAAAACCC AAACTATCAT ATCAACCCAT CGATCAATGA ATCGATTTCA
           2000       2020       2040
           *
ATTTTCGCAG TATAAGTTCC TTTTAATCCT TTCTTTTTAC TTCATTTTAT AACGAATTCT
           2060       2080       2100
                                             *
ATGGATAAATG TTCCCTACAA ACATGTCATT ACAATGTTTA ATTATAAATT CCATTCTTCT
           2120       2140       2160
ATTTTACTAA GATATTAGTA ACTTCAAACT GCTGATTTTT ACTAATTTAT TATTTATAAA
           2180       2200       2220
                       *
TTGTTAGAAT GATTATTTTT CAATAATTTA ACAACAATAT TTAATATTAT TATTATTATT
           2240       2260       2280
ATTTCTCAAT TTTTATTAAA CAAAAACATA AATTTTTGAC AAAATTAAAAT AAATGAATTA
           2300       2320       2340
           *
ATTTCTCAAT TTTTCGTGCA ACTATTACAA AAATCCTTCA TAGTCCTAAT CTTAATTTGA
           2360       2380       2400
                                             *
TGCAGAGGTG ATAATAATCT TAATTTGATG CAGAGGTAAT AATGGGCCGG GTTGAGCTG
```

FIGURE 5D

```
              2420                2440                2460
GACTTAAGCA TGATATTGAC GTACTTTATA TTTTTCCAAA TTCAACCCAG CTCGAAATAT
                                 2480                         2520
                                      *
GAGTCTAAAA TTTTGTCCAA TTTAATCCAA GCCCATTTTA AGTTCGTCCA TATTATTTTT
              2540                2560                2580
TAATTTAAAA AATTTATATC ATTTTATTTT AATATTTAAT TATTTTATAT ATTTTTTATT
              2600                2620                2640
                   *
TATTGAAAAT TTTTATATAG TCATCTTAAC ATTATGTTAA TGTTTATATT AGAGTAGTAT
                                 2660                         2700
                                                                   *
TATATATATT TAGTATAGGT TTATTTTGTT AATAAACTTA AAAATGGGTC TTGTGGGCTA
              2720                2740                2760
GACTTGGACC TTAAATGCTC AAACTCAAAC TTAATTCATA TTTTAAACAG GCTTAATATT
              2780                2800                2820
                                      *
TTTATTTACA CTGTTTCAAA TTTTTCGGGT GAAATATCTT CGAGTCTAGA TTAATAACAC
                                 2840                         2880
CACAGGTCTA ATTTGATGCT CAATGAAAAT GAAATCATAT TGAGCTTAAT TAATATTCCA
              2900                2920                2940
                   *
TTCTTCTTTG CTGAAAGGAC CAAGCAATTC GAGTTACATT AAGGTTAAAG AGTATGGGAT
                                 2960                         3000
                                                                   *
CCGCCAAACC TGCCCCAATG TCTCTTCAAC CATCCAAAAA CTTGAGTCAG TATCACATAC
```

FIGURE 5E

```
                    3020                          3040
ATGTACCGNT ATTTATTTAT TTATTGAAAT TGGCATTATT TCTTG
```

FIGURE 5F

```
GGGCATTCCA  CACGACCATG  TGTCCCCTAT  TTCCAGGCAT  TTTGAGACTT  CACCTAAACT    60
TCTAGAGTTG  TTTCAAATTA  GCCCCTATTT  GTTCTTAAAT  CATTTTAGGA  TCTTGTAAAC   120
TCGTATTTAG  GACTAAATGT  GTAATTTATA  CTTTAATTAT  GATTGATTAA  TTGATTGATT   180
TNGTAGTAAT  GCCCGTGACC  CTAATCCGTT  AGCGAAGAGG  GGTTAGGGGT  TAGGGGTTTT   240
ATTATTATTT  TTTAGATATT  GTATAACTCT  TGTTTTATTT  TTAATTTTGT  TACTATTTCA   300
AAGGCATTTG  TTTGTAGTGT  TATTTCGAGT  AGGTTTTATG  GGTGAACAAC  CCTTGACCGC   360
CAAATCAATC  ACAAGAGTTC  AACATTTTAT  TTATTTTGAA  ATGTATTAAA  AATCGTTAAT   420
CTATATATTC  GCCCCATTAT  TGGGATTAAA  TATTCACACAAG  GGTTTAGACC  GTCATGAGAC   480
AGATTAGTTT  TATCTTACTG  ATGGTCACAT  CACAATAGTA  ATTCAACTTA  ATACGAGAGG   540
AACCATTGAT  TCACGCAATT  GGTCATCGCA  CTTAGTTGAA  AAGCTAGGGG  TGCGAAGCTA   600
CCGTACGCTG  GATTATGATT  GAACACCTCT  AAGTCAGAAT  CCGAATTAGA  AACAATGCAC   660
GTGTCCGTTG  CCTGATTGCC  AACCCCAATA  ACACGTGTTG  TAGGTTTAAC  CATGTTTATG   720
AAAGATAAGG  TTTTTTTTTT  TATAAGCAAG  CAACTATAGG  GGTTTACTTC  CGTGCGCAAA   780
TTTTTAGGTT  ACCTATTTTG  GGAGGGGGGA  TTATGATTCA  AGTGAAAGAA  AGTTGGCACA   840
CACACAATCA  GTACATCTGT  TTTGACAGAG  ACACAGCCTA  AAAACAGCAG  CAAACAAGCC   900
TAAAGGAATC  ACCCAAAAAC  AACAACCAAA  AGTACAGAGG  AAAACAAAAG  AATCCCTGTT   960
ACCACCAAGC  TGAAAAAAAG  AAAATAAAAC  TCAACTTTTG  GCAATAAAAA  CCCTCCTACC  1020
CTCAACCCCT  AACCACGCAA  CAATCAGCAA  TACTCCAAGC  AACCATTTTC  CTTACAAGTT  1080
```

FIGURE 7A

```
TGTTTTCTT GTGATTAATC CAT ATG GCT AGC TCC ATG TCC CTT AAG CTT GCA 1133
                    His Met Ala Ser Ser Met Ser Leu Lys Leu Ala>

TGT CTG CTA GTG TTG TGC ATG GTG GTG GGT GCA CCC CTG GCT CAA GGG  1181
Cys Leu Leu Val Leu Cys Met Val Val Gly Ala Pro Leu Ala Gln Gly>

GAC GTA ACC CGT GCT GAT GGC GTA GTC ACC CTT CCA CGC TGC CTT CCT  1229
Asp Val Thr Arg Ala Asp Gly Val Val Thr Leu Pro Arg Cys Leu Pro>

TTA TTG ATA GGG AAT GGT AAT GGT GCT GAT GCT GAT GTT GAT GCC CCA  1277
Leu Leu Ile Gly Asn Gly Asn Gly Ala Asp Ala Asp Val Asp Ala Pro>

GCT TGC TGC GAC ATC GTC AGG GGT CTC TTG AGC TCG CTG CTC TGT GGT  1325
Ala Cys Cys Asp Ile Val Arg Gly Leu Leu Ser Ser Leu Leu Cys Gly>

GGT GTT TAGGAACCG ATCTAGCTTG AAATCGGGTT CGGATACGGG TGGAGTTTCA    1380
Gly Val>

AATTGGTGTG TTATGGAATC CCAACTTAAT CGTGTTTAGG GGTGGGATCC AATTGTGTGA 1440

TACATTACAG AGCATGGTTG TGGATTGTTT TCTCATATGT TTTGATTGAC TTGCTTGATA 1500

CATTGGATGA TTCGATAAGG TGACCGGTTT ACCTGGGTAT CCAACCATCA TCCGATTACT 1560

TTTTAATAAT TATTTGTTTC TTCTTTATGT TGTCTGTCTT TTTGTTTCTT GATCTATAAC 1620

ATTATATTTG CCCAAATTTT CGCATTTTCC ATATGTAGCT TATATATGTA TATATATATT 1680

CAATAAAGTA TATTGATTTA GCAGATGATT TGTGTATATA TTTAAATCAA ATCAAACATT 1740

AATGATCATT CACTAGCGTC TTAATCTTGA AAAATTCATC AACGGTTATC CTTTGCAGCA 1800

TATATAAAAA AAATTGCCAA CCCTATGCTT TTACACCTAA TTCAAGGGAT AACATAAGTC 1860

GATTAAAACG A                                                    1871
```

FIGURE 7B

| Coker 130 | Yxy, Y | Yxy, x | Yxy, y | Lab, L | Lab, a | Lab, b | LCh, L | LCh, C | LCh, h |
|---|---|---|---|---|---|---|---|---|---|
| 1 | 80.35 | .3206 | 0.3266 | 91.84 | 0.16 | 5.51 | 91.84 | 5.51 | 88.4 |
| 2 | 77.62 | .3232 | 0.3282 | 90.6 | 0.66 | 6.45 | 90.6 | 6.48 | 84.2 |
| 3 | 80.98 | .3197 | 0.3257 | 92.12 | 0.13 | 5.04 | 92.12 | 5.04 | 88.6 |
| 4 | 80.16 | .3200 | 0.3255 | 91.75 | 0.35 | 5.00 | 91.75 | 5.01 | 86.1 |
| 5 | 77.03 | .3220 | 0.3271 | 90.33 | 0.61 | 5.84 | 90.33 | 5.87 | 84.1 |
| 6 | 73.67 | .3258 | 0.3293 | 88.76 | 1.35 | 7.14 | 88.76 | 7.26 | 79.4 |
| 7 | 82.43 | .3178 | 0.3237 | 92.76 | 0.15 | 4.05 | 92.76 | 4.05 | 87.9 |
| 8 | 82.21 | .3196 | 0.3255 | 92.66 | 0.19 | 4.99 | 92.66 | 4.99 | 87.9 |
| 9 | 81.19 | .3194 | 0.3241 | 92.21 | 0.77 | 4.42 | 92.21 | 4.48 | 80.2 |
| 10 | 76.11 | .3243 | 0.329 | 89.9 | 0.74 | 6.89 | 89.9 | 6.92 | 84 |
| 11 | 82.28 | .3178 | 0.3236 | 92.69 | 0.19 | 4.00 | 92.69 | 4.00 | 87.3 |
| TOTAL | 874.03 | 3.5302 | 3.5883 | 1005.62 | 5.30 | 59.33 | 1005.62 | 59.61 | 938.10 |
| MEAN | 79.46 | .3209 | .3262 | 91.42 | 0.48 | 5.39 | 91.42 | 5.42 | 85.28 |
| S.D. | 2.91 | .0026 | .0020 | 1.33 | 0.38 | 1.08 | 1.33 | 1.11 | 3.22 |
| RANGE | 82.43-73.67 | .3858-3178 | 0.3293-.3236 | 92.76-88.76 | 1.35-.13 | 7.14-4.00 | 92.76-88.76 | 7.26-4.00 | 88.6-79.4 |
| AVER DEV | 2.44 | .0021 | .0017 | 1.11 | 0.31 | 0.88 | 1.11 | 0.90 | 2.64 |

| Coker 130 | Hunter L | Hunter a | Hunter B |
|---|---|---|---|
| 1 | 89.63 | 0.15 | 5.42 |
| 2 | 88.10 | 0.66 | 6.27 |
| 3 | 89.98 | 0.13 | 4.98 |
| 4 | 89.53 | 0.36 | 4.94 |
| 5 | 87.76 | 0.61 | 5.69 |
| 6 | 85.83 | 1.35 | 6.85 |
| 7 | 90.79 | 0.15 | 4.03 |
| 8 | 90.67 | 0.19 | 4.95 |
| 9 | 90.10 | 0.78 | 4.38 |
| 10 | 87.23 | 0.75 | 6.65 |
| 11 | 90.70 | 0.19 | 3.98 |
| TOTAL | 980.32 | 5.32 | 58.14 |
| MEAN | 89.12 | 0.48 | 5.29 |
| S.D. | 1.65 | 0.39 | 0.99 |
| RANGE | 90.79-85.83 | 1.35-.13 | 6.85-3.98 |
| AVER DEV | 1.37 | 0.31 | 0.81 |

FIGURE 9

| 5148 | Yxy, Y | Yxy, x | Yxy, y | Lab, L | Lab, a | Lab, b | LCh, L | LCh, C | LCh, h |
|---|---|---|---|---|---|---|---|---|---|
| 68-1 | 60.76 | 0.34 | 0.35 | 82.24 | 2.32 | 15.11 | 82.24 | 15.28 | 81.3 |
| 68-1 | 61.89 | 0.34 | 0.34 | 82.82 | 1.97 | 14.31 | 82.85 | 14.44 | 82.2 |
| 50-2-1 | 78.39 | 0.3324 | 0.3375 | 90.95 | 0.68 | 11.29 | 90.95 | 11.31 | 86.6 |
| 50-2-1 | | | | | | | | | |
| (lint fiber) | 21.49 | .3155 | 0.3489 | 53.48 | -8.01 | 7.97 | 53.48 | 11.29 | 135.2 |

| 5148 | Hunter L | Hunter a | Hunter B |
|---|---|---|---|
| 68-1 | 77.94 | 2.25 | 13.35 |
| 68-1 | 78.67 | 1.92 | 12.75 |
| 50-2-1 | 88.53 | 0.69 | 10.71 |
| 50-2-1 | | | |
| (lint fiber) | 46.35 | -6.35 | 6.06 |

FIGURE 10

| 5149 | Yxy,Y | Yxy,x | Yxy,y | Lab,L | Lab,a | Lab,b | LCh,L | LCh,C | LCh,h |
|---|---|---|---|---|---|---|---|---|---|
| 68-1 | 65.75 | 0.3351 | 0.34 | 84.86 | 0.72 | 11.9 | 84.86 | 11.92 | 86.6 |
| 68-1 | 62.54 | .3458 | 0.3474 | 83.19 | 2.14 | 15.84 | 83.19 | 15.98 | 82.4 |
| 68-1 | 62.56 | 0.3458 | 0.3474 | 83.2 | 2.14 | 15.85 | 83.2 | 15.99 | 82.4 |
| 8-1 | 84.72 | .3196 | 0.3278 | 93.76 | 0.89 | 5.87 | 93.76 | 5.93 | 98.6 |
| 68-1 | 64.97 | .3316 | 0.3354 | 84.46 | 1.17 | 9.81 | 84.46 | 9.87 | 83.3 |
| 17-2 | 64.42 | .3423 | 0.3436 | 84.18 | 2.26 | 14.19 | 84.18 | 14.36 | 81 |
| 17-3 | 60.97 | .3475 | 0.3475 | 82.36 | 2.74 | 16.03 | 82.36 | 16.26 | 80.4 |
| 17-15-1 | 64.02 | .3433 | 0.3444 | 83.97 | 2.34 | 14.57 | 83.97 | 14.75 | 80.9 |
| 21-1 | 59.32 | 0.3443 | 0.3445 | 81.46 | 2.64 | 14.41 | 81.46 | 14.64 | 79.7 |
| 21-3 | 63.64 | 0.34 | 0.3409 | 83.77 | 2.4 | 12.89 | 83.77 | 13.11 | 79.5 |
| 21-6 | 67.12 | 0.3372 | 0.3394 | 85.56 | 1.88 | 12.15 | 85.56 | 12.29 | 81.3 |
| 50-3-1 | 61.26 | 0.3502 | 0.3511 | 82.51 | 2.4 | 17.63 | 82.51 | 17.79 | 82.3 |
| 67-1 | 64.34 | 0.3434 | 0.3442 | 84.13 | 2.48 | 14.58 | 84.13 | 14.78 | 80.4 |
| 68-1 | 64.12 | 0.3442 | 0.3447 | 84.02 | 2.58 | 14.85 | 84.02 | 15.07 | 80.2 |
| 68-2 | 70.21 | 0.3428 | 0.3447 | 87.09 | 2.05 | 15.04 | 87.09 | 15.17 | 82.3 |
| 68-3 | 63.81 | 0.3457 | 0.3468 | 83.86 | 2.35 | 15.76 | 83.86 | 15.93 | 81.6 |

| 5149 | Hunter L | Hunter a | Hunter B |
|---|---|---|---|
| 68-1 | 81.08 | 0.71 | 10.89 |
| 68-1 | 79.08 | 2.08 | 14 |
| 68-1 | 79.09 | 2.09 | 14.02 |
| 8-1 | 92.04 | 0.91 | 5.81 |
| 68-1 | 80.6 | 1.15 | 9.06 |
| 17-2 | 80.25 | 2.21 | 12.75 |
| 17-3 | 78.08 | 2.68 | 14.09 |
| 17-15-1 | 80.01 | 2.29 | 13.05 |
| 21-1 | 77.01 | 2.56 | 12.73 |
| 21-3 | 79.77 | 2.35 | 11.65 |
| 21-6 | 81.92 | 1.86 | 11.14 |
| 50-3-1 | 78.26 | 2.33 | 15.36 |
| 67-1 | 80.2 | 2.43 | 13.07 |
| 68-1 | 80.07 | 2.53 | 13.28 |
| 68-2 | 83.79 | 2.04 | 13.68 |
| 68-3 | 79.87 | 2.3 | 14 |

FIGURE 11

| 5616 | Yxy,Y | Yxy,x | Yxy,y | Lab,L | Lab,a | Lab,b | LCh,L | LCh,C | LCh,h |
|---|---|---|---|---|---|---|---|---|---|
| 11-1 | 72.26 | 0.3215 | 0.3254 | 88.09 | 1.1 | 5.06 | 88.09 | 5.17 | 77.8 |
| 11-2 | 58.69 | 0.3284 | 0.3335 | 81.12 | 0.6 | 8.36 | 81.12 | 8.38 | 85.9 |
| 11-2 | 52.78 | 0.3358 | 0.3335 | 77.74 | 3.55 | 9.22 | 77.74 | 9.87 | 69 |
| 11-1 | 72.03 | 0.3312 | 0.3338 | 87.98 | 1.72 | 9.52 | 87.98 | 9.67 | 79.8 |
| 11-1 | 72.34 | 0.3295 | 0.332 | 88.13 | 1.79 | 8.64 | 88.13 | 8.82 | 78.4 |
| 11-1 | 71.98 | 0.3295 | 0.3313 | 87.95 | 2.09 | 8.39 | 87.95 | 8.64 | 76.1 |
| 11-1 | 73.01 | 0.3256 | 0.3305 | 88.45 | 0.68 | 7.51 | 88.45 | 7.54 | 84.9 |
| 17-1-2 | 75.85 | 0.3274 | 0.3306 | 89.78 | 1.52 | 7.94 | 89.78 | 8.08 | 79.3 |
| 17-3-1 | 72.6 | 0.3271 | 0.3303 | 88.25 | 1.48 | 7.66 | 88.25 | 7.8 | 79.1 |
| 17-4-1 | 69.02 | 0.3352 | 0.3377 | 86.51 | 1.78 | 11.37 | 86.51 | 11.5 | 81.2 |
| 25-11-1 | 69.5 | 0.3364 | 0.3401 | 86.75 | 1.26 | 12.41 | 86.75 | 12.47 | 84.2 |
| 25-28-1 | 72.21 | 0.3324 | 0.3343 | 88.06 | 2.09 | 9.9 | 88.06 | 10.11 | 78.2 |
| 25-36-2 | 70.46 | 0.3327 | 0.3353 | 87.22 | 1.73 | 10.22 | 87.22 | 10.36 | 80.5 |
| 35-35-1 | 75.59 | 0.3268 | 0.3299 | 89.66 | 1.56 | 7.58 | 89.66 | 7.73 | 78.4 |
| 50-12-1 | 73.13 | 0.3284 | 0.3316 | 88.5 | 1.46 | 8.36 | 88.5 | 8.48 | 80.1 |
| KS-11-2 | 65.33 | 0.3371 | 0.3388 | 84.65 | 2.07 | 11.83 | 84.65 | 12 | 80.1 |

| 5616 | Hunter L | Hunter a | Hunter B |
|---|---|---|---|
| 11-1 | 85 | 1.09 | 4.89 |
| 11-2 | 76.61 | 0.58 | 7.64 |
| 11-2 | 72.64 | 3.38 | 8.22 |
| 11-1 | 84.87 | 1.72 | 8.97 |
| 11-1 | 85.05 | 1.79 | 8.2 |
| 11-1 | 84.84 | 2.08 | 7.96 |
| 11-1 | 85.44 | 0.67 | 7.18 |
| 17-1-2 | 87.08 | 1.52 | 7.62 |
| 17-3-1 | 85.2 | 1.48 | 7.31 |
| 17-4-1 | 83.07 | 1.76 | 10.52 |
| 25-11-1 | 83.36 | 1.25 | 11.43 |
| 25-28-1 | 84.97 | 2.08 | 9.32 |
| 25-36-2 | 83.94 | 1.72 | 9.56 |
| 35-35-1 | 86.94 | 1.57 | 7.29 |
| 50-12-1 | 85.51 | 1.46 | 7.96 |
| KS-11-2 | 80.82 | 2.04 | 10.81 |

FIGURE 12

COTTON FIBER TRANSCRIPTIONAL FACTORS

This application is a continuation-in-part of PCT application PCT/US96/09897 filed Jun. 7, 1996, which is a continuation-in-part of U.S. Ser. No. 08/480,178 filed Jun. 7, 1995 now abandoned.

TECHNICAL FIELD

This invention relates to methods of using in vitro constructed DNA transcription or expression cassettes capable of directing fiber-tissue transcription of a DNA sequence of interest in plants to produce fiber cells having an altered phenotype, and to methods of providing for or modifying various characteristics of cotton fiber. The invention is exemplified by methods of using cotton fiber promoters for altering the a phenotype of cotton fiber, and cotton fibers produced by the method.

BACKGROUND

In general, genetic engineering techniques have been directed to modifying the phenotype of individual prokaryotic and eukaryotic cells, especially in culture. Plant cells have proven more intransigent than other eukaryotic cells, due not only to a lack of suitable vector systems but also as a result of the different goals involved. For many applications, it is desirable to be able to control gene expression at a particular stage in the growth of a plant or in a particular plant part. For this purpose, regulatory sequences are required which afford the desired initiation of transcription in the appropriate cell types and/or at the appropriate time in the plant's development without having serious detrimental effects on plant development and productivity. It is therefore of interest to be able to isolate sequences which can be used to provide the desired regulation of transcription in a plant cell during the growing cycle of the host plant.

One aspect of this interest is the ability to change the phenotype of particular cell types, such as differentiated epidermal cells that originate in fiber tissue, i.e. cotton fiber cells, so as to provide for altered or improved aspects of the mature cell type. Cotton is a plant of great commercial significance. In addition to the use of cotton fiber in the production of textiles, other uses of cotton include food preparation with cotton seed oil and animal feed derived from cotton seed husks.

Despite the importance of cotton as a crop, the breeding and genetic engineering of cotton fiber phenotypes has taken place at a relatively slow rate because of the absence of reliable promoters for use in selectively effecting changes in the phenotype of the fiber. In order to effect the desired phenotypic changes, transcription initiation regions capable of initiating transcription in fiber cells during development are desired. Thus, an important goal of cotton bioengineering research is the acquisition of a reliable promoter which would permit expression of a protein selectively in cotton fiber to affect such qualities as fiber strength, length or color.

Relevant Literature

Cotton fiber-specific promoters are discussed in PCT publications WO 94/12014 and WO 95/08914, and John and Crow, *Proc. Natl. Acad. Sci. USA* 89:5769-5773, 1992. cDNA clones that are preferentially expressed in cotton fiber have been isolated. One of the clones isolated corresponds to mRNA and protein that are highest during the late primary cell wall and early secondary cell wall synthesis stages. John and Crow, supra.

U.S. Pat. No. 5,175,095 describes tomato transcriptional factors which can be used to direct the transcription of DNA in ovary tissue. The factors are expressed immediately prior to anthesis and through flowering.

A class of fruit-specific promoters expressed at or during anthesis through fruit development, at least until the beginning of ripening, is discussed in European Application 88.906296.4, the disclosure of which is hereby incorporated by reference. cDNA clones from tomato displaying differential expression during fruit development have been isolated and characterized (Mansson et al., *Mol. Gen. Genet.* (1985) 200:356-361. Slater et al., *Plant Mol. Biol.* (1985) 5:137-147). These studies have focused primarily on mRNAs which accumulate during fruit ripening. One of the proteins encoded-by the ripening-specific cDNAs has been identified as polygalacturonase (Slater et al., *Plant Mol. Biol.* (1985) 5:137-147).

A cDNA clone which encodes tomato polygalacturonase has been sequenced (Grierson et al., *Nucleic Acids Research* (1986) 14:8395-8603). Improvements in aspects of tomato fruit storage and handling through transcriptional manipulation of expression of the polygalacturonase gene have been reported (Sheehy et al., *Proc. Natl. Acad. Sci.* USA (1988) 85:8805-8809; Smith et al., *Nature* (1988) 334: 724-726).

Mature plastid mRNA for psbA (one of the components of photosystem II) reaches its highest level late in fruit development, whereas after the onset of ripening, plastid mRNAs for other components of photosystem I and II decline to nondetectable levels in chromoplasts (Piechulla et al., *Plant Molec. Biol.* (1986) 7:367-376). Recently, cDNA clones representing genes apparently involved in tomato pollen (McCormick et al., *Tomato Biotechnology* (1987) Alan R. Liss, Inc., NY) and pistil (Gasser et al., *Plant Cell* (1989), 1:15-24) interactions have also been isolated and characterized.

Other studies have focused on genes inducibly regulated, e.g. genes encoding serine proteinase inhibitors, which are expressed in response to wounding in tomato (Graham et al., *J. Biol. Chem.* (1985) 260:6555-6560: Graham et al., *J. Biol. Chem.* (1985) 260:6561-6554) and on mRNAs correlated with ethylene synthesis in ripening fruit and leaves after wounding (Smith et al., *Planta* (1986) 168: 94-100). Accumulation of a metallocarboxypeptidase inhibitor protein has been reported in leaves of wounded potato plants (Graham et al., *Biochem & BioPhys. Res Comm.* (1981) 101: 1164-1170).

Genes which are expressed preferentially in plant seed tissues, such as in embryos or seed coats, have also been reported. See, for example, European Patent Application 87306739.1 (published as 0 255 378 on Feb. 3, 1988) and Kridl et al. (Seed Science Research (1991) 1:209-219).

In animals, the ras superfamily is subdivided into the subfamilies ras members of which are involved in controlling cell growth and division, rab/YPT members of which control secretory processes, and rho members of which are involved in control of cytoskeletal organization (Bourne et al., (1991) Nature 349: 117-127), and number of homologous genes have now been identified in plants (for a review, see Terryn et al. (1993) *Plant Mol. Biol.* 22: 143-152). None have been found for the important ras subfamily, all but one of the genes identified have been members of the rab/YPT1 subfamily, and there is only one recent report of the cloning of a rho gene in pea (Yang and Watson (1993) *Proc. Natl. Acad. Sci. USA* 90: 8732-8736).

Little work has been done to characterize the functions of these genes in plants, although one recent report has shown that a small G protein from Arabidopsis can functionally complement a mutant form in yeast involved in vesicle trafficking, suggesting a similar function for the plant gene (Bednarek et al., (1994) Plant Physiol 104: 591-596).

In animals, two members of the rho subfamily, called Rac and Rho, have been shown to be involved in the regulation of actin organization (for a review, see Downward, (1992) Nature 359: 273-274).

Rac1 has been shown to mediate growth factor-induced membrane ruffling by influencing microfilament alignment on the plasma membrane (Ridley et al, (1992) Cell 70: 401-410), whereas RhoA regulates the formation of actin stress fibers associated with focal adhesions (Ridley and Hall, (1992) Cell 70: 389-399).

In yeast, the CDC42 gene codes for a rho-type protein which also regulates actin organization involved in the establishment of cell polarity required for the localized deposition of chitin in the bud scar (Adams et al., (1990) *J. Cell Biol.* 111: 131-143.

Disruption of gene function, either by temperature shifts with a CDC42-temperature-sensitive mutant in yeast (Adams et al., 1990), or by micro-injection into fibroblasts of mutant Rac or Rho proteins exibiting a dominant negative phenotype (Ridley et al., 1992; Ridley and Hall, 1992), leads to disorganization of the actin network.

In plants, control of cytoskeletal organization is poorly understood in spite of its importance for the regulation of patterns of cell division, expansion, and subsequent deposition of secondary cell wall polymers. The cotton fiber represents an excellent system for studying cytoskeletal organization. Cotton fibers are single cells in which cell elongation and secondary wall deposition can be studied as distinct events. These fibers develop synchronously within the boll following anthesis, and each fiber cell elongates for about 3 weeks, depositing a thin primary wall (Meinert and Delmer, (1984) *Plant Physiol.* 59: 1088-1097; Basra and Malik, (1984) *Int. Rev. of Cytol.* 89: 65-113). At the time of transition to secondary wall cellulose synthesis, the fiber cells undergo a synchronous shift in the pattern of cortical microtubule and cell wall microfibril alignment, events which may be regulated upstream by the organization of actin (Seagull, (1990) *Protoplasma* 159: 44-59; and (1992) In: *Proceedings of the Cotton Fiber Cellulose Conference, National Cotton Council of America*, Memphis, Tenn., pp 171-192.

Agrobacterium-mediated cotton transformation is described in Umbeck, U.S. Pat. Nos. 5,004,863 and 5,159,135 and cotton transformation by particle bombardment is reported in WO 92/15675, published Sep. 17, 1992. Transformation of *Brassica* has been described by Radke et al. *Theor. Appl. Genet.* (1988) 75;685-694; *Plant Cell Reports* (1992) 11:499-505.

SUMMARY OF THE INVENTION

Novel DNA constructs and methods for their use are described which are capable of directing transcription of a gene of interest in cotton fiber, particularly early in fiber development and during secondary cell wall development. The novel constructs include a vector comprising a transcriptional and translational initiation region obtainable from a gene expressed in cotton fiber and methods of using constructs including the vector for altering fiber phenotype.

Two promoters, are provided from genes involved in the regulation of cotton fiber development. One, Rac13, is from a protein in cotton which codes for an animal Rac protein homologue Rac13, shows highly-enhanced expression during fiber development. This pattern of expression correlates well with the timing of reorganization of the cytoskeleton, suggesting that the Rac13 cotton gene may, like its animal counterpart, be involved in the signal transduction pathway for cytoskeletal organization.

The other is a promoter from a cotton protein which is unrelated to published proteins, designated 4-4. 4-4 mRNA accumulates in fiber cells at day 17 post anthesis and continues to fiber maturity at days 35 post anthesis. Also provided is a promoter from a lipid transfer protein (referred to as "Ltp") which is preferentially expressed in cotton fiber.

The methods of the present invention include transfecting a host plant cell of interest with a transcription or expression cassette comprising a cotton fiber promoter and generating a plant which is grown to produce fiber having the desired phenotype. Constructs and methods of the subject invention thus find use in modulation of endogenous fiber products, as well as production of exogenous products and in modifying the phenotype of fiber and fiber products. The constructs also find use as molecular probes. In particular, constructs and methods for use in gene expression in cotton embryo tissues are considered herein. By these methods, novel cotton plants and cotton plant parts, such as modified cotton fibers, may be obtained.

Also provided in the instant application are constructs and methods of use relating to modification of color phenotype in fiber tissues. Such constructs contain sequences for expression of genes involved in the production of colored compounds, such as anthocyanins, melanin or indigo, and also may contain sequences which provide for targeting of the gene products to particular locations in the plant cell, such as plastid organelles, or vacuoles. Plastid targeting is of particular interest for expression of genes involved in aromatic amino acid biosynthesis pathways, while vacuolar targeting is of particular interest where the precursors required in synthesis of the pigment are present in vacuoles. Production of melanin, for example, may be enhanced by vacuolar targeting in plant tissues which accumulate tyrosine in vacuoles. Transcriptional initiation regions for expression of color-related genes will be selected on the basis of the tissue for which color modification is desired.

DESCRIPTION OF THE DRAWINGS

FIGS. 1A-1C (SEQ ID NO: 2) show the DNA sequence (SEQ ID NO: 1) encoding the structural protein from cDNA 4-4 (SEQ ID NO: 3-SEQ ID NO: 6).

FIGS. 2A-2J show the sequence to the promoter construct pCGN5606 made using genomic DNA from 4-4-6 genomic clone (SEQ ID NO: 7).

FIGS. 3A-3K show the sequence to the 4-4 promoter construct pCGN5610 (SEQ ID No: 11).

FIGS. 4A-4B (SEQ ID NO: 13) show the cDNA sequence (SEQ ID NO: 12) encoding the Rac13 gene product (SEQ ID NO: 14) expressed in cotton fiber.

FIGS. 5A-5F show the sequence of the promoter region from the rac13 gene (SEQ ID No: 15).

FIGS. 7A-7B (SEQ ID NO: 17) show the sequence of the Ltp promoter region from a cotton fiber specific lipid transfer protein gene (SEQ ID NO: 16) and the cotton fiber specific lipid transfer protein (SEQ ID NO: 18) encoded by the gene.

FIG. 9 provides the results of color measurements taken from fibers of the control Coker 130 cotton used in transformation using color constructs.

FIG. 10 shows the results of measurements made of color of plants transformed by the pCGN5148 construct to express genes for melanin synthesis.

FIG. 11 shows the results of measurements taken of the color of plants transformed by the pCGN5149 construct to express genes for melanin synthesis.

FIG. 12 shows the results of measurements made of color of plants transformed to express genes for indigo synthesis using construct pCGN5616.

FIG. 13 shows control measurements made of naturally colored cotton plants which are produced by non-transgenic colored cotton plants.

DETAILED DESCRIPTION OF THE INVENTION

Figure 6:
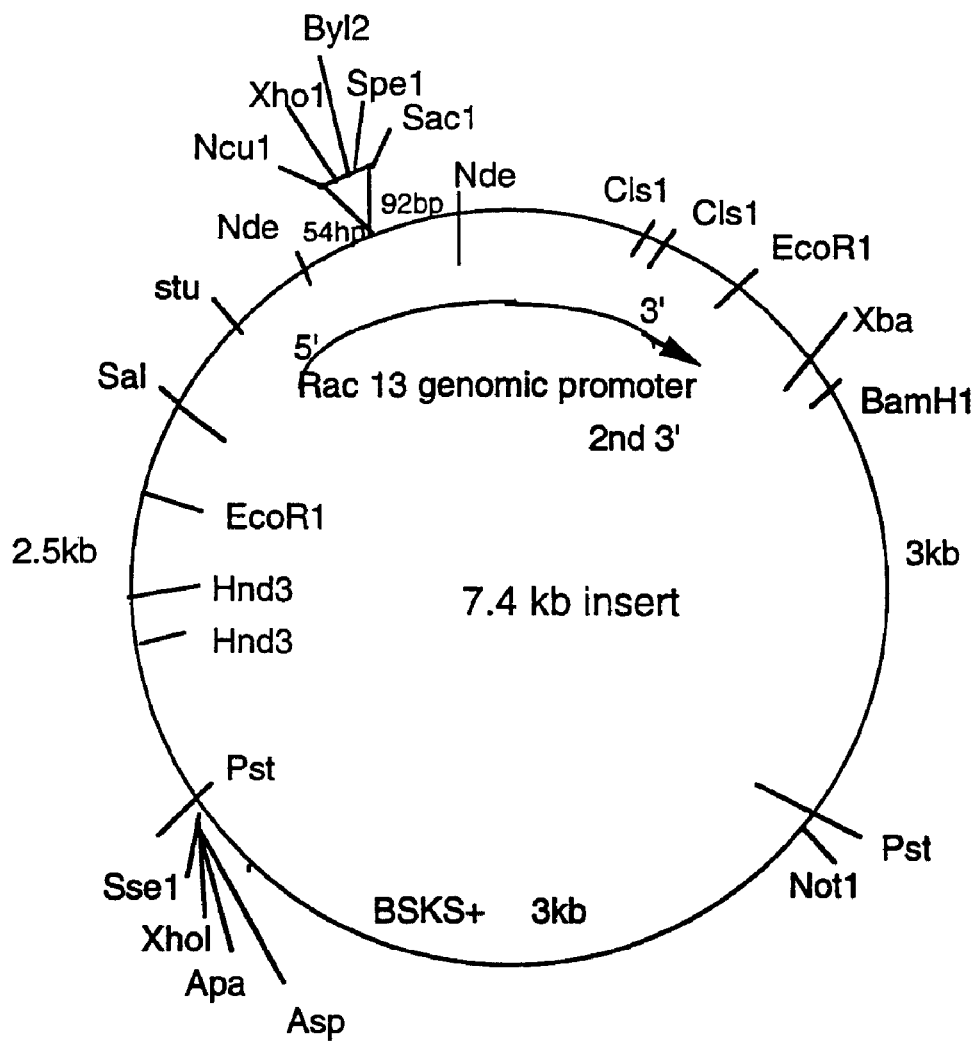
FIG. 6 shows a restriction map for pCGN4735.

In accordance with the subject invention, novel constructs and methods for their use are described which may be used as molecular probes or inserted into a plant host to provide for transcription of a nucleotide sequence of interest in fiber cells as compared with other plant cells, generally preferentially in fiber cells to produce cells and plant parts having an altered phenotype. Of particular interest is the period of at least one to three days prior to anthesis through flower senescence. One promoter was derived from the characterization of two distinct rac cDNA clones isolated from a cotton fiber cDNA library which code for homologs of animal Rac proteins. Using gene-specific probes, it was determined that amphidiploid cotton contains two genes that code for each of the two rac proteins, designated Rac13 and Rac9 respectively. The gene for Rac13 shows highly-enhanced expression in developing cotton fibers, with maximal expression occuring at the time of transition between primary and secondary wall synthesis. This is also the time at which reorganization of the cytoskeleton occurs, and thus the pattern of expression of Rac13 is consistent with its possible role, analogous to animal Rac, in the signal transduction pathway for cytoskeletal organization.

The constructs may include several forms, depending upon the intended use of the construct. Thus, the constructs include vectors, transcriptional cassettes, expression cassettes and plasmids. The transcriptional and translational initiation region (also sometimes referred to as a "promoter,"), preferably comprises a transcriptional initiation regulatory region and a translational initiation regulatory region of untranslated 5' sequences, "ribosome binding sites," responsible for binding mRNA to ribosomes and translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences. Cotton fiber transcriptional initiation regions chosen for cotton fiber modification may include the 4-4, rac13 and Ltp cotton fiber promoter regions provided herein.

The vectors will comprise a nucleotide sequence comprising the transcriptional initiation regulatory regions of this invention associated. A transcriptional cassette for transcription of a nucleotide sequence of interest in cotton fiber will include in the direction of transcription, the cotton fiber transcriptional initiation region, a DNA sequence of interest, and a transcriptional termination region functional in the plant cell. When the cassette provides for the transcription and translation of a DNA sequence of interest it is considered an expression cassette. One or more introns may be also be present.

Other sequences may also be present, including those encoding transit peptides and secretory leader sequences as desired. The regulatory regions are capable of directing transcription in fiber cells from anthesis through flowering but direct little or no expression after the initial changes which occur at the time surrounding pollination and/or fertilization; transcription from these regulatory regions is not detectable at about three weeks after anthesis. Further, fiber-tissue transcription initiation regions of this invention are typically not readily detectable in other plant tissues. Transcription initiation regions from cotton fiber that are not fiber specific may find special application. Especially preferred are transcription initiation regions which are not found at stages of fiber development other than pre-anthesis through flowering. Transcription initiation regions capable of initiating transcription in other plant tissues and/or at other stages of fiber development, in addition to the foregoing, are acceptable insofar as such regions provide a significant expression level in cotton fiber at the defined periods of interest and do not negatively interfere with the plant as a whole, and, in particular, do not interfere with the development of fiber and/or fiber-related parts. Also of interest are cotton fiber promoters and/or promoter elements which are capable of directing transcription in specific cotton fibers such as outer pericarp tissue, inner core tissues, integuments, and the like.

The term "fiber" as used herein refers to the mature organ formed as the result of the development of the fiber wall of a flower and any other closely associated parts. See Weirer, T. E., 1, ed., *Botany A Introduction to Plant Biology* (6th ed.) (John Wiley & Sons, 1982); Tootill & Backmore, *The Facts on File Dictionary of Botany* (Market Home Books Ltd., 1984). By "modified fiber" is meant fiber having a detectably different phenotype from a nontransformed plant of the same species, for example, one not having the transcriptional cassette in question in its genome. The term "anthesis" refers herein to the period associated with flower opening and flowering. The term "flower senescence" refers herein to the period associated with flower death, including the loss of the (flower) petals, etc. Abercrombie, M., et al., *A Dictionary of Biology* (6th ed) (Penguin Books, 1973). Unopened flowers, or buds, are considered "pre-anthesis." Anthesis begins with the opening of the flower petals, which represents asexually receptive portion of the reproductive cycle of the plant. Typically, flowering lasts approximately one week in the tested UCB82 tomato variety. In a plant like cotton, flowering lasts approximately two weeks and the fiber develops from the seed coat tissue. It is preferred that the transcriptional initiation regions of this invention do not initiate transcription for a significant time or to a significant degree prior to plant flower budding. Ideally, the level of transcription will be high for at least approximately one to three days and encompass the onset of anthesis ("pre-anthesis").

Cotton fiber is a differentiated single epidermal cell of the outer integument of the ovule. It has four distinct growth phases; initiation, elongation (primary cell wall synthesis), secondary cell wall synthesis, and maturation. Initiation of fiber development appears to be triggered by hormones. The primary cell wall is laid down during the elongation phase, lasting up to 25 days postanthesis (DPA). Synthesis of the secondary wall commences prior to the cessation of the elongation phase and continues to approximately 40 DPA, forming a wall of almost pure cellulose. In addition to cotton fiber promoters, transcriptional initiation regions from genes expressed preferentially in seed tissues, and in particular seed coat tissues, are also of interest for applications where modification of cotton fiber cells is considered.

Downstream from, and under the regulatory control of, the cotton fiber transcriptional/translational initiation control region is a nucleotide sequence of interest which provides for modification of the phenotype of fiber. The nucleotide sequence may be any open reading frame encoding a polypeptide of interest, for example, an enzyme, or a sequence complementary to a genomic sequence, where the genomic sequence may be an open reading frame, an intron, a noncoding leader sequence, or any other sequence where the complementary sequence inhibits transcription, messenger RNA processing, for example, splicing, or translation. The nucleotide sequences of this invention may be synthetic, naturally derived, or combinations thereof. Depending upon the nature of the DNA sequence of interest, it may be desirable to synthesize the sequence with plant preferred codons. The plant preferred codons may be determined from the codons of highest frequency in the proteins expressed in the largest amount in the particular plant species of interest. Phenotypic modification can be achieved by modulating production either of an endogenous transcription or translation product, for example as to the amount, relative distribution, or the like, or an exogenous transcription or translation product, for example to provide for a novel function or products in a transgenic host cell or tissue. Of particular interest are DNA sequences encoding expression products associated with the development of plant fiber, including genes involved in metabolism of cytokinins, auxins, ethylene, abscissic acid, and the like. Methods and compositions for modulating cytokinin expression are described in U.S. Pat. No. 5,177,307, which disclosure is hereby incorporated by reference. Alternatively, various genes, from sources including other eukaryotic or prokaryotic cells, including bacteria, such as those from *Agrobacterium tumefaciens* T-DNA auxin and cytokinin biosynthetic gene products, for example, and mammals, for example interferons, may be used.

Other phenotypic modifications include modification of the color of plant parts developing from fiber integuments and/or core tissue, for example seed coat hairs, such as cotton fibers. Of interest are genes involved in production of melanin and genes involved in the production of indigo. Melanins are dark brown pigments found in animals, plants and microorganisms, any of which may serve as a source for sequences for insertion into the constructs of the present invention. Specific examples include the tyrosinase gene which can be cloned from *Streptomyces antibioticus*. The ORF438 encoded protein in *S. antibioticus* also is necessary for melanin production, and may provide a copper donor function. In addition, a tyrosinase gene can be isolated from any organism which makes melanin. The gene can be isolated from human hair, melanocytes or melanomas, cuttle fish and red roosters, among others. See, for example, EP Application No. 89118346.9 which discloses a process for producing melanins, their precursors and derivatives in microorganisms. Also, See, Bernan et al. Gene (1985) 37:101-110; and della-Cioppa et al. Bio/Technology (1990) 8:634-638.

Indigo may be obtained by use of genes encoding a monooxygenase such as xylene oxygenase which oxidizes toluene and xylene to (methyl) benzyl alcohol and also transforms indole to indigo. Cloning of the xylene oxygenase gene and the nucleotide and amino acid sequences are described in unexamined Japanese Patent Application Kokai:2-119777, published May 7, 1990. A dioxygenase such as naphthalene dioxygenase which also converts indole to indigo finds use; the naphthalene dioxygenase gene nahA is described in *Science* (1983) 222: 167. For cloning, nucleotide sequence in characterization of genes encoding naphthalene dioxygenase of *Pseudomonas putida*. See, Kurkela et al. *Gene* (1988) 73:355-362. A tryptophanase gene sequence can be used in conjunction with an oxygenase to increase the amount of indole available for conversion to indigo. Sources of tryptophanase gene sequences include *E. coli* (see, for example, Deeley et al. (1982) *J. Bacteriol.* 151:942-951).

As demonstrated in the co-pending application to McBride et al., entitled "Use of Ovary Tissue Transcriptional Factors", Ser. No. 08/480,178, filed on Jun. 7, 1995, the teachings of which are incorporated herein by reference, expression of ORF438 and tyrosinase genes from *Streptomyces* in transgenic tobacco plants using a 4-4 and rac promoter, and targeting the gene products to plastids by the action of transit peptides resulted in phenotypic modification of ovary derived and meristem derived tissues, including modification of color in meristematic regions and basal flower buds. A similar set of experiments in which no plastid targeting sequences were used in conjunction with the ORF438 and tyrosinase genes, no alteration of phenotype was observed. Presumably, the plants were not able to produce melanin due to deficiency of the required substrates in the plant cell cytosol.

Plastid targeting sequences (transit peptides) are available from a number of plant nuclear-encoded plastid proteins, such as the small subunit (SSU) of ribulose bisphosphate carboxylase, plant fatty acid biosynthesis related genes including acyl carrier protein (ACP), stearoyl-ACP desaturase, β-ketoacyl-ACP synthase and acyl-ACP thioesterase, or LHCPII genes. The encoding sequence for a transit peptide which provides for transport to plastids may include all or a portion of the encoding sequence for a particular transit peptide, and may also contain portions of the mature protein encoding sequence associated with a particular transit peptide. There are numerous examples in the art of transit peptides which may be used to deliver a target protein into a plastid organelle. The particular transit peptide encoding sequence used in the instant invention is not critical, as long as delivery to the plastid is obtained.

As an alternative to using transit peptides to target pigment synthesis proteins to plastid organelles, the desired constructs may be used to transform the plastid genome directly. In this instance, promoters capable of providing for transcription of genes in plant plastids are desired. Of particular interest is the use of a T7 promoter to provide for high levels of transcription. Since plastids do not contain an appropriate polymerase for transcription from the T7 promoter, T7 polymerase may be expressed from a nuclear construct and targeted to plastids using transit peptides as described above. (See McBride et al. (1994) *Proc. Nat. Acad. Sci.* 91:7301-7305; see also co-pending US patent application entitled "Controlled Expression of Transgenic Constructs in Plant Plastids", Ser. No. 08/472,719 filed Jun. 6, 1995, and co-pending U.S. patent application Ser. No. 08/167,638, filed Dec. 14, 1993 and PCT/US94/14574 filed Dec. 12, 1994.) Tissue specific or developmentally regulated promoters may be useful for expression of the T7 polymerase in order to limit expression to the appropriate tissue or stage of development. For example, for flower color modification, the T7 polymerase may be expressed from a petal specific promoter to limit effects to the desired tissue.

Targeting of melanin synthesis genes to vacuoles is also of interest in plant tissues which accumulate the tyrosine substrate involved in melanin synthesis in vacuoles. The protein signal for targeting to vacuoles may be provided from a plant gene which is normally transported across the rough endoplasmic reticulum, such as the 32 amino acid N-terminal region of the metallocarboxypeptidase inhibitor gene from tomato (Martineau et al. (1991) *Mol. Gen. Genet.* 228:281-286). In addition to the signal sequence, vacuolar targeting constructs also encode a vacuolar localization signal (VLS) positioned at the carboxy terminus of the encoded protein. Appropriate signal sequences and VLS regions may be obtained from various other plant genes and may be similarly used in the constructs of this invention. Numerous vacuolar targeting peptides are known to the art, as are reviewed in Chrispeels et al., *Cell* (1992) 68:613-616.

Thus, it is recognized that constructs of the instant invention which provide sequences encoding genes involved in color production and sequences which provide for targeting of the gene products to appropriate cellular locations have broad application to modification of color in various plant tissues. Plant transcriptional initiation regions for use with these color modification constructs will depend upon the particular plant tissue to be modified. For cotton fiber modification the 4-4 and rac13 cotton fiber promoters may find use.

Also of interest are genes involved in production of colored pigments in plant tissues. The Maize A1 gene which encodes a dihydroflavonol reductase, an enzyme of the anthocyanin pigmentation pathway is one such gene. In cells that express the A1 gene, dihydrokempferol is converted to 2-8 alkylleucopelargonidin, which may be further metabolized to pelargonidin pigment by endogenous plant enzymes. Other anthocyanin or flavonoid type pigments may also be of interest for modification of cotton cell fibers, and have been suggested for use in plant flowers (for a review of plant flower color, see van Tunen et al., *Plant Biotechnology Series*, Volume 2 (1990) *Developmental Regulation of Plant Gene Expression*, D. Grierson ed.). Anthocyanin is produced by a progression of steps from cellular phenylalanine pools. The R anc C1 genes are maize regulatory proteins which are active by positively affecting upstream steps in the anthocyanin biosynthesis from these pools. The R gene is described in Perot and Cone (1989) *Nucl. Acids Res.*, 17:8003, and the C1 gene is described in Paz-Ares et al. (1987) *EMBO*, 6:3553-3558. Lloyd et al. (1992) *Science*, 258:1773-1775 discussed both genes.

Although cotton fibers in commercially grown varieties are primarily white in color, other naturally occurring cotton varieties have brown or reddish-brown fibers. Also a cotton line containing green colored fibers has been identified. The existence of these colored cotton lines suggests that the precursors required for the anthocyanin pigment pathways are present in cotton fibers cells, thus allowing further color phenotype modifications. Thus, the maize R and C1 genes could be used in enhancing the levels of of anthocyanin produced in fiber cells. As the R and C1 proteins are proteins with a positive control at the regulatory level on anthocyanin pigment precursor biosynthesis, these proteins are expressed in the nucleus, and not targeted to plastids or vacuoles.

For some applications, it is of interest to modify other aspects of structures developing from the fiber integument and related structures. For example, it is of interest to modify various aspects of cotton fibers, such as strength or texture of a fiber. Thus, the appropriate gene may be inserted in the constructs of the invention, including genes for PHB biosynthesis (see, Peoples et al. *J. Biol. Chem.* (1989) 264: 15298-15303 and *Ibid.* 15293-15397; Saxena, *Plant Molecular Biology* (1990) 15:673-683, which discloses cloning and sequencing of the cellulose synthase catalytic subunit gene; and Bowen et al. *PNAS* (1992) 89:519-523 which discloses chitin synthase genes of *Saccharomyces cerevisiae* and *Candida albicans*. Various constructs and methods are disclosed for the use of hormones to effect changes to fiber quality in co-pending US patent application entitled "Cotton Modification Using Ovary-Tissue Transcriptional factors", Ser. No. 08/397,652 filed Feb. 2, 1995, the teachings of which are incorporated herein by reference.

Transcriptional cassettes may be used when the transcription of an anti-sense sequence is desired. When the expression of a polypeptide is desired, expression cassettes providing for transcription and translation of the DNA sequence of interest will be used. Various changes are of interest; these changes may include modulation (increase or decrease) of formation of particular saccharides, hormones, enzymes, or other biological parameters. These also include modifying the composition of the final fiber or fiber, that is changing the ratio and/or amounts of water, solids, fiber or sugars. Other phenotypic properties of interest for modification include response to stress, organisms, herbicides, brushing, growth regulators, and the like. These results can be achieved by providing for reduction of expression of one or more endogenous products, particularly an enzyme or cofactor, either by producing a transcription product which is complementary (anti-sense) to the transcription product of a native gene, so as to inhibit the maturation and/or expression of the transcription product, or by providing for expression of a gene, either endogenous or exogenous, to be associated with the development of a plant fiber.

The termination region which is employed in the expression cassette will be primarily one of convenience, since the termination regions appear to be relatively interchangeable. The termination region may be native with the transcriptional initiation region, may be native with the DNA sequence of interest, may be derived from another source. The termination region may be naturally occurring, or wholly or partially synthetic. Convenient termination regions are available from the Ti-plasmid of *A. tumefaciens*, such as the octopine synthase and nopaline synthase termination regions. In some embodiments, it may be desired to use the 3' termination region native to the cotton fiber transcription initiation region used in a particular construct.

As described herein, in some instances additional nucleotide sequences will be present in the constructs to provide for targeting of a particular gene product to specific cellular locations. For example, where coding sequences for synthesis of aromatic colored pigments are used in a construct, particularly coding sequences for enzymes which have as their substrates aromatic compounds such tyrosine and indole, it is preferable to include sequences which provide for delivery of the enzyme into plastids, such as an SSU transit peptide sequence. Also, for synthesis of pigments derived from tyrosine, such as melanin, targeting to the vacuole may provide for enhanced color modifications.

For melanin production, the tyrosinase and ORF438 genes from *Streptomyces antibioticus* (Berman et al. (1985) 37:101-110) are provided in cotton fiber cells for expression from a 4-4 and Rac13 promoter. In *Streptomyces*, the ORF438 and tyrosinase proteins are expressed from the same promoter region. For expression from constructs in a transgenic plant genome, the coding regions may be provided under the regulatory control of separate promoter regions. The promoter regions may be the same or different for the two genes. Alternatively, coordinate expression of the two genes from a single plant promoter may be desired. Constructs for expression of the tyrosinase and ORF438 gene products from 4-4 and rac promoter regions are described in detail in the following examples. Additional promoters may also be desired, for example plant viral promoters, such as CaMV 35S, can be used for constitutive expression of one of the desired gene products, with the other gene product being expressed in cotton fiber tissues from the 4-4 and rac promoter. In addition, the use of other plant promoters for expression of genes in cotton fibers is also considered, such as the *Brassica* seed promoters and the E6 gene promoter discussed above. Similarly, other constitutive promoters may also be useful in certain applications, for example the mas, Mac or DoubleMac, promoters described in U.S. Pat. No. 5,106,739 and by Comai et al., *Plant Mol. Biol.* (1990) 15:373-381. When plants comprising multiple gene constructs are desired, for example plants expressing the melanin genes, ORF438 and tyrosinase, the plants may be obtained by co-transformation with both constructs, or by transformation with individual constructs followed by plant breeding methods to obtain plants expressing both of the desired genes.

Color constructs which may find use in the methods of the instant application are described in co-pending US patent application to McBride et al., supra. Constructs for melanin and indigo expression are described therein, as well as results showing melanin expression in plant cells.

A variety of techniques are available and known to those skilled in the art for introduction of constructs into a plant cell host. These techniques include transfection with DNA employing *A. tumefaciens* or *A. rhizogenes* as the transfecting agent, protoplast fusion, injection, electroporation, particle acceleration, etc. For transformation with *Agrobacterium*, plasmids can be prepared in *E. coli* which contain DNA homologous with the Ti-plasmid, particularly T-DNA. The plasmid may or may not be capable of replication in *Agrobacterium*, that is, it may or may not have a broad spectrum prokaryotic replication system such as does, for example, pRK290, depending in part upon whether the transcription cassette is to be integrated into the Ti-plasmid or to be retained on an independent plasmid. The *Agrobacterium* host will contain a plasmid having the vir genes necessary for transfer of the T-DNA to the plant cell and may or may not have the complete TDNA. At least the right border and frequently both the right and left borders of the T-DNA of the Ti- or Ri-plasmids will be joined as flanking regions to the transcription construct. The use of T-DNA for transformation of plant cells has received extensive study and is amply described in EPA Serial No. 120,516, Hoekema, In: *The Binary Plant Vector System* (1985) Offset-drukkerij Kanters B. V., Alblasserdam, Chapter V, Knauf, et al., Genetic Analysis of Host Range Expression by *Agrobacterium*, In: *Molecular Genetics of the Bacteria-Plant Interaction*, Puhler, A. ed., Springer-Verlag, NY, 1983, p. 245, and An, et al., *EMBO J.* (1985) 4:277-284.

For infection, particle acceleration and electroporation, a disarmed Ti-plasmid lacking particularly the tumor genes found in the T-DNA region) may be introduced into the plant cell. By means of a helper plasmid, the construct may be transferred to the *A. tumefaciens* and the resulting transfected organism used for transfecting a plant cell; explants may be cultivated with transformed *A. tumefaciens* or *A. rhizogenes* to allow for transfer of the transcription cassette to the plant cells. Alternatively, to enhance integration into the plant genome, terminal repeats of transposons may be used as borders in conjunction with a transposase. In this situation, expression of the transposase should be inducible, so that once the transcription construct is integrated into the genome, it should be integrated in a relatively stable manner. Transgenic plant cells are then placed in an appropriate selective medium for selection of transgenic cells which are then grown to callus, shoots grown and plantlets generated from the shoot by growing in rooting medium.

To confirm the presence of the transgenes in transgenic cells and plants, a Southern blot analysis can be performed using methods known to those skilled in the art. Expression products of the transgenes can be detected in any of a variety of ways, depending upon the nature of the product, and include immune assay, enzyme assay or visual inspection, for example to detect pigment formation in the appropriate plant part or cells. Once transgenic plants have been obtained, they may be grown to produce fiber having the desired phenotype. The fiber or fiber parts, such as cotton fibers may be harvested, and/or the seed collected. The seed may serve as a source for growing additional plants having the desired characteristics. The terms transgenic plants and transgenic cells include plants and cells derived from either transgenic plants or transgenic cells.

The various sequences provided herein may be used as molecular probes for the isolation of other sequences which may be useful in the present invention, for example, to obtain related transcriptional initiation regions from the same or different plant sources. Related transcriptional initiation regions obtainable from the sequences provided in this invention will show at least about 60% homology, and more preferred regions will demonstrate an even greater percentage of homology with the probes. Of particular importance is the ability to obtain related transcription initiation control regions having the timing and tissue parameters described herein. For example, using the probe 4-4 and rac, at least 7 additional clones have been identified, but not further characterized. Thus, by employing the techniques described in this application, and other techniques known in the art (such as Maniatis, et al., *Molecular Cloning,—A Laboratory Manual* (Cold Spring Harbor, N.Y.) 1982), other transcription initiation regions capable of directing cotton fiber transcription as described in this invention may be determined. The constructs can also be used in conjunction with plant regeneration systems to obtain plant cells and plants; the constructs may also be used to modify the phenotype of a fiber and fibers produced thereby.

Various varieties and lines of cotton may find use in the described methods. Cultivated cotton species include *Gossypium hirsutum* and *G. babadense* (extra-long stable, or Pima cotton), which evolved in the New World, and the Old World crops *G. herbaceum* and *G. arboreum*.

Color phenotypes can be assessed by the use of a colorimeter, an instrument which is already used to provide objective measurements of the color of cotton samples. A colorimeter uses a combination of light sources and filters to make various estimates of samples of colors, sometimes referred to as tristimulus values.

In the past such estimates have been used to calculate a value (Hunter's +b, described below) indicating the degree of yellowness of a cotton sample. The yellowness and reflectance (from Rd, the degree of lightness of darkness of the samples) has been used to provide cotton color measurements for grading. Tests are typically conducted by exposing the face of a sample to a controlled light source. A typical color chart showing how the official grade standards relate to Rd and +b measurements is shown in *Cotton*, R J Kohel and C F Lewis, Eds., #24 in AGRONOMY Series-American Soc. Agronomy (see FIG. 12-6 therein).

Various colorimeter methods can be so used to quantify color and express it numerically. The Munsell method, devised by the American artist A. Munsell, uses a classification system of paper color chips assorted according to their hue (Munsell Hue), lightness (Munsell Value), and saturation (Munsell Chroma) for visual comparison with a specimen color.

Other methods for expressing color numerically have been developed by an international organization concerned with light and color, the Commission Internationale de l'Eclairage (CIE), having a Central Bureau located at Kegelgasse 27, A-1030 Vienna, Austria. The two most widely known of these methods are the Yxy color space, devised in 1931 based on the tristimulus value XYZ, as defined by CIE, and the L*a*b* color space, devised in 1976 to provide more uniform color differences in relation to visual differences. Color spaces* such as these are now used throughout the world for color communication. The Hunter Lab color space was developed in 1948 by R. S. Hunter as a uniform color space which could be read directly from a photoelectric colorimeter (tristimulus method).

The L*C*h color space uses the same diagram as the L*a*b* color space, but uses cylindrical coordinates instead of rectangular coordinates. In this color space, L* indicates lightness and is the same as the L* of the L*a*b* color space, C* is chroma, and h is the hue angle. The value of chroma C is 0 at the center and increases according to the distance from the center. Hue angle is defined as starting at the +a axis of the L*a*b* space, and is expressed in degrees in a counterclockwise rotation. Thus, relative to the L*a*b* space, 0° and 360° would be at the +a* line, 90° would be the +b*, 180° would be −a* and 270° would be −b*. All of the above methods can be used to obtain precise measurements of a cotton fiber color phenotype.

The following examples are offered by way of illustration and not by limitation.

EXPERIMENTAL

Example 1 cDNA Libraries

Tissue Preparation for cDNA Synthesis

Leaf and root tissue were isolated from 8 inch tall greenhouse grown seedlings and immediately frozen in liquid nitrogen. Flowers were collected at the rapidly expanding 3 day pre-anthesis stage and also frozen. Seed was collected from 21 day post-anthesis locules which had been removed from the boll and frozen entire in liquid nitrogen. Once frozen, the fiber was removed from the seed and the denuded seed used for RNA isolation. All fibers were removed from the seed under liquid nitrogen and the fiber was ground to a powder prior to RNA isolation. Fibers were from bolls which had been tagged at anthesis.

DNA and RNA Manipulations

The λZapII cDNA library used for screening was prepared from cDNA derived from poly-$A^+$ mRNA isolated from fibers of *Gossypium hirsutum* cultivar Acala SJ-2. The fibers were isolated from bolls harvested at approximately 21 dpa using field-grown plants in Israel.

Total RNA was isolated from 21 dpa seeds (*G. hirsutum* cv Coker 130 from which the fiber had been removed) using the method of Hughes and Galau ((1988) *Plant Mol. Biol. Reporter*, 6:253-257.) All other RNAs were prepared according to Hall et al. ((1978), *Proc. Natl. Acad. Sci. USA* 75: 3196-3200), with the following modifications. After the second 2M LiCl wash, the pellet was dissolved in 1/10 original volume of 10 mM Tris pH7.5 and brought to 35 mM potassium acetate pH6.5 and ½ volume EtOH was added slowly. The mixture was placed on ice for 15 minutes and then centrifuged at 20,000×g for 15 minutes at 4° C. The potassium acetate concentration was brought to 0.2M, 2½ volumes EtOH added and the RNA placed at −20° C. for several hours. The precipitate was centrifuged at 12,000×g for 30 minutes at 4° C. and the pellet was resuspended in diethylpyrocarbonate-treated water. Poly-$A^+$ RNA was prepared from total mRNA utilizing an oligo(dT)-cellulose kit (Becton Dickenson) and following the manufacturer's protocol.

Cotton genomic DNA was prepared as follows. Four grams of young cotton leaf tissue (cv Coker 130) was ground to a powder in $N_2$ and placed in an Oak Ridge tube with 0.4 g polyvinylpyrolidone and 20 ml extraction buffer (200 mM Ches/NaOH pH9.1, 200 mM NaCl, 100 mM EDTA/NaOH pH9.0, 2% SDS, 0.5% Na deoxycholate, 2% Nonidet NP-40, 20 mM B-mercaptoethanol) was added to sample, gently mixed and incubated at 65° C. in a shaking water bath for 10 minutes. 7.0 ml of 5M potassium acetate pH6.5 was added and carefully mixed. Incubation was carried out on ice for 30 minutes with gentle mixing every 5 minutes. The sample was centrifuged for 20 minutes at 21,000×g and the supernatant was filtered through Miracloth into another tube and centrifuged as before. The supernatant was again filtered through Miracloth into 15 ml of room temperature isopropanol in an Oak Ridge tube. After gentle mixing, the sample was incubated at room temperature for 10-60 minutes until the DNA precipitated. The DNA was spooled and allowed to air dry before being resuspended in 4 mls of TE on ice for 1 hour. CsCl was added to 0.97 g/ml final concentration and 300 ul 10 mg/ml ethidium bromide was also added before filling VTi80 quick seal tubes. The sample was centrifuged overnight at 225,000×g overnight. The DNA was extracted with water saturated butanol and enough water was added to bring the volume to 4 mls before adding 2 volumes EtOH. The DNA was spooled, air dried and resuspended in 200 ul sterile water.

Northern and Southern Analysis

For Northerns, 10 ug of total RNA was isolated from various tissues, separated by electrophoresis in 1.2% agarose-formaldehyde gels and transfered onto Nytran Plus membranes (Schleicher and Schuell). Hybridization conditions consisted of a solution containing 50% formamide(v/v), 5×SSC, 0.1% SDS, 5 mM EDTA, 10× Derihardts solution, 25 mM sodium phosphate pH6.5 and 250 ug/ml carrier DNA. Washes were performed in 2×SSC, 0.1% SDS at 42° C. 3 times for 30 minutes each time.

Cotton genomic DNA (12 ug) was digested with various restriction endonucleases, electrophoresed in 0.9% agarose gels and blotted onto Nytran Plus membranes. Hybridization and filter washing conditions for both the 3' specific and full-length cDNA insert probes were as described for Northern analysis.

Probes derived from 3'-untranslated regions were synthesized via oligonucleotide primers from the Rac13 cDNA, corresponding to bases 600-619 and 843-864 (FIG. 4) (SEQ ID NO: 12). Each set of primers was used in a polymerase chain reaction to synthesize copies of 3'-specific DNA sequences. These sequences were used as templates in the generation of single-stranded, $^{32}$P-labeled probes off the antisense strand in a polymerase chain reaction. The full-length cDNA inserts for Rac13 were used as templates for double stranded, random primed probes using the Prime-It kit (Stratagene).

Example 2

Isolation of cDNA Clones from Cotton cDNA to the 4-4 clone was isolated from the cotton fiber library described above, and shown to express in fiber but not other tissues. This sequence was not related to any known protein. Only 400 kb of encoding sequence was present in this clone, so the library was rescreened using the cDNA to obtain full-length clones. The full-length encoding sequence is provided in FIG. 1 (SEQ ID NO: 1).

Another clone was sequenced which showed high homology to animal Rac proteins. This clone, designated Rac13, was not quite full-length, and the library was re-screened using this initial Rac13 DNA segment as probe. Of approximately 130,000 primary plaques screened, 56 screened positive; of these, 14 clones were isolated and sequenced. Of these 14 clones, 12 showed identical sequence homology to the original Rac13 clone and one of these cDNA clones encoded a full length Rac13. One other partial-length cDNA clone, designated Rac9, was clearly related, but distinct in DNA and amino acid sequence from Rac13. Re-screening of 150,000 plaques resulted in the isolation of 36 positive clones of which only two clones corresponded to the Rac9 sequence (both full-length clones), the remainder being Rac13. These results suggest that cotton contains genes for at least two distinct Rac proteins. Based upon the frequency of clone isolation, Rac13 is relatively highly-expressed and Rac9 less so in cotton fibers at 21 days post-anthesis (dpa), the age at which polyA$^+$ mRNA was isolated for library construction.

FIG. 4 (SEQ ID NO: 13) shows the DNA (SEQ ID NO: 12) and deduced amino acid (SEQ ID NO: 14) sequences for Rac13 full length. Comparisons of the deduced amino acid sequence of Rac13 with other small G-proteins showed that the cotton Rac proteins are very closely related to the Rho1 protein sequence deduced from a cDNA clone isolated recently from pea (Yang and Watson, supra). After the pea Rho1, mammalian Rac proteins show the highest homology with the cotton Rac proteins. Other proteins of the rho subfamily, such as the yeast CDC42 and human RhoA, are also clearly related to the cotton Rac genes. By contrast, the other small G-proteins of the Rab/YPT subfamily isolated from plants such as the example shown of the tobacco RAB5 protein, as well as the human Ras proteins, are least homologous to the cotton Rac proteins of all the small G-proteins compared. The cotton and pea proteins, as well as the mammalian Racs, all have pI's above 9, whereas those of other rho and ras proteins are in the range of 5.0-6.5.

Example 3

Expression of Cotton Fiber Genes in Developing Fibers

Expression of the Rac13 and 4-4 genes was assessed using mRNA prepared from various cotton tissues and from fibers at different stages of development. Blots were hybridized with probes derived from 3'-untranslated regions of either the Rac13 or 4-4 genes. The gene for Rac13 exhibits highly-enhanced expression in fibers; virtually no detectable mRNA is present in leaves, roots, or flower parts, even under conditions of extended development time. Rac13 expression is detected in seeds at an age that corresponds to the highest expression levels observed in fiber tissue derived from seeds of this same age. The pattern of Rac13 expression in fibers is very dependent upon the developmental stage. Expression is very low during the stage of primary wall synthesis (0-14 dpa, see Meinert and Delmer, 1977), reaches a maximum during the transition to secondary wall synthesis (about 15-18 dpa), and declining during the stage of maximal secondary wall cellulose synthesis (about 24-28 dpa).

4-4 mRNA is begins to accumulate in fiber cells only at day 17 post anthesis and continues through fiber maturity at day 35 post anthesis. Levels peak at day 21 and remain high throughout fiber maturation to 35 days post anthesis. 4-4 mRNA is not detected in other cotton tissues, and is not detected in fiber tissue before onset at 17 days post anthesis.

The #105 lipid transfer protein cDNA clone was used as a probe against cotton tissue and in a cotton fiber northern. The northern showed that the cotton fiber Ltp is highly expressed in cotton fiber. The mRNA that codes for this protein is expressed throughout fiber development at extremely high levels. Northern blots indicate that this mRNA is expressed at 5 dpa and is continually expressed at a high level at 40 dpa.

Example 4

Genomic DNA cDNA for both the 4-4 and Rac13 was used to probe for genomic clones. For both, full length genomic DNA was obtained from a library made using the lambda dash 2 vector from Stratagene™, which was used to construct a genomic DNA library from cotton variety Coker 130 (Gossypium hirsutum cv. coker 130), using DNA obtained from germinating seedlings.

The cotton genomic library was probed with a 3'-specific Ltp probe and 6 genomic phage candidates were identified and purified. FIG. 7 provides an approximately 2 kb sequence of the Ltp promoter region which is immediately 5' to the Ltp encoding region.

Six genomic phage clones from the cotton genomic library were identified using a 3'-specific probe for the Ltp mRNA. This was done to select the promoter from the Ltp gene that is maximally expressed in cotton fiber from the family of Ltp genes in cotton. The Ltp promoter is active throughout the fiber development period.

Example 5

Preparation of 4-4 Promoter Constructs pCGN5606
The pCGN5606 promoter construct comprises the 4-4 cotton fiber expression cassette in a first version, version I (FIG. 2) (SEQ ID NO: 7). The sequences from nt1 to 65 and nt 5,494 to 5,547 correspond to fragments of the pBluescriptII polylinker where this cassette is cloned. Unique restriction enzyme sites present in these regions flanking the cassette allow the cloning of the fiber expression cassette into binary vectors including the pCGN 5138 and 1547 series.

The sequences from nt57 to 5,494 are contained in a lambda phage clone of a cotton Coker 130 genomic library. This clone is lambda genomic clone 4-4(6).

The region from nt 65 to nt 4,163 corresponds to the 5' flanking region of the 4-4(6) gene. At nt 4,163 there is a NcoI restriction site sequence that corresponds to the first codon of the 4-4 (6)ORF (see SEQ ID NO: 8-10).

The region from nucleotide 4,163 to 4,502 corresponds to part of the 4-4 (6)ORF. The sequence from nt 4,502 to 4,555 is a synthetic polylinker oligonucleotide that contains unique target sites for the restriction enzymes EcoRI, SmaI, SalI, NheI and BglII. This fragment from nt4,163 to 4,555 is a stuffer fragment and is left in place to facilitate the monitoring of cloning manipulations.

The genes to be expressed in cotton fiber cells using this cassette can be cloned between the NcoI restriction site and any of the polylinker sites. This operation will replace the stuffer fragment with the gene of interest. The region from nt 4,555 to 5,494 corresponds to the 940 nucleotides downstream of the stop codon and constitute the 3' flanking region of the 4-4 (6) gene. There is a unique AscI restriction enzyme site at nt 5483.

pCGN5610

The pCGN5610 construct is a second version of a 4-4 cotton fiber expression cassette, version II, which is a modified version of pCGN5606. The two versions of the 4-4 cotton fiber expression cassette are designed to allow the cloning of tandem arrays of two fiber cassettes in one binary plasmid. The differences with respect to pCGN5606 are very minor and described below.

The XbaI restriction site in the region of nt 1 to 65 has been deleted by standard cloning manipulations. The polylinker region is in the reverse orientation of pCGN5606. There is a unique XbaI restriction enzyme site at nt5484. The sequences from nt1 to 57 and nt 5,494 to 5,518 of pCGN5610 correspond to fragments of the pBluescriptII polylinker where this cassette is cloned. Unique restriction enzyme sites present in these regions allow the cloning of the fiber expression cassette into binary vectors of the pCGN 5138 and 1547 series.

The sequences from nt57 to 5,494 are contained a lambda phage clone of a Coker 130 genomic library. This clone was designated lambda genomic clone 4-4(6). The region from nt 57 to nt 4,155 corresponds to the 5' flanking region. At nt 4,155 there is a NcoI restriction site sequence that corresponds to the first codon of the 4-4 ORF. The region from nucleotide 4,156 to 4,500 corresponds to part of the 4-4 ORF. This fragment from nt4,156 to 4,550 is a stuffer fragment and is left in place to facilitate the monitoring of cloning manipulations. The sequence from nt 4,500 to 4,550 is a synthetic polylinker oligonucleotide containing unique target sites for the restriction enzymes BglII, NheI, SalI, SmaI and EcoRI.

The genes to be expressed in cotton fiber cells using this cassette can be cloned between the NcoI restriction site and any of the polylinker sites. This operation will replace the stuffer fragment with the gene of interest. The region from nt 4,550 to 5,494 corresponds to the 940 nucleotides downstream of the stop codon and constitute the 3' flanking region of the 4-4 (6) gene.

Example 6

Preparation of Rac13 Promoter Constructs

Genomic Clone

From a genomic clone designated 15-1, mapping was done with restriction endonucleases. The largest fragment with the Rac13 coding region was identified. This was a Pst fragment, and when subcloned in the Bluescript™ KS+ vector (BSKS+; Stratagene) was named pCGN4722. The insert had a length of 9.2 kb.

The region of the Pst fragment with the Rac13 coding sequence was identified. DNA sequence was determined for approximately 1.7 kb 5' of the start codon and approximately 1.2 kb 3' of the stop codon. The entire Rac coding region (exons and introns) was conveniently flanked by Nde1 sites.

pCGN4722 was digested with Xba1, and a 2.7 kb fragment was removed. Re-ligation gave pCGN4730, which was then digested with Nde1, dropping out a 1.7 kb fragment containing the entire Rac coding region. Re-ligation yielded pCGN4731.

A polylinker region was created using overlapping synthetic oligonucleotides which were PCR amplified using primers homologous to the 5' and 3' ends of the resynthesized section. The resulting product was digested with EcoR1 and Hind III and ligated into BSKS+ at eht EcoR1 and Hind III sites. The resulting plasmid was designated pCGN4733.

pCGN4731 and pCGN4633 were digested with Nde1 and the Nde1 fragment containing the synthesized polylinker region from pCGN4733 was dropped in the Nde1 site of 4731, giving pCGN4734. This last plasmid was digested with Sal and Xba, and so was pCGN5133. pCGN5133 was the 9.2 kb pst fragment in BSKS+ where the polylinker sites flanking the insert were altered to different sites for ease of manipulation. The fragment from 4734 was then placed into the equivalent site of pCGN5143, giving pCGN4735.

A sequence for approximately 3 kb of the promoter construct pCGN4735 is provided in FIG. 5 (SEQ ID NO: 15). The resynthesized sequence falls between the Nde1 sites located at bases 1706 and 1898 of the sequences. Thus, the sequence in FIG. 5 includes approximately 1.7 kb 5' to the Nde1 site 5' to the resynthesized polylinker region. There is a roughly 2.5 kb sequence 5' from this sequence which is not provided in FIG. 5, relative to the total 9.2 kb insert. The sequence of FIG. 5 also includes approximately 1.1 kb 3' to the 3' Nde1 site. Approximately 3 kb which is most 3' in the Rac13 insert is not provided in FIG. 5. A map for pCGN4735 is provided in FIG. 6.

Example 7

Constructs for Pigment Synthesis Genes

Constructs which contain encoding sequences for plant or bacterial genes involved in biosynthesis of pigmented compounds, as well as sequences for directing transport of the encoded proteins into plastids or vacuoles are described in co-pending US patent application to McBride et al., entitled "Use of Ovary Tissue Transcriptional Factors", Ser. No. 08/480,178 filed on Jun. 7, 1995, the teachings of which are incorporated herein by reference. The targeting sequences are manipulated to be present on an NcoI/EcoRI fragment and may easily introduced into the 4-4 and rac transcriptional initiation regions for providing transcription in cotton fibers.

Melanin

A binary construct for plant transformation to express genes for melanin synthesis is prepared as follows. The melanin genes were originally isolated from the common soil bacterium *Streptomyces antibioticus* (Bernan, et al. *Gene* (1985) 37:101-110). Melanin production is composed of a two gene system. The first gene, tyrA, encodes the catalytic unit responsible for the polymerization of the amino acid tyrosine, the primary substrate, and is termed tyrosinase. The second gene, ORF438, is responsible for binding copper and delivering copper to the tyrosinase and activating the enzyme. Expression of both the ORF438 and tyrA genes ensures maximal tyrosinase activity.

The genes for both ORF438 and tyrA were fully re-synthesized with respect to their DNA sequence. This was performed as the initial DNA sequence isolated from *Streptomyces* has a very high guanine and cytosine (G+C) DNA content. Thus, the ORF438 and tyrA genes were re-synthesized to appear more "plant-like" (reduced G+C content) with respect to plant preferred codons encoding their corresponding amino acids.

The re-synthesized ORF438 and tyrA genes were treated in two distinct ways depending on which compartment in the fiber cell the final protein products would be localized. One chimeric gene/plant binary construct (designated pCGN5148) contained the genes targeted to the fiber cell plastids. To do this, 12 amino acids of a gene for the small subunit of carboxylase (SSU) plus the original 54 amino acid SSU transit peptide were fused to the amino termini of both the ORF438 and tyrA gene products respectively. These peptide sequences allow the ORF438 and tyrA gene products (proteins) to be efficiently targeted to the plastid. This targeting was initiated as the plastid is the site of tyrosine production within the fiber cell.

The second chimeric gene/plant binary construct (designated pCGN5149) contained the ORF438 and tyrA genes targeted to the vacuole within the fiber cell. Based on information from other biological systems, it was postulated that the fiber cell vacuole may contain a high concentration of tyrosine for melanin polymerization. Both the ORF438 and tyrA genes contain the 29 amino acid signal peptide from a tomato carboxypeptidase inhibitor (CPI) protein as amino terminal gene fusions to direct these proteins to the endoplasmic reticulum (ER) secretory system of the fiber cell.

In addition, the tyrA gene has an 8 amino acid vacuolar targeting peptide (VTP) from CPI fused at the carboxy terminus so that the mature copper-activated tyrosinase will eventually be targeted to the vacuole of the fiber cell. Both the ORF438 and tyrA proteins also had potential glycosylation sites removed via site-directed mutagenesis of the ORF438 and tyrA genes, respectively. Potential plant cell glycosylation of these proteins upon their expression in fiber cells could result in tyrosinase inactivation, hence removal of potential glycosylation sites was deemed necessary.

The modified genes for both the plastid and vacuolar targeted ORF438 and tyrosinase proteins were placed into a fiber expression cassette to be "switched" on during development of the cotton fiber cell. The "switch" (promoter) utilized for the melanin constructs was 4-4. The modified ORF438 and tyrA genes were cloned into the 4-4 promoter cassette and these chimeric genes then inserted into a binary plasmid to create plasmids pCGN5148 and pCGN5149, containing the modified genes for plastid and vacuolar targeted ORF438 and tyrosinase proteins, respectively. These binary plasmids also contain genetic determinants for their stable maintenance in *E. coli* and *Agrobacterium* and also contain a chimeric gene for plant cell expression of the bacterial kanamycin resistance gene. This kanamycin resistance marker allows for the selection of transformed versus non-transformed cotton cells when plant hypocotyl or leaf segments are infected with *Agrobacterium* containing the binary plasmids.

Figure 8:
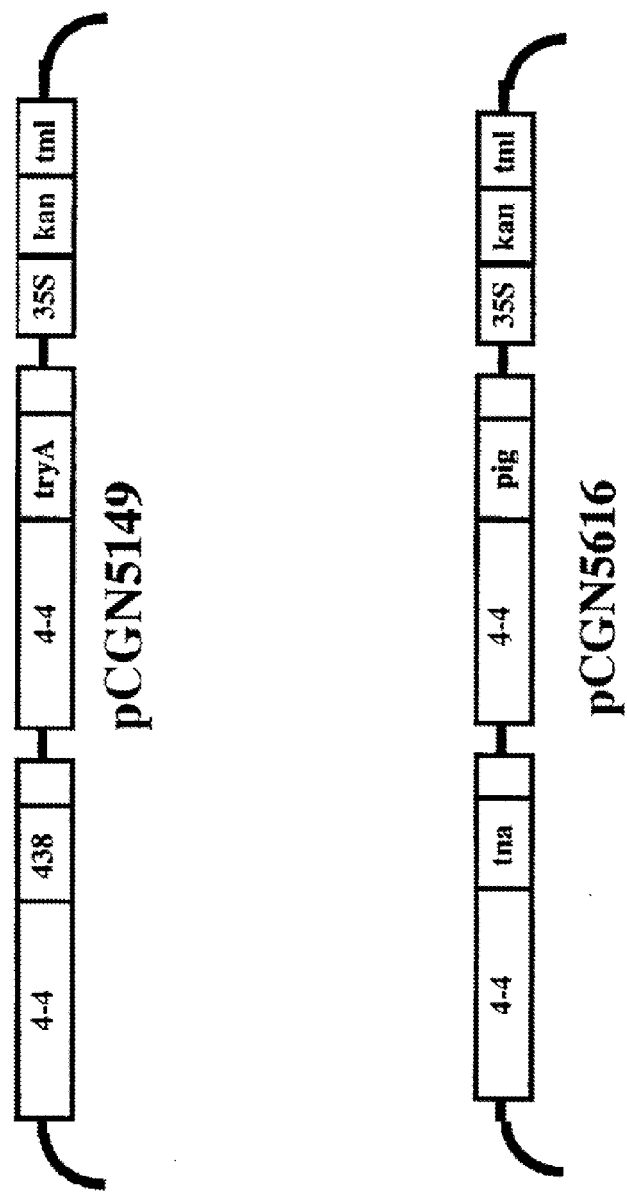
FIG. 8 shows the arrangement of binary vectors, pCGB5149 and pCGN5616 for plant transformation to express genes for melanin synthesis and indigo synthesis, respectively.

A block diagram of the plasmid pCGN5149, having vacuolor targeting sequences, is shown in FIG. 8. Plasmid pCGN5148 (not shown) is constructed the same as pCGN5149; only pCGN5148 has plastid-targeting sequences.

Indigo

Indigo production involves conversion of the amino acid tryptophan, the primary substrate, into indole which is then converted into indoxyl. Molecules of indoxyl spontaneously convert to indigo in the presence of oxygen. A two gene system was used to effect indigo production in fiber cells. The first gene (tna) was obtained from the bacterium *E. coli* and encodes the enzyme tryptophanase. The designation tna stands for the gene encoding tryptophanase from *E. coli*, an enzyme which converts tryptophan to indole (Stewart et al., *J. Bacteriol.* (1986) 166:217-223).

The pig designation is used for the encoding sequence for the protein for indigo production from *Rhodococcus*, which produces indigo from indole (Hart et al., *J. Gen. Microbiol.* (1990) 136:1357-1363). Both tna and pig were obtained by PCR. Tryptophanase is responsible for the conversion of tryptophan to indole, while the second gene (pig) encodes an indole oxygenase enzyme responsible for the conversion of indole to indoxyl. Both these bacterial genes were utilized in their native form.

The tobacco SSU transit peptide encoding DNA sequences were fused onto the amino terminal region of both the tna and pig indigo genes to effect localization of both the tryptophanase and indole oxygenase proteins to the fiber cell plastid. These are the same exact gene fusions that were made for the plastid-directed proteins for melanin production in construct 5148. The tna and pig gene products were targeted to the fiber cell plastid as that is the primary site of tryptophan synthesis.

As with the melanin genes, the plastid-directed tna and pig genes were placed in the fiber-specific 4-4 promoter cassette and these chimeric genes were subsequently inserted into a binary plasmid to create plasmid pCGN5616. A block diagram of plasmid pCGN5616 is shown in FIG. 8.

Example 8

Cotton Transformation

Explant Preparation

Coker 315 seeds are surface disinfected by placing in 50% Clorox (2.5% sodium hypochlorite solution) for 20 minutes and rinsing 3 times in sterile distilled water. Following surface sterilization, seeds are germinated in 25×150 sterile tubes containing 25 mls ½×MS salts: ½×B$_5$ vitamins: 1.5% glucose: 0.3% gelrite. Seedlings are germinated in the dark at 28° C. for 7 days. On the seventh day seedlings are placed in the light at 28±2° C.

Co-cultivation and Plant Regeneration

Single colonies of *A. tumefaciens* strain 2760 containing binary plasmids pCGN2917 and pCGN2926 are transferred to 5 ml of MG/L broth and grown overnight at 30° C. Bacteria cultures are diluted to 1×10$^8$ cells/ml with MG/L just prior to cocultivation. Hypocotyls are excised from eight day old seedlings, cut into 0.5-0.7 cm sections and placed onto tobacco feeder plates (Horsch et al. (1985) *Cold Spring Harb. Symp. Quant. Biol.* 50: 433-437.). Feeder plates are prepared one day before use by plating 1.0 ml tobacco suspension culture onto a petri plate containing Callus Initiation Medium (CIM) without antibiotics (MS salts: B$_5$ vitamins: 3% glucose: 0.1 mg/L 2,4-D: 0.1 mg/L kinetin: 0.3% gelrite, pH adjusted to 5.8 prior to autoclaving). A sterile filter paper disc (Whatman #1) was placed on top of the feeder cells prior to use. After all sections are prepared, each section was dipped into an *A. tumefaciens* culture, blotted on sterile paper towels and returned to the tobacco feeder plates.

Following two days of co-cultivation on the feeder plates, hypocotyl sections are placed on fresh Callus Initiation Medium containing 75 mg/L kanamycin and 500 mg/L carbenicillin. Tissue was incubated at 28±2° C., 30 μE m$^{-2}$s$^{-1}$ 16:8 light:dark period for 4 weeks. At four weeks the entire explant was transferred to fresh callus initiation medium containing antibiotics. After two weeks on the second pass, the callus was removed from the explants and split between Callus Initiation Medium and Regeneration Medium (MS salts: 40 mM KNO$_3$: 10 mM NH$_4$Cl: B$_5$ vitamins: 3% glucose: 0.3% gelrite: 400 mg/L carbenicillin: 75 mg/L kanamycin).

Embryogenic callus was identified 2-6 months following initiation and was subcultured onto fresh regeneration medium. Embryos are selected for germination, placed in static liquid Embryo Pulsing Medium (Stewart and Hsu medium: 0.01 mg/1 NAA: 0.01 mg/L kinetin: 0.2 mg/L GA3) and incubated overnight at 30° C. The embryos are blotted on paper towels and placed into Magenta boxes containing 40 mls of Stewart and Hsu medium solidified with Gelrite. Germinating embryos are maintained at 28±2° C. 50 uE m$^{-2}$s$^{-1}$ 16:8 photoperiod. Rooted plantlets are transferred to soil and established in the greenhouse.

Cotton growth conditions in growth chambers are as follows: 16 hour photoperiod, temperature of approximately 80-85° F., light intensity of approximately 500 µEinsteins. Cotton growth conditions in greenhouses are as follows: 14-16 hour photoperiod with light intensity of at least 400 µEinsteins, day temperature 90-95° F., night temperature 70-75° F., relative humidity to approximately 80%.

Plant Analysis

Flowers from greenhouse grown T1 plants are tagged at anthesis in the greenhouse. Squares (cotton flower buds), flowers, bolls etc. are harvested from these plants at various stages of development and assayed for enzyme activity. GUS fluorometric and histochemical assays are performed on hand cut sections as described in co-pending application filed for Martineau et al., supra. For fiber color characteristics, plants are visually inspected, or northern or western analysis can be performed, if necessary.

As shown by the above results, expression of a gene of interest can be obtained in cells derived from fiber cells, including tomato fiber and cotton fibers, and expression of genes involved in synthesis of pigments combined with appropriate targeting sequences results in modification of color phenotype in the selected plant tissue.

All publications and patent applications cited in this specification are herein incorporated by reference as if each individual publication or patent application are specifically and individually indicated to be incorporated by reference.

Example 9

Expression of Transgenic Pigment Synthesis Genes

Melanin

Plants that exhibited resistance to the kanamycin selectable marker via a leaf assay and corresponding Western analysis were considered transformed. Transgenic fiber was collected from individual plant transformants at different stages of fiber development and analyzed in two ways. One was to analyze fiber at a single developmental time point for each transgenic cotton plant to compare tyrosinase expression between transgenic events. The other was to screen developing fiber from selected plants to analyze the timing of tyrosinase expression under the control of the fiber-specific 4-4, by the Western blots using antisera prepared against purified tyrosinase protein.

For the plastid-targeted construct pCGN5148, 9 of 13 events screened for tyrosinase expression were positive, while 13 of the 16 transformed vacuolar-targeted construct pCGN5149 events which were screened were positive. Expression level in the fiber in tyrosinase positive plants is approximately 0.1-0.5% fiber cell protein. Clearly, the cotton fiber cells comprising the DNA color constructs DNA produce the necessary proteins required for synthesis of a pigment.

Visually, the lint from the tyrosinase positive events exhibits color to varying degrees, while plants that do not express the enzyme do not exhibit any color. Colorimeter measurements of cotton fiber taken from control Coker 130 plants and plants from various events transformed with pCGN5148 are provided in FIGS. 9 and 10, respectively.

Fiber from pCGN5148 (plastid-directed) plants demonstrates a bluish-green color phenotype. One event, 5148-50-2-1 included cotton fiber cells (linters) which were colored and which had a negative a* value of less than −8.0, as measured on the L*a*b* color space. Coker 130 cotton fiber cells do not typically demonstrate a negative a* value.

These colored cotton cells also had a color located on the L*C*h* color space with a relatively high hue angle value, h, of greater than 135° . Normal Coker 130 fibers have a similar value which is not greater than about 90° as measured by this method.

Results of colorimeter measurements of cotton fiber taken from plants transformed with pCGN5149 are provided in FIG. 11. Fiber from plants expressing tyrosinase from construct pCGN5149 (vacuolar-targeted) tends to have a light brown phenotype.

Indigo

Resistance to the kanamycin selectable marker via leaf assay and Western analysis was again the criterion for designating a plant as transformed by pCGN5616. Transgenic fiber was collected from individual plant transformants at different stages of fiber development. The transgenic developing fiber is screened from selected plants to analyze the timing of tna and pig gene expression under the control of the fiber-specific 4-4 promoter and fiber is also analyzed at a single developmental time point for each transgenic cotton plant for comparison of both tryptophanase and indole oxygenase expression between transgenic events, by using Western blots with antisera prepared against the tryptophanase and indole oxygenase proteins.

For the indigo events, 15 of 24 screened plants were positive for expression of both the tryptophanase and indole oxygenase enzymes. Expression levels in the fiber of these proteins is between 0.05-0.5% fiber cell protein. Approximately half of these transformants are expressing both genes in the fiber resulting in a very faint light blue color phenotype. Visually, there is a faint blue color in the majority of these positive events, particularly in 20-30 dpa fiber in the unopened boll. Results of colorimeter measurements of cotton fiber taken from various events of plants transformed with pCGN5616 are provided in FIG. 12. Many of these events had relatively low a* values (less than 2) with elevated b* values (greater than 10), as measured on the L*a*b* color space. Similarly, several 5149 also measured with an a* value less than 2 while maintaining a b* value greater than 10.

BC Cotton

Colorimeter measurements taken on naturally colored fiber from four separate BC cotton lines is provided in FIG. 13.

The above results demonstrate that the color phenotype of a transgenic cotton fiber cell can be altered by expressing pigment synthesis genes. The transgenic cotton fiber cells include both a pigment synthesizing protein, and pigment produced by the pigment synthesizing protein. As shown from the results of FIGS. 9 through 13, expression of a pigment gene of interest can result in cotton fiber cells in which the synthesis of pigments combined with appropriate targeting sequences results in modification of color phenotype in the selected plant tissue, yielding colored cotton fiber by expression from a genetically engineered construct.

Although the foregoing invention has been described in some detail, by way of illustration and example for purposes of clarity and understanding, it will be readily apparent to those of ordinary skill in the art that certain changes and modifications may be made thereto, without departing from the spirit or scope of the appended claims.

The invention claimed is:

1. A recombinant DNA sequence comprising as operably joined components in the direction of transcription, a cotton fiber transcriptional initiation region functional in a cotton fiber cell and an open reading frame encoding an enzyme in a pigment biosynthesis pathway, wherein said transcriptional initiation region is selected from the group consisting of:
   a. nucleotides 65-4163 of SEQ ID NO:7, and
   b. SEQ ID NO:15.

2. The DNA sequence according to claim 1, further comprising a sequence encoding a transit peptide from a plant nuclear-encoded gene.

3. The DNA sequence according to claim 2, wherein said transit peptide is a plastid transit peptide.

4. The DNA sequence according to claim 1, wherein said DNA sequence further comprises as an operably joined component a sequence encoding a signal peptide which provides for transport across the rough endoplasmic reticulum.

5. The DNA sequence according to claim 4, wherein said DNA sequence further comprises as an operably joined component, 3' to said open reading frame, a sequence encoding a vacuolar targeting signal.

6. The DNA sequence of claim 1 wherein said pigment is melanin or indigo.

7. The DNA sequence of claim 1 wherein said open reading frame is from a bacterial or a plant gene.

8. The DNA sequence of claim 7 wherein said gene is selected from the group consisting of ORF438, tyrA, anthocyanin R gene, anthocyanin C1 gene, pig, and tna.

9. The DNA sequence according to claim 1, wherein said transcriptional initiation region is obtained by probing a genomic library derived from a plant fiber tissue.

10. A recombinant DNA sequence comprising as operably joined components in the direction of transcription; a transcriptional initiation region functional in a cotton plant cell and an open reading frame encoding an enzyme in a biosynthetic pathway of melanin or indigo, wherein said transcriptional initiation region is selected from the group consisting of:
   a. nucleotides 65-4163 of SEQ ID NO:7, and
   b. SEQ ID NO:15.

11. The DNA sequence according to claim 10, further comprising a sequence encoding a transit peptide from a plant nuclear-encoded gene.

12. The DNA sequence according to claim 11, wherein said transit peptide is a plastid transit peptide.

13. The DNA sequence according to claim 10, further comprising a sequence encoding a signal peptide which provides for transport across the rough endoplasmic reticulum.

14. The DNA sequence according to claim 13, wherein said sequence further comprises, 3' to said open reading frame, a sequence encoding vacuolar targeting signal.

15. The DNA sequence of claim 10 wherein said open reading frame is from a bacterial gene.

16. The DNA sequence of claim 15 wherein said bacterial gene is selected from the group consisting of ORF438, tyrA, pig, and tna.

17. The DNA sequence according to claim 10 wherein said transcriptional initiation region is obtained by probing a genomic library derived from a plant fiber tissue.

18. An isolated DNA sequence comprising a transcriptional initiation region functional in a cotton plant cell, wherein said transcriptional initiation region is selected from the group consisting of:
   a. nucleotides 65-4163 of SEQ ID NO:7, and
   b. SEQ ID NO:15.

19. The DNA sequence according to claim 18, further comprising a sequence encoding a transit peptide from a plant nuclear-encoded gene.

20. The DNA sequence according to claim 19, wherein said transit peptide is a plastid transit peptide.

21. The DNA sequence according to claim 18, further comprising a sequence encoding a signal peptide which provides for transport across the rough endoplasmic reticulum.

22. The DNA sequence according to claim 21, wherein said sequence further comprises, 3' to said open reading frame, a sequence encoding a vacuolar targeting signal.

23. The DNA sequence according to claim 18 wherein said transcriptional initiation region is obtained by probing a genomic library derived from a plant fiber tissue.

24. An isolated DNA sequence comprising the sequence shown in SEQ ID NO: 1.

25. An isolated DNA sequence comprising the sequence shown in SEQ ID NO: 12.

26. An isolated DNA sequence comprising nucleotides 65-4163 of SEQ ID NO: 7.

27. An isolated DNA sequence comprising SEQ ID NO: 15.

28. A DNA construct comprising the DNA sequence of claim 1.

29. A DNA construct comprising a first and a second DNA sequence according to claim 1, wherein the open reading frame of said first DNA sequence encodes a different protein than the open reading frame of said second DNA sequence.

30. A recombinant DNA construct comprising nucleotides 65-4163 of SEQ ID NO: 7.

31. A recombinant DNA construct comprising SEQ ID NO: 15.

32. A DNA construct comprising the DNA sequence of claim 18.

33. The DNA construct of claim 32 wherein said cotton plant cell is a cotton fiber cell.

34. A DNA construct comprising the DNA sequence of claim 10.

35. The DNA construct of claim 34 wherein said cotton plant cell is a cotton fiber cell.

36. A cotton plant cell comprising the DNA construct of claim 28.

37. A cotton plant comprising the cell of claim 36.

38. A cotton plant cell comprising the DNA construct of claim 34.

39. A cotton plant comprising the plant cell of claim 38.

40. A method of modifying fiber color in a cotton plant, said method comprising:
   transforming a cotton plant cell with a DNA construct comprising a DNA sequence comprising I) a sequence selected from the group consisting of SEQ ID NO:15 and nucleotides 65-4163 of SEQ ID NO:7, and ii) an open reading frame encoding a protein selected from the group consisting of tyrosinase, tryptophanase and indole oxygenase;
   regenerating a cotton plant comprising fiber tissue from said cotton plant cell, wherein said fiber tissue comprises a substrate of said protein, and wherein said protein reacts with said substrate to produce a pigment, whereby the color of said fiber is modified.

41. The method of claim 40 wherein said DNA construct further comprises a sequence encoding a transit peptide from a plant nuclear-encoded gene.

42. The method of claim 40 wherein said DNA construct further comprises a sequence encoding a signal peptide which provides for transport across the rough endoplasmic reticulum.

43. A method of modifying fiber color in a cotton plant, said method comprising:
   transforming a cotton plant cell with a first DNA construct comprising a DNA sequence comprising I) a sequence selected from the group consisting of SEQ ID NO:15 and nucleotides 65-4163 of SEQ ID NO:7, and ii) an open reading frame encoding a protein selected from the group consisting of tyrosinase, tryptophanase and indole oxygenase;
   transforming said cotton plant cell with a second DNA construct according to claim 28 or 29;
   and regenerating a cotton plant comprising fiber tissue from said cotton plant cell, wherein said fiber tissue comprises a substrate for said protein, and wherein said protein reacts with said substrate to produce a pigment, whereby the color of said fiber is modified, and wherein the open reading frame of the DNA sequence from the first DNA construct encodes a different protein than the open reading frame of the second DNA construct.

44. The method of claim 43 wherein said pigment is melanin and said open reading frames are tyrA and ORF438.

45. The method of claim 43 wherein said pigment is indigo and said open reading frames are tna and pig.

46. The method of claim 43 wherein said pigment is anthocyanin and said two proteins are the anthocyanin R and C1 proteins.

47. The method of claim 40 wherein said fiber tissue is in the burr.

* * * * *

SEQUENCE LISTING

<160> NUMBER OF SEQ ID NOS: 18

<210> SEQ ID NO 1
<211> LENGTH: 967
<212> TYPE: DNA
<213> ORGANISM: Gossypium Hirsutum

<400> SEQUENCE: 1

```
ctttctatttt ggttaaccat ggctcataac tttcgtcatc ctttcttcct tttccaactt      60
ttactcatta ctgtctcact aatgatcggt agccacaccg tctcgtcagc ggctcgacat     120
ttattccaca cacaaacaac ctcatcagag ctgccacaat tggcttcaaa atacgaaaag     180
cacgaagagt ctgaatacaa acagccaaaa tatcatgaag agtacccaaa acatgagaag     240
cctgaaatgt acaaggagga aaaacaaaaa ccctgcaaac atcatgaaga gtaccacgag     300
tcacgcgaat cgaaggagca cgaagagtac gataaagaaa acccgatttt ccccaaatgg     360
gaaaagccta agagcacga gaaacacgaa gtcgaatatc cgaaaatacc cgagtacaag     420
gacaaacaag atgagaataa gaaacataaa gatgaagagt gccaggagtc acacgaatcg     480
aaagagcacg aagagtacga aaagaaaaa cccgatttcc ccaaatggga aaagcctaaa     540
gggcacgaga acataaagc cgaatatccg aaaatacctg agtgcaagga aaaactagat     600
gaggataagg aacataaaca tgagttccca aagcatgaaa aagaagagga aagaaacct     660
gagaaaggca tagtaccctg agtgggttaa aatgcctgaa tggccgaagt ccatgtttac     720
tcagtctggc tcgagcacta agccttaagc catatgacac tggtgcatgt gccatcatca     780
tgcagtaatt tcatgggata ttgtaattat attgttaata aaaagatgg tgagtgggaa     840
atgtgtgtgt gcattcatcc atgagcaatg ctgaatctct ttgcatgcat agagattctg     900
aatggttata gttatgtta tatcgtttgt tctagtgaaa ttaattttga atgttgtatg     960
taatgtt                                                                967
```

<210> SEQ ID NO 2
<211> LENGTH: 967
<212> TYPE: DNA
<213> ORGANISM: Gossypium Hirsutum
<220> FEATURE:
<221> NAME/KEY: CDS
<222> LOCATION: (1)..(966)

<400> SEQUENCE: 2

```
ctt tct att tgg tta acc atg gct cat aac ttt cgt cat cct ttc ttc        48
Leu Ser Ile Trp Leu Thr Met Ala His Asn Phe Arg His Pro Phe Phe
  1               5                  10                  15 ctt ttc caa ctt tta ctc att act gtc tca cta atg atc ggt agc cac        96
Leu Phe Gln Leu Leu Leu Ile Thr Val Ser Leu Met Ile Gly Ser His
             20                  25                  30 acc gtc tcg tca gcg gct cga cat tta ttc cac aca caa aca acc tca       144
Thr Val Ser Ser Ala Ala Arg His Leu Phe His Thr Gln Thr Thr Ser
         35                  40                  45 tca gag ctg cca caa ttg gct tca aaa tac gaa aag cac gaa gag tct       192
Ser Glu Leu Pro Gln Leu Ala Ser Lys Tyr Glu Lys His Glu Glu Ser
     50                  55                  60 gaa tac aaa cag cca aaa tat cat gaa gag tac cca aaa cat gag aag       240
Glu Tyr Lys Gln Pro Lys Tyr His Glu Glu Tyr Pro Lys His Glu Lys
 65                  70                  75                  80 cct gaa atg tac aag gag gaa aaa caa aaa ccc tgc aaa cat cat gaa       288
Pro Glu Met Tyr Lys Glu Glu Lys Gln Lys Pro Cys Lys His His Glu
```

-continued

```
                85                    90                    95
gag tac cac gag tca cgc gaa tcg aag gag cac gaa gag tac gat aaa    336
Glu Tyr His Glu Ser Arg Glu Ser Lys Glu His Glu Glu Tyr Asp Lys
             100                 105                 110 gaa aaa ccc gat ttc ccc aaa tgg gaa aag cct aaa gag cac gag aaa    384
Glu Lys Pro Asp Phe Pro Lys Trp Glu Lys Pro Lys Glu His Glu Lys
         115                 120                 125 cac gaa gtc gaa tat ccg aaa ata ccc gag tac aag gac aaa caa gat    432
His Glu Val Glu Tyr Pro Lys Ile Pro Glu Tyr Lys Asp Lys Gln Asp
     130                 135                 140 gag aat aag aaa cat aaa gat gaa gag tgc cag gag tca cac gaa tcg    480
Glu Asn Lys Lys His Lys Asp Glu Glu Cys Gln Glu Ser His Glu Ser
145                 150                 155                 160 aaa gag cac gaa gag tac gag aaa gaa aaa ccc gat ttc ccc aaa tgg    528
Lys Glu His Glu Glu Tyr Glu Lys Glu Lys Pro Asp Phe Pro Lys Trp
                165                 170                 175 gaa aag cct aaa ggg cac gag aaa cat aaa gcc gaa tat ccg aaa ata    576
Glu Lys Pro Lys Gly His Glu Lys His Lys Ala Glu Tyr Pro Lys Ile
            180                 185                 190 cct gag tgc aag gaa aaa cta gat gag gat aag gaa cat aaa cat gag    624
Pro Glu Cys Lys Glu Lys Leu Asp Glu Asp Lys Glu His Lys His Glu
        195                 200                 205 ttc cca aag cat gaa aaa gaa gag gag aag aaa cct gag aaa ggc ata    672
Phe Pro Lys His Glu Lys Glu Glu Glu Lys Lys Pro Glu Lys Gly Ile
    210                 215                 220 gta ccc tga gtg ggt taa aat gcc tga atg gcc gaa gtc cat gtt tac    720
Val Pro     Val Gly     Asn Ala     Met Ala Glu Val His Val Tyr
225                 230                 235                 240 tca gtc tgg ctc gag cac taa gcc tta agc cat atg aca ctg gtg cat    768
Ser Val Trp Leu Glu His     Ala Leu Ser His Met Thr Leu Val His
                245                 250                 255 gtg cca tca tca tgc agt aat ttc atg gga tat tgt aat tat att gtt    816
Val Pro Ser Ser Cys Ser Asn Phe Met Gly Tyr Cys Asn Tyr Ile Val
            260                 265                 270 aat aaa aaa gat ggt gag tgg gaa atg tgt gtg tgc att cat cca tga    864
Asn Lys Lys Asp Gly Glu Trp Glu Met Cys Val Cys Ile His Pro
        275                 280                 285 gca atg ctg aat ctc ttt gca tgc ata gag att ctg aat ggt tat agt    912
Ala Met Leu Asn Leu Phe Ala Cys Ile Glu Ile Leu Asn Gly Tyr Ser
    290                 295                 300 tta tgt tat atc gtt tgt tct agt gaa att aat ttt gaa tgt tgt atg    960
Leu Cys Tyr Ile Val Cys Ser Ser Glu Ile Asn Phe Glu Cys Cys Met
305                 310                 315                 320 taa tgt t                                                          967
    Cys
```

<210> SEQ ID NO 3
<211> LENGTH: 226
<212> TYPE: PRT
<213> ORGANISM: Gossypium Hirsutum

<400> SEQUENCE: 3

Leu Ser Ile Trp Leu Thr Met Ala His Asn Phe Arg His Pro Phe Phe
 1               5                  10                  15

Leu Phe Gln Leu Leu Ile Thr Val Ser Leu Met Ile Gly Ser His
            20                  25                  30

Thr Val Ser Ser Ala Ala Arg His Leu Phe His Thr Gln Thr Thr Ser
        35                  40                  45

Ser Glu Leu Pro Gln Leu Ala Ser Lys Tyr Glu Lys His Glu Glu Ser

```
                50                  55                  60
Glu Tyr Lys Gln Pro Lys Tyr His Glu Glu Tyr Pro Lys His Glu Lys
 65                  70                  75                  80

Pro Glu Met Tyr Lys Glu Lys Gln Lys Pro Cys Lys His His Glu
                 85                  90                  95

Glu Tyr His Glu Ser Arg Glu Ser Lys Glu His Glu Glu Tyr Asp Lys
                100                 105                 110

Glu Lys Pro Asp Phe Pro Lys Trp Glu Lys Pro Lys Glu His Glu Lys
                115                 120                 125

His Glu Val Glu Tyr Pro Lys Ile Pro Glu Tyr Lys Asp Lys Gln Asp
            130                 135                 140

Glu Asn Lys Lys His Lys Asp Glu Glu Cys Gln Glu Ser His Glu Ser
145                 150                 155                 160

Lys Glu His Glu Glu Tyr Glu Lys Glu Lys Pro Asp Phe Pro Lys Trp
                165                 170                 175

Glu Lys Pro Lys Gly His Glu Lys His Lys Ala Glu Tyr Pro Lys Ile
                180                 185                 190

Pro Glu Cys Lys Glu Lys Leu Asp Glu Asp Lys Glu His Lys His Glu
                195                 200                 205

Phe Pro Lys His Glu Lys Glu Glu Lys Lys Pro Glu Lys Gly Ile
            210                 215                 220

Val Pro
225

<210> SEQ ID NO 4
<211> LENGTH: 13
<212> TYPE: PRT
<213> ORGANISM: Gossypium Hirsutum

<400> SEQUENCE: 4

Met Ala Glu Val His Val Tyr Ser Val Trp Leu Glu His
 1               5                  10

<210> SEQ ID NO 5
<211> LENGTH: 40
<212> TYPE: PRT
<213> ORGANISM: Gossypium Hirsutum

<400> SEQUENCE: 5

Ala Leu Ser His Met Thr Leu Val His Val Pro Ser Ser Cys Ser Asn
 1               5                  10                  15

Phe Met Gly Tyr Cys Asn Tyr Ile Val Asn Lys Lys Asp Gly Glu Trp
                20                  25                  30

Glu Met Cys Val Cys Ile His Pro
            35                  40

<210> SEQ ID NO 6
<211> LENGTH: 32
<212> TYPE: PRT
<213> ORGANISM: Gossypium Hirsutum

<400> SEQUENCE: 6

Ala Met Leu Asn Leu Phe Ala Cys Ile Glu Ile Leu Asn Gly Tyr Ser
 1               5                  10                  15

Leu Cys Tyr Ile Val Cys Ser Ser Glu Ile Asn Phe Glu Cys Cys Met
                20                  25                  30

<210> SEQ ID NO 7
```

-continued

<211> LENGTH: 5547
<212> TYPE: DNA
<213> ORGANISM: Gossypium Hirsutum

<400> SEQUENCE: 7

```
actaaggga caaaagctg gagctccacc gcggtggcgg ccgctctaga actagtggat      60
cccccgtgga ctaaacaaaa catgggaaga tttgctgtaa aaaataaaa gaagcttact    120
caataacact ttgtgaattg tatacaaaag actcaatgaa aaacaataac tcaatacact    180
tttttttcact gatttacatc ctttatatag gctgaaacta caacaacttt agctaaaaaa    240
ataggataac ctaatagcaa aatcacaatc agatattaaa ccatgatttt agctaaccat    300
ttaacaactt tattgaaact aatttgaata tttcatctgc tgatatgccc aagattttag    360
gccactaacc gatttggtgg tgaactttaa catgtcatgc atttgtaact gtttgaaaca    420
agttttttgc attattttac tatatgaact gtttgattag gttgagttac acactgagct    480
tgtaagctca ctcaaatttt tctaatttct aaggtgatca gcaaacttag gaccgggcgg    540
cgtacgagag ctcggattga ttttctagtt aataaataag acgattatg ttttaaact    600
attatggact ttttggacta tgtaactgtt tgggacttta tttttgtttt ttatttgctt    660
tttttggatt tagtaattat tattttaaa ctgcaaaatt atatgttttt acaaactaag    720
tcacagtttt caaaattcca taacttagaa ttttcgctg caaaataaag taatcattta    780
agtgttttt ctgtaataaa ataaataaat aattttaacg agtattttcc taaaaattgg    840
aaattgattt accaaaatta gtatgtcaaa acacatgttt atatgttaca gggcgatatc    900
gtctaggcaa ataacatcta ggcggggttt ggagtgttac agggcgagtg ggctcatttt    960
gagtaagtat agttagggcc gagttttaga ttgcatattc aaggtcaaag attttgtaaa   1020
cttcgatgaa tgatatgtat gattgtccga ttaacgaaat atgttttttt cttttgtgtg   1080
tgttttatct cgtgtgataa gtatatagta tgtttattc caattcttat ggcatgtgac   1140
attgtggcta ttctaattaa attgatttgt tattattgaa atctgatgca tctgttctac   1200
aaagcatgga atctcatgcc tactgctttc tgttaaagat acgattgcaa gtttaacatg   1260
cttactattt tgattttgtc cttgcatgct atgtcacatt acatggggtt gggatgatat   1320
ggtaaggagg aagttttgac agtttaatga tttgcactat ctggtggttt aaccacatat   1380
ttgttatggc atcttgactg cggttatggt ggctcgaccg cccatatctg ttctggaaat   1440
ttatctgtga ctctggtggc attgtctaca attatttgtt ggtgtgtttt ggatggacga   1500
gtcgtgggga actctatttg gtgtgttgcg gagttgggta ggaaattttc gaaaaaaatt   1560
tgcattgtgt ttttctgaaa atattgcat taacataatc atgcattctc aattttggtc   1620
aattgaacgt tataaaattc tctatgatat cctgatctgt ttattacatt atatgtgttt   1680
atgcttgagt taagtcaaac attgagattc atagctcacc caattattta atcatttcag   1740
gcaatctgca gacttaggat tggatggcgt tcaggagctt ggattggttt tctcacatca   1800
tattttatta ataattatt aattaaaatt tatggacttt tggactgtct gactaatttt   1860
cagaattta ttttggtttt gggttttgtt gaattttta gataattatt ttaaatattc   1920
tgcataattt ttctgttatt tgaaaaggat gttcgaattt ttttcaaaa ttgaaacgtt   1980
taagaatttt tactactgca aattcagaat aagtgaattc gttttttaga aagattaaat   2040
aagttagtat tacgattttt agtttgattt ggtggaaagt aatgtatgtt tttgaacata   2100
attatttgac aataattaag ttttctaggg aataaacgga aatatcttct tcttttttgt   2160
aaaattacta atgcaagaac aaacaacgtt ttggggagca ataatctag ctttaagtag   2220
```

```
tcagtgtaac tctcaaaatc tggtcataac ttctaggctg agtttgctgt gctacagtag    2280
taagtctata gaaacttacc tgacaaaacg acatgacgtc agggtcgaat ctacaacttt    2340
tcctttttct tcaattaaca tatggttgat tcaagttccg atctataata atttattacg    2400
atttatcaat ttcaattacc ttatatcatc ctattataaa tataagtcag ttcaattcag    2460
ttttcgaaag ttcccaaaaa ttttgaattt tattaaattt attccctaaa accgaaatag    2520
ttatatcttt caatttaag tttcattttt caatccgatt tcaatttcat cctttttataa   2580
ctctctatta tctataatta cataaatttc aaattaattt tgaaatattt cactttagt    2640
ccctaagttc aaaactataa attttcactt tagaaattaa tcattttca catctaagca    2700
tcaaatttaa ccaaatgaca caaatttcat gattagttag atcaagcttt tgagtcttca    2760
aaacataaaa attacaaaaa aaaacaaac ttaaaatcat ttatcaattt gaacaacaaa    2820
gcttggccga atgctaagag cttaaaaatg gcttcttttg tttcttttg ttgcaaacgg     2880
tggagagaag agggaaatga agattgacca tatttttta ttatgttta acatataata     2940
ttaataattt aatcataatt atactttggt gaatgtgaca gtggggagat acgtaaagta    3000
ttttaacatt atactttttg caagcagttg gctggtctac ccaagagtga tcaaagtttg    3060
agctgccttc aatgagccaa ttttttgccca taatggataa aggcaatttg tttagttcaa    3120
ctgctcacag aataatgtta aaatgaaatt aaaataaggt ggcctggtca cacacacaaa    3180
aaaaaactaa tgttggttgg ttgaattta tattacggaa tgtaatatta tattttaaaa    3240
taaaattatg ttatttagat tcttaatatt ttggagcatt ccatactata atttcgtaac    3300
ataatattaa aatatagtaa tataaagtgt aattaacttt aaattacaag cataatatta    3360
aattttgaat caattaattt ttatttctat tatttttaatt aatttagtct attttttcaa    3420
aataaaattt aaatctaaat aaaaataatt tttccttaat gttgaaacaa ctcatgttat    3480
acttcaaaat tataagtatt atatttacct tgatgattta tttattagta tattaattct    3540
gattataatt atggtgggat acaatcgctt tccactaaat attttaacta tgatttataa    3600
atttatttca acatcgtata tttacttatt aatacataat ttatcataat tttatggaaa    3660
ttgagaccaa gaaacattaa gagaacaaat tctataacaa agacaattta gaaaaaaatg    3720
tactttttagg taattttaag tactcttaac caaacacaaa aattcaaatc aaatgaacta    3780
aataagataa tataacatac ggaacatctt acttgtaatc ttacattccc ataatttat     3840
tatgaaaaat aatcttatat tactcgaact aaatgttgtc acaaattatt atctaaataa    3900
agaaaaacac ttaatttta taacatttt tcatatattt gaaagattat attttgtata     3960
tttacgtaaa aatatttgac atagattgag caccttctta acataatccc accataagtc    4020
aagtatgtag atgagaaatt ggtacaaaca acgtggggcc aaatcccacc aaaccatctc    4080
tcattctctc ctataaaagg cttgctacac atagacaaca atccacacac aaatacacgt    4140
tcttttcttt ctatttgatt aaccatggct catagcattc gtcaccttt cttccttttc     4200
caactttttac tcataagtgt ctcactagtg accggtagcc acactgtttc ggcagcggct    4260
cgacgtttat tcgagacaca agcaacctca tcagagctcc cacaattggc ttcaaaatac    4320
gaaagcacga gagtctgaat acgaaaagcc agaatacaaa cagccaaagt atcacgaaga    4380
gtactcaaaa cttgagaagc ctgaaatgca aaggaggaa aaacaaaaac cctgcaaaca     4440
gcatgaagag taccacgagt cacacgaatc aaaggagcaa aaagagtacg agaaagaaaa    4500
tctcgacgaa ttcccccggg cgtcgacggc tagcgaagat cttcgggccc gtcgagcctt    4560
```

-continued

```
gaatcatatg acactggtgc atgtgccatc atcatgcagt aatttcatgg tatatcgtaa    4620
tatatagtta ataaaaaaga tggtgattgg gaaatgtgtg tgtgcattcc tccatgcact    4680
aatggtgaat ctctttgcat acatagaaat tctaaatggt tatagtttat gttatagtgt    4740
atgttgtagt gaaattaatt ttaaatgttg tatctaatgt taacatcact tggcttgatt    4800
tatgttatgt tatgtatttt actttaatga tattgcatgt attgttaatt taacattgct    4860
tgatcattat actcttctac tattaattat aaatggcact gttttgttta aacttttac    4920 aagttaagac atgtataaat atatgacaat ataattacag gttttagttc aatgttagct    4980
atcttagtat gttattgatg atcttaatta catttaaaca aattccactt aaaattttaa    5040
taaataataa caaataatta ttgtaatata atacattaaa tgcaacaaaa aatgaaataa    5100
ataaaataaa atagcaaata attgttataa tattgtaata taatatgtac catattctta    5160
actgaaatag ggtctaacct ataatcccta aaatttcagt ttaaatattt ttatacctac    5220
catattatta gaactctttt taaatatatt aaaattttaa ttataccaat ttaattaaac    5280
tattaattat cttaactaaa atctaaaatt ttatttaacc tattaataaa ttcctaatta    5340
tcttatctaa tttaaaactc taattatcct aatttaattt aaattcttaa ttatcttaat    5400
ttgtaacctc ctccacccag ctagatgctg acccgaatc cgggagatta catcggccat    5460
tgagatggcg tgatcagggt ttggcgcgcc ggtacccaat tcgccctata gtgagttcgt    5520
attacgcgcg ctcactgcgt ccggttt                                       5547

<210> SEQ ID NO 8
<211> LENGTH: 5547
<212> TYPE: DNA
<213> ORGANISM: Gossypium Hirsutum
<220> FEATURE:
<221> NAME/KEY: CDS
<222> LOCATION: (4164)..(4502)

<400> SEQUENCE: 8
actaaaggga acaaaagctg gagctccacc gcggtggcgg ccgctctaga actagtggat      60
cccccgtgga ctaaacaaaa catgggaaga tttgctgtaa aaaaataaaa gaagcttact     120
caataacact ttgtgaattg tatacaaaag actcaatgaa aaacaataac tcaatacact     180
ttttttcact gatttacatc ctttatatag gctgaaacta caacaacttt agctaaaaaa     240
ataggataac ctaatagcaa aatcacaatc agatattaaa ccatgatttt agctaaccat     300
ttaacaactt tattgaaact aatttgaata tttcatctgc tgatatgccc aagattttag     360
gccactaacc gatttggtgg tgaactttaa catgtcatgc atttgtaact gtttgaaaca     420
agttttttgc attattttac tatatgaact gtttgattag gttgagttac acactgagct     480
tgtaagctca ctcaaatttt tctaatttct aaggtgatca gcaaacttag gaccgggcgg     540
cgtacgagag ctcggattga ttttctagtt aataaataag acgatttatg ttttttaaact    600 attatggact ttttggacta tgtaactgtt tgggactttta ttttgttttt ttattttgctt    660 tttttggatt tagtaattat tatttttaaa ctgcaaaatt atatgttttt acaaactaag     720
tcacagtttt caaaattcca taacttagaa tttttcgctg caaaataaag taatcattta     780
agtgtttttt ctgtaataaa ataaataaat aattttaacg agtattttcc taaaaattgg     840
aaattgattt accaaaatta gtatgtcaaa acacatgttt atatgttaca gggcgatatc      900
gtctaggcaa ataacatcta ggcgggggttt ggagtgttac agggcgagtg ggctcatttt      960
gagtaagtat agttagggcc gagttttaga ttgcatattc aaggtcaaag attttgtaaa    1020
```

```
cttcgatgaa tgatatgtat gattgtccga ttaacgaaat atgtttttt cttttgtgtg      1080 tgttttatct cgtgtgataa gtatatagta tgttttattc caattcttat ggcatgtgac      1140
attgtggcta ttctaattaa attgatttgt tattattgaa atctgatgca tctgttctac      1200
aaagcatgga atctcatgcc tactgctttc tgttaaagat acgattgcaa gtttaacatg      1260
cttactattt tgattttgtc cttgcatgct atgtcacatt acatggggtt gggatgatat      1320
ggtaaggagg aagttttgac agtttaatga tttgcactat ctggtggttt aaccacatat      1380
ttgttatggc atcttgactg cggttatggt ggctcgaccg cccatatctg ttctggaaat      1440
ttatctgtga ctctggtggc attgtctaca attatttgtt ggtgtgtttt ggatggacga      1500
gtcgtgggga actctatttg gtgtgttgcg gagttgggta ggaaattttc gaaaaaaatt      1560
tgcattgtgt ttttctgaaa aatattgcat taacataatc atgcattctc aattttggtc      1620
aattgaacgt tataaaattc tctatgatat cctgatctgt ttattacatt atatgtgttt      1680
atgcttgagt taagtcaaac attgagattc atagctcacc caattattta atcatttcag      1740
gcaatctgca gacttaggat tggatggcgt tcaggagctt ggattggttt tctcacatca      1800
tattttatta ataattatt aattaaaatt tatggacttt tggactgtct gactaatttt      1860
cagaatttta ttttggtttt gggttttgtt gaattttta gataattatt ttaaatattc      1920
tgcataattt ttctgttatt tgaaaaggat gttcgaattt tttttcaaaa ttgaaacgtt      1980
taagaatttt tactactgca aattcagaat aagtgaattt gttttttaga aagattaaat      2040
aagttagtat tacgattttt agtttgattt ggtggaaagt aatgtatgtt tttgaacata      2100
attatttgac aataattaag ttttctaggg aataaacgga aatatcttct tcttttttgt      2160
aaaattacta atgcaagaac aaacaacgtt tgggagca aataatctag ctttaagtag      2220
tcagtgtaac tctcaaaatc tggtcataac ttctaggctg agtttgctgt gctacagtag      2280
taagtctata gaaacttacc tgacaaaacg acatgacgtc agggtcgaat ctacaacttt      2340
tcctttttct tcaattaaca tatggttgat tcaagttccg atctataata atttattacg      2400
atttatcaat ttcaattacc ttatatcatc ctattataaa tataagtcag ttcaattcag      2460
ttttcgaaag ttcccaaaaa ttttgaattt tattaaattt attccctaaa accgaaatag      2520
ttatatcttt caaatttaag tttcattttt caatccgatt tcaatttcat ccttttataa      2580
ctctctatta tctataatta cataaatttc aaattaattt tgaaatattt acactttagt      2640
ccctaagttc aaaactataa attttcactt tagaaattaa tcattttca catctaagca      2700 tcaaatttaa ccaaatgaca caaatttcat gattagttag atcaagcttt tgagtcttca      2760
aaacataaaa attacaaaaa aaaacaaac ttaaaatcat ttatcaattt gaacaacaaa      2820
gcttggccga atgctaagag cttaaaaatg gcttcttttg tttcttttg ttgcaaacgg      2880 tggagagaag agggaaatga agattgacca tatttttta ttatgtttta acatataata      2940 ttataattt aatcataatt atactttggt gaatgtgaca gtgggagat acgtaaagta      3000 ttttaacatt atacttttg caagcagttg gctggtctac ccaagagtga tcaaagtttg      3060
agctgccttc aatgagccaa ttttgcccca taatggataa aggcaatttg tttagttcaa      3120
ctgctcacag aataatgtta aaatgaaatt aaaataaggt ggcctggtca cacacacaaa      3180
aaaaaactaa tgttggttgg ttgaatttta tattacggaa tgtaatatta tattttaaaa      3240
taaaattatg ttatttagat tcttaatatt ttggagcatt ccatactata atttcgtaac      3300
ataatattaa aatatagtaa tataaagtgt aattaacttt aaattacaag cataatatta      3360
aattttgaat caattaattt ttatttctat tattttaatt aatttagtct atttttcaa      3420
```

```
aataaaattt aaatctaaat aaaaataatt tttccttaat gttgaaacaa ctcatgttat    3480
acttcaaaat tataagtatt atatttacct tgatgattta tttattagta tattaattct    3540
gattataatt atggtgggat acaatcgctt tccactaaat attttaacta tgatttataa    3600
atttatttca acatcgtata tttacttatt aatacataat ttatcataat tttatggaaa    3660
ttgagaccaa gaaacattaa gagaacaaat tctataacaa agacaattta gaaaaaaatg    3720
tacttttagg taattttaag tactcttaac caaacacaaa aattcaaatc aaatgaacta    3780
aataagataa tataacatac ggaacatctt acttgtaatc ttacattccc ataattttat    3840
tatgaaaaat aatcttatat tactcgaact aaatgttgtc acaaattatt atctaaataa    3900
agaaaaacac ttaattttta taacatttt tcatatattt gaaagattat attttgtata     3960
tttacgtaaa aatatttgac atagattgag caccttctta acataatccc accataagtc    4020
aagtatgtag atgagaaatt ggtacaaaca acgtggggcc aaatcccacc aaaccatctc    4080
tcattctctc ctataaaagg cttgctacac atagacaaca atccacacac aaatacacgt    4140
tcttttcttt ctatttgatt aac cat ggc tca tag cat tcg tca ccc ttt ctt    4193
                         His Gly Ser     His Ser Ser Pro Phe Leu
                          1                5                 10 cct ttt cca act ttt act cat aag tgt ctc act agt gac cgg tag cca       4241
Pro Phe Pro Thr Phe Thr His Lys Cys Leu Thr Ser Asp Arg     Pro
             15                  20                  25 cac tgt ttc ggc agc ggc tcg acg ttt att cga gac aca agc aac ctc       4289
His Cys Phe Gly Ser Gly Ser Thr Phe Ile Arg Asp Thr Ser Asn Leu
             30                  35                  40 atc aga gct ccc aca att ggc ttc aaa ata cga aag cac gag agt ctg       4337
Ile Arg Ala Pro Thr Ile Gly Phe Lys Ile Arg Lys His Glu Ser Leu
             45                  50                  55 aat acg aaa agc cag aat aca aac agc caa agt atc acg aag agt act       4385
Asn Thr Lys Ser Gln Asn Thr Asn Ser Gln Ser Ile Thr Lys Ser Thr
         60                  65                  70 caa aac ttg aga agc ctg aaa tgc aaa agg agg aaa aac aaa aac cct       4433
Gln Asn Leu Arg Ser Leu Lys Cys Lys Arg Arg Lys Asn Lys Asn Pro
 75                  80                  85                  90 gca aac agc atg aag agt acc acg agt cac acg aat caa agg agc aaa       4481
Ala Asn Ser Met Lys Ser Thr Thr Ser His Thr Asn Gln Arg Ser Lys
             95                 100                 105 aag agt acg aga aag aaa atc tcgacgaatt cccccgggcg tcgacggcta          4532
Lys Ser Thr Arg Lys Lys Ile
            110 gcgaagatct tcgggcccgt cgagccttga atcatatgac actggtgcat gtgccatcat    4592 catgcagtaa tttcatggta tatcgtaata tatagttaat aaaaaagatg gtgattggga    4652 aatgtgtgtg tgcattcctc catgcactaa tggtgaatct ctttgcatac atagaaattc    4712 taaatggtta tagtttatgt tatagtgtat gttgtagtga aattaatttt aaatgttgta    4772 tctaatgtta acatcacttg gcttgattta tgttatgtta tgtattttac tttaatgata    4832 ttgcatgtat tgttaattta acattgcttg atcattatac tcttctacta ttaattataa    4892 atggcactgt tttgtttaaa cttttacaa gttaagacat gtataaatat atgacaatat     4952 aattacaggt tttagttcaa tgttagctat cttagtatgt tattgatgat cttaattaca    5012 tttaaacaaa ttccacttaa aattttaata aataataaca aataattatt gtaatataat    5072 acattaaatg caacaaaaaa tgaaataaat aaaataaaat agcaaataat tgttataata    5132 ttgtaatata atatgtacca tattcttaac tgaaataggg tctaacctat aatccctaaa    5192
```

```
atttcagttt aaatattttt atacctacca tattattaga actcttttta aatatattaa      5252
aattttaatt ataccaattt aattaaacta ttaattatct taactaaaat ctaaaatttt      5312
atttaaccta ttaataaatt cctaattatc ttatctaatt taaaactcta attatcctaa      5372
tttaatttaa attcttaatt atcttaattt gtaacctcct ccacccagct agatgctgga      5432
cccgaatccg ggagattaca tcggccattg agatggcgtg atcagggttt ggcgcgccgg      5492
tacccaattc gccctatagt gagttcgtat tacgcgcgct cactgcgtcc ggttt          5547
```

<210> SEQ ID NO 9
<211> LENGTH: 20
<212> TYPE: PRT
<213> ORGANISM: Gossypium Hirsutum

<400> SEQUENCE: 9

His Ser Ser Pro Phe Leu Pro Phe Pro Thr Phe Thr His Lys Cys Leu
 1               5                  10                  15

Thr Ser Asp Arg
         20

<210> SEQ ID NO 10
<211> LENGTH: 88
<212> TYPE: PRT
<213> ORGANISM: Gossypium Hirsutum

<400> SEQUENCE: 10

Pro His Cys Phe Gly Ser Gly Ser Thr Phe Ile Arg Asp Thr Ser Asn
 1               5                  10                  15

Leu Ile Arg Ala Pro Thr Ile Gly Phe Lys Ile Arg Lys His Glu Ser
             20                  25                  30

Leu Asn Thr Lys Ser Gln Asn Thr Asn Ser Gln Ser Ile Thr Lys Ser
         35                  40                  45

Thr Gln Asn Leu Arg Ser Leu Lys Cys Lys Arg Lys Asn Lys Asn
     50                  55                  60

Pro Ala Asn Ser Met Lys Ser Thr Thr Ser His Thr Asn Gln Arg Ser
 65                  70                  75                  80

Lys Lys Ser Thr Arg Lys Lys Ile
             85

<210> SEQ ID NO 11
<211> LENGTH: 5518
<212> TYPE: DNA
<213> ORGANISM: Gossypium Hirsutum

<400> SEQUENCE: 11

```
actaaaggga acaaaagctg gagctccacc gcggtggcgg ccgctctagg atccccgtg        60 gactaaacaa acatgggaa gatttgctgt aaaaaaataa agaagctta ctcaataaca       120 ctttgtgaat tgtatacaaa agactcaatg aaaaacaata actcaataca ctttttttca     180
ctgatttaca tcctttatat aggctgaaac tacaacaact ttagctaaaa aaataggata     240
acctaatagc aaaatcacaa tcagatatta accatgatt ttagctaacc atttaacaac     300
tttattgaaa ctaatttgaa tatttcatct gctgatatgc ccaagatttt aggccactaa     360
ccgatttggt ggtgaacttt aacatgtcat gcatttgtaa ctgtttgaaa caagtttttt     420
gcattatttt actatatgaa ctgtttgatt aggttgagtt acacactgag cttgtaagct     480
cactcaaatt tttctaattt ctaaggtgat cagcaaactt aggaccgggc ggcgtacgag     540
agctcggatt gattttctag ttaataaata agacgattta tgttttaaa ctattatgga     600
```

-continued

| | |
|---|---|
| cttttttggac tatgtaactg tttgggactt tatttttgtt ttttatttgc ttttttttgga | 660 |
| tttagtaatt attatttta aactgcaaaa ttatatgttt ttacaaacta agtcacagtt | 720 |
| ttcaaaattc cataacttag aatttttcgc tgcaaaataa agtaatcatt taagtgtttt | 780 |
| ttctgtaata aaataaataa ataattttaa cgagtatttt cctaaaaatt ggaaattgat | 840 |
| ttaccaaaat tagtatgtca aaacacatgt ttatatgtta cagggcgata tcgtctaggc | 900 |
| aaataacatc taggcggggt ttggagtgtt acagggcgag tgggctcatt ttgagtaagt | 960 |
| atagttaggg ccgagtttta gattgcatat tcaaggtcaa agattttgta aacttcgatg | 1020 |
| aatgatatgt atgattgtcc gattaacgaa atatgttttt ttcttttgtg tgtgttttat | 1080 |
| ctcgtgtgat aagtatatag tatgttttat tccaattctt atggcatgtg acattgtggc | 1140 |
| tattctaatt aaattgattt gttattattg aaatctgatg catctgttct acaaagcatg | 1200 |
| gaatctcatg cctactgctt tctgttaaag atacgattgc aagtttaaca tgcttactat | 1260 |
| tttgattttg tccttgcatg ctatgtcaca ttacatgggg ttgggatgat atggtaagga | 1320 |
| ggaagttttg acagtttaat gatttgcact atctggtggt ttaaccacat atttgttatg | 1380 |
| gcatcttgac tgcggttatg gtggctcgac cgcccatatc tgttctggaa atttatctgt | 1440 |
| gactctggtg gcattgtcta caattatttg ttggtgtgtt ttggatggac gagtcgtggg | 1500 |
| gaactctatt tggtgtgttg cggagttggg taggaaattt tcgaaaaaaa tttgcattgt | 1560 |
| gtttttctga aaaatattgc attaacataa tcatgcattc tcaattttgg tcaattgaac | 1620 |
| gttataaaat tctctatgat atcctgatct gtttattaca ttatatgtgt ttatgcttga | 1680 |
| gttaagtcaa acattgagat tcatagctca cccaattatt taatcatttc aggcaatctg | 1740 |
| cagacttagg attggatggc gttcaggagc ttggattggt tttctcacat catatttat | 1800 |
| taaataatta ttaattaaaa tttatggact tttggactgt ctgactaatt ttcagaattt | 1860 |
| tattttggtt ttgggttttg ttgaattttt tagataatta ttttaaatat tctgcataat | 1920 |
| ttttctgtta tttgaaaagg atgttcgaat ttttttttcaa aattgaaacg tttaagaatt | 1980 |
| tttactactg caaattcaga ataagtgaat ttgtttttta gaaagattaa ataagttagt | 2040 |
| attacgattt ttagtttgat ttggtggaaa gtaatgtatg ttttgaaca taattatttg | 2100 |
| acaataatta agttttctag ggaataaacg gaaatatctt cttctttttt gtaaaattac | 2160 |
| taatgcaaga acaaacaacg ttttggggag caaataatct agctttaagt agtcagtgta | 2220 |
| actctcaaaa tctggtcata acttctaggc tgagtttgct gtgctacagt agtaagtcta | 2280 |
| tagaaactta cctgacaaaa cgacatgacg tcagggtcga atctacaact tttcctttt | 2340 |
| cttcaattaa catatggttg attcaagttc cgatctataa taatttatta cgatttatca | 2400 |
| atttcaatta ccttatatca tcctattata aatataagtc agttcaattc agttttcgaa | 2460 |
| agttcccaaa aattttgaat tttattaaat ttattcccta aaaccgaaat agttatatct | 2520 |
| ttcaaattta agtttcattt ttcaatccga tttcaatttc atcctttat aactctctat | 2580 |
| tatctataat tacataaatt tcaaattaat tttgaaatat ttcactttta gtccctaagt | 2640 |
| tcaaaactat aaattttcac tttagaaatt aatcattttt cacatctaag catcaaattt | 2700 |
| aaccaaatga cacaaatttc atgattagtt agatcaagct tttgagtctt caaaacataa | 2760 |
| aaattacaaa aaaaaaacaa acttaaaatc atttatcaat ttgaacaaca aagcttggcc | 2820 |
| gaatgctaag agcttaaaaa tggcttcttt tgtttctttt tgttgcaaac ggtggagaga | 2880 |
| agagggaaat gaagattgac catattttttt tattatgttt taacatataa tattaataat | 2940 |

-continued

```
ttaatcataa ttatactttg gtgaatgtga cagtggggag atacgtaaag tattttaaca    3000
ttatactttt tgcaagcagt tggctggtct acccaagagt gatcaaagtt tgagctgcct    3060
tcaatgagcc aattttttgcc cataatggat aaaggcaatt tgtttagttc aactgctcac   3120
agaataatgt taaaatgaaa ttaaaataag gtggcctggt cacacacaca aaaaaaaact   3180
aatgttggtt ggttgaattt tatattacgg aatgtaatat tatatttaa aataaaatta    3240
tgttatttag attcttaata ttttggagca ttccatacta taatttcgta acataatatt   3300
aaaatatagt aatataaagt gtaattaact ttaaattaca agcataatat taaattttga   3360
atcaattaat ttttatttct attattttaa ttaatttagt ctatttttc aaaataaaat    3420
ttaaatctaa ataaaaataa ttttccttta atgttgaaac aactcatgtt atacttcaaa  3480
attataagta ttatatttac cttgatgatt tatttattag tatattaatt ctgattataa   3540
ttatggtggg atacaatcgc tttccactaa atattttaac tatgatttat aaatttattt   3600
caacatcgta tatttactta ttaatacata atttatcata attttatgga aattgagacc  3660
aagaaacatt aagagaacaa attctataac aaagacaatt tagaaaaaaa tgtacttta   3720
ggtaatttta agtactctta accaaacaca aaaattcaaa tcaaatgaac taaataagat  3780
aatataacat acggaacatc ttacttgtaa tcttacattc ccataatttt attatgaaaa   3840
ataatcttat attactcgaa ctaaatgttg tcacaaatta ttatctaaat aaagaaaaac  3900
acttaattt tataacattt tttcatatat ttgaaagatt atatttgtta tatttacgta    3960
aaaatatttg acatagattg agcaccttct taacataatc ccaccataag tcaagtatgt  4020
agatgagaaa ttggtacaaa aacgtgggg ccaaatccca ccaaaccatc tctcattctc   4080
tcctataaaa ggcttgctac acatagacaa caatccacac acaaatacac gttctttct   4140
ttctatttga ttaaccatgg ctcatagcat tcgtcaccct ttcttccttt tccaacttt    4200
actcataagt gtctcactag tgaccggtag ccacactgtt tcggcagcgg ctcgacgttt   4260
attcgagaca caagcaacct catcagagct cccacaattg gcttcaaaat acgaaaagca   4320
cgaagagtct gaatacgaaa agccagaata caaacagcca agtatcacg aagagtactc   4380
aaaacttgag aagcctgaaa tgcaaaagga ggaaaaacaa aaaccctgca acagcatga   4440
agagtaccac gagtcacacg aatcaaagga gcaaaaagag tacgagaaag aaaatctcga   4500
cgggcccgaa gatcttcgct agccgtcgac gcccggggga attcgtcgag ccttgaatca   4560
tatgacgctg gtgcatgtgc catcatcatg cagtaatttc atggtatatc gtaatatata   4620
gttaataaaa aagatggtga ttgggaaatg tgtgtgtgca ttcctccatg cactaatggt  4680
gaatctcttt gcatacatag aaattctaaa tggttatagt ttatgttata gtgtatgttg   4740
tagtgaaakt aattttaaat gttgtatcta atgttaacat cacttggctt gatttatgtt   4800
atgttatgta ttttactta atgatattgc atgtattgtt aatttaacat tgcttgatca    4860
ttatactctt ctactattaa ttataaatgg cactgttttg tttaaacttt ttacaagtta  4920
agacatgtat aaatatatga caatataatt acaagttta gttcaatgtt agctatctta   4980
gtatgttatt gatgatctta attcacattta aacaaattcc acttaaaatt ttaataaata   5040
ataacaaata attattgtaa tataatacat taaatgcaac aaaaaatgaa ataaataaaa   5100
taaaatagca ataattgtt ataatattgt aatataatat gtaccatatt cttaactgaa   5160
atagggtcta acctataatc cctaaaattt cagtttaaat attttatac ctgccatatt   5220
attagaactc ttttttaaata tattaaaatt ttaattatac caatttaatt taaactatta  5280
attatcttaa ctaaaatcta aaattttatt taacctatta attaaattcc taattatctt   5340
```

```
atctaattta aaactctaat tatcctaatt tgatttaaat tcttgattat cttaatttgt      5400
aacctcctcc acccagctag atgctggacc cgaatccggg agattacatc ggcattgaga      5460
tggcctagta gtgatcaggg ttttctagag gtacccaatt cgccctatag tgagtcgt       5518
```

<210> SEQ ID NO 12
<211> LENGTH: 910
<212> TYPE: DNA
<213> ORGANISM: Gossypium Hirsutum

<400> SEQUENCE: 12

```
aaaaaacaat gagcactgca agatttatca agtgtgtcac ggtcggtgat ggagctgtgg       60
ggaaaacttg tatgctcatt tcatatacca gcaatacttt cccaacggat tatgttccaa      120
cagtatttga taactttagt gccaatgtgg tggtggatgg cagcacagtg aaccttggcc      180
tatgggacac tgccgggcaa gaagattata ataggctaag gccactgagt tatagaggag      240
ctgatgtgtt tttgttggcc ttttctctta taagcaaggc cagttatgaa aacatctaca      300
aaaagtggat cccagagcta agacattatg ctcataatgt accagttgtg cttgttggaa      360
ccaaactaga tttgcgagat gacaagcagt tcctcattga tcaccctgga gcaacaccaa      420
tatcaacatc tcagggagaa gaactaaaga agatgatagg agcagttact tatatagaat      480
gcagctccaa aacccaacag aatgtgaagg ctgttttcga tgctgcaata aaagtagctt      540
tgaggccacc aaaaccaaag agaaagcctt gcaaaaggag aacatgtgct ttcctttgaa      600
tattggatca ttattacagt caaaaacagt taacaaaagc tgttgcagat aaacactgaa      660
tctgctatag tttgttttttg gtttacatat gttccacgtg aaactatgaa gcatctctaa      720
gaaaacccaa actatcatat caacccatcg atcaatgaat cgatttcaat tttcgcagta      780
taagttcctt ttaatccttt ctttttactt cattttataa cgaattctat ggataatgtt      840
ccctacaaac atgtcattac aatgtttaat tataaattcc attcttctat tttactaaaa      900
aaaaaaaaaa                                                             910
```

<210> SEQ ID NO 13
<211> LENGTH: 910
<212> TYPE: DNA
<213> ORGANISM: Gossypium Hirsutum
<220> FEATURE:
<221> NAME/KEY: CDS
<222> LOCATION: (9)..(596)

<400> SEQUENCE: 13

```
aaaaaaca atg agc act gca aga ttt atc aag tgt gtc acg gtc ggt gat         50
         Met Ser Thr Ala Arg Phe Ile Lys Cys Val Thr Val Gly Asp
          1               5                   10 gga gct gtg ggg aaa act tgt atg ctc att tca tat acc agc aat act          98
Gly Ala Val Gly Lys Thr Cys Met Leu Ile Ser Tyr Thr Ser Asn Thr
 15                  20                  25                  30 ttc cca acg gat tat gtt cca aca gta ttt gat aac ttt agt gcc aat         146
Phe Pro Thr Asp Tyr Val Pro Thr Val Phe Asp Asn Phe Ser Ala Asn
                 35                  40                  45 gtg gtg gtg gat ggc agc aca gtg aac ctt ggc cta tgg gac act gcc         194
Val Val Val Asp Gly Ser Thr Val Asn Leu Gly Leu Trp Asp Thr Ala
             50                  55                  60 ggg caa gaa gat tat aat agg cta agg cca ctg agt tat aga gga gct         242
Gly Gln Glu Asp Tyr Asn Arg Leu Arg Pro Leu Ser Tyr Arg Gly Ala
 65                  70                  75 gat gtg ttt ttg ttg gcc ttt tct ctt ata agc aag gcc agt tat gaa         290
Asp Val Phe Leu Leu Ala Phe Ser Leu Ile Ser Lys Ala Ser Tyr Glu
```

```
Asp Val Phe Leu Leu Ala Phe Ser Leu Ile Ser Lys Ala Ser Tyr Glu
        80                  85                  90 aac atc tac aaa aag tgg atc cca gag cta aga cat tat gct cat aat     338
Asn Ile Tyr Lys Lys Trp Ile Pro Glu Leu Arg His Tyr Ala His Asn
 95                 100                 105                 110 gta cca gtt gtg ctt gtt gga acc aaa cta gat ttg cga gat gac aag     386
Val Pro Val Val Leu Val Gly Thr Lys Leu Asp Leu Arg Asp Asp Lys
                    115                 120                 125 cag ttc ctc att gat cac cct gga gca aca cca ata tca aca tct cag     434
Gln Phe Leu Ile Asp His Pro Gly Ala Thr Pro Ile Ser Thr Ser Gln
                130                 135                 140 gga gaa gaa cta aag aag atg ata gga gca gtt act tat ata gaa tgc     482
Gly Glu Glu Leu Lys Lys Met Ile Gly Ala Val Thr Tyr Ile Glu Cys
145                 150                 155 agc tcc aaa acc caa cag aat gtg aag gct gtt ttc gat gct gca ata     530
Ser Ser Lys Thr Gln Gln Asn Val Lys Ala Val Phe Asp Ala Ala Ile
        160                 165                 170 aaa gta gct ttg agg cca cca aaa cca aag aga aag cct tgc aaa agg     578
Lys Val Ala Leu Arg Pro Pro Lys Pro Lys Arg Lys Pro Cys Lys Arg
175                 180                 185                 190 aga aca tgt gct ttc ctt tgaatattgg atcattata cagtcaaaaa             626
Arg Thr Cys Ala Phe Leu
                195 cagttaacaa aagctgttgc agataaacac tgaatctgct atagtttgtt tttggtttac    686 atatgttcca cgtgaaacta tgaagcatct ctaagaaaac ccaaactatc atatcaaccc    746 atcgatcaat gaatcgattt caattttcgc agtataagtt cctttaatc ctttcttttt     806 acttcatttt ataacgaatt ctatggataa tgttccctac aaacatgtca ttacaatgtt    866 taattataaa ttccattctt ctattttact aaaaaaaaaa aaaa                    910

<210> SEQ ID NO 14
<211> LENGTH: 196
<212> TYPE: PRT
<213> ORGANISM: Gossypium Hirsutum

<400> SEQUENCE: 14

Met Ser Thr Ala Arg Phe Ile Lys Cys Val Thr Val Gly Asp Gly Ala
 1               5                  10                  15

Val Gly Lys Thr Cys Met Leu Ile Ser Tyr Thr Ser Asn Thr Phe Pro
                20                  25                  30

Thr Asp Tyr Val Pro Thr Val Phe Asp Asn Phe Ser Ala Asn Val Val
        35                  40                  45

Val Asp Gly Ser Thr Val Asn Leu Gly Leu Trp Asp Thr Ala Gly Gln
 50                 55                  60

Glu Asp Tyr Asn Arg Leu Arg Pro Leu Ser Tyr Arg Gly Ala Asp Val
 65                 70                  75                  80

Phe Leu Leu Ala Phe Ser Leu Ile Ser Lys Ala Ser Tyr Glu Asn Ile
                85                  90                  95

Tyr Lys Lys Trp Ile Pro Glu Leu Arg His Tyr Ala His Asn Val Pro
                100                 105                 110

Val Val Leu Val Gly Thr Lys Leu Asp Leu Arg Asp Asp Lys Gln Phe
            115                 120                 125

Leu Ile Asp His Pro Gly Ala Thr Pro Ile Ser Thr Ser Gln Gly Glu
        130                 135                 140

Glu Leu Lys Lys Met Ile Gly Ala Val Thr Tyr Ile Glu Cys Ser Ser
145                 150                 155                 160
```

```
Lys Thr Gln Gln Asn Val Lys Ala Val Phe Asp Ala Ala Ile Lys Val
                165                 170                 175

Ala Leu Arg Pro Pro Lys Pro Lys Arg Lys Pro Cys Lys Arg Arg Thr
            180                 185                 190

Cys Ala Phe Leu
        195

<210> SEQ ID NO 15
<211> LENGTH: 3045
<212> TYPE: DNA
<213> ORGANISM: Gossypium Hirsutum

<400> SEQUENCE: 15
ttggatgaga accaatttt aatagtaaan cctaaccaat ttttaataat aaagctgact      60
cctagtacaa gagcttttat tcattcttct attttgcttt cctctaggct tggcaatcga   120
gaattttctt gtgttacaat ataataaata catcgtagaa ataaatttta ttcaaattga   180
agtcttaacc atctttaata tttgtagatg taatttaaat gaaagataaa tacatattct   240
tggacatgta ttttcatctt aatgtttgtg gctttggtga taggtgtatt gatgtacgat   300 gtctttaaa tcacatatca cattttgagt ttgtatgatg ataagtcgac ataancgaaa    360
tatggtgtga tcttcacttt tgaactttga taagtcacca aactttaaca aagtttgatt   420
gtgtacatat atatatatat cttcaaattt tataataaaa attgtgttta aataatttac   480
agttatatta ttttttttatc tctaatttta tttgtcgcca aatttttagt tgatatttta   540
acataaaaaa aattgtacac atttacaagc ccatatacaa ataattatat aaatattcat   600
taaaaaatat atttaaatat aggatataaa tataactatt ttagaattat tctactttaa   660
gataacatag gttaaatgta taattaataa ggttagttta ttgtaaagat gagtatatat   720
gtcgtaaaca taatcactaa ccatttttat taacttcttg gttttgaagt tccaaaaaga   780
aaatggaagg gaaatttgag agtaagttca tgtttatatt atacataatg aagttgatgt   840
tttcttcttt ttaatatttt tatacaaaat atttaaataa aataattaag gattgaatga   900
aaaatataat gaaagtcgtt ttactaatag tcatattgca ttttgtcgca tctacttaaa   960
taatagataa attaattgtg gtacattaga tcaaagaaca aactagattt tgtcccattc  1020
tattgttaaa agctggtccg tttacattaa aataaggtac atgttacatg ccacgtataa  1080
ctatctggtt attctatcaa tcacgctaat ttttaacagt agaaatgaat gtaatttttta  1140 aatagaaagg gtcaaattgt tatttgatct aacacgtagg gattaattta cttatttttcc  1200 taaagaaata agtaaaatat aatttgaatc ttaatacaaa aactttcatg atactttttat  1260 catattttac ttataattta atattgtgag agtaacaaar ttaaaaaaca tagaaacacc  1320
aaaagttagt tatggtgtga ctcatataca cagttaaaat ttgaataaat ttttttcttc  1380
gtcattaatt ccatcatggg ttttttttt tctagttaag ccataattat caaaataatc  1440
atcattaatc ctatcaatac cccgccctgc ctccctccct caatacttaa acccaactaa  1500
cacccagcac caaacgcact ttaatagcca cctatttcta gccatgtcct tgcacttaaa  1560
gaaaagtaaa gctaacctgc aatcattcca tatcgaggcc tcaacagata aagttggttg  1620
atgggtttgc accaagttgt taaaacccgg ccctcaactt ccctttctt ttcatcctcc   1680 ccactccaca ccctccaatt ttcttcatat ggttctatta taagttcttt ataatcacag  1740
aatcaagata agtcctcagc aaacaaaaaa ccatggctct cgagcaagat ctggactagt  1800
cagagctctg aatattggat cattattaca gtcaaaaaca gttaacaaaa gctgttgcag  1860
```

-continued

| | |
|---|---|
| ataaacactg aatctgctat agtttgtttt tggtttacat atgttccacg tgaaactatg | 1920 |
| aagcatctct aagaaaaccc aaactatcat atcaacccat cgatcaatga atcgatttca | 1980 |
| attttcgcag tataagttcc ttttaatcct ttcttttttac ttcattttat aacgaattct | 2040 |
| atggataatg ttccctacaa acatgtcatt acaatgttta attataaatt ccattcttct | 2100 |
| attttactaa gatattagta acttcaaact gctgatttt actaatttat tatttataaa | 2160 |
| ttgttagaat gattattttt caataattta acaacaatat ttaatattat tattattatt | 2220 |
| atttctcaat ttttattaaa caaaaacata aattttgac aaattaaaat aaatgaatta | 2280 |
| atttctcaat ttttcgtgca actattacaa aaatccttca tagtcctaat cttaatttga | 2340 |
| tgcagaggtg ataataatct taatttgatg cagaggtaat aatgggccgg tttgagctg | 2400 |
| gacttaagca tgatattgac gtactttata tttttccaaa ttcaacccag ctcgaaatat | 2460 |
| gagtctaaaa ttttgtccaa tttaatccaa gcccattta agttcgtcca tattattttt | 2520 |
| taatttaaaa aatttatatc attttatttt aatatttaat tattttatat atttttatt | 2580 |
| tattgaaaat tttatatag tcatcttaac attatgttaa tgtttatatt agagtagtat | 2640 |
| tatatatatt tagtataggt ttattttgtt aataaactta aaaatgggtc ttgtgggcta | 2700 |
| gacttggacc ttaaatgctc aaactcaaac ttaattcata ttttaaacag cttaatatt | 2760 |
| tttatttaca ctgtttcaaa tttttcgggt gaaatatctt cgagtctaga ttaataacac | 2820 |
| cacaggtcta atttgatgct caatgaaaat gaaatcatat tgagcttaat taatattcca | 2880 |
| ttcttctttg ctgaaaggac caagcaattc gagttacatt aaggtaaaag agtatgggat | 2940 |
| ccgccaaacc tgccccaatg tctcttcaac catccaaaaa cttgagtcag tatcacatac | 3000 |
| atgtaccgnt atttatttat ttattgaaat tggcattatt tcttg | 3045 |

<210> SEQ ID NO 16
<211> LENGTH: 1871
<212> TYPE: DNA
<213> ORGANISM: Gossypium Hirsutum

<400> SEQUENCE: 16

| | |
|---|---|
| gggcattcca cacgaccatg tgtcccctat ttccaggcat tttgagactt cacctaaact | 60 |
| tctagagttg tttcaaatta gcccctattt gttcttaaat cattttagga tcttgtaaac | 120 |
| tcgtatttag gactaaatgt gtaatttata ctttaattat gattgattaa ttgattgatt | 180 |
| tngtagtaat gcccgtgacc ctaatccgtt agcgaagagg ggttaggggt taggggtttt | 240 |
| attattattt tttagatatt gtataactct tgttttattt ttaattttgt tactatttca | 300 |
| aaggcatttg tttgtagtgt tatttcgagt aggtttatg ggtgaacaac ccttgaccgc | 360 |
| caaatcaatc acaagagttc aacattttat ttattttgaa atgtattaaa aatcgttaat | 420 |
| ctatatattc gccccattat tgggattaaa tattcacaag ggtttagacc gtcatgagac | 480 |
| agattagttt tatcttactg atggtcacat cacaatagta attcaactta atacgagagg | 540 |
| aaccattgat tcacgcaatt ggtcatcgca cttagttgaa aagctagggg tgcgaagcta | 600 |
| ccgtacgctg gattatgatt gaacacctct aagtcagaat ccgaattaga aacaatgcac | 660 |
| gtgtccgttg cctgattgcc aaccccaata acacgtgttg taggtttaac catgtttatg | 720 |
| aaagataagg ttttttttt tataagcaag caactatagg ggtttacttc cgtgcgcaaa | 780 |
| tttttaggtt acctatttg ggagggggga ttatgattca agtgaaagaa agttggcaca | 840 |
| cacacaatca gtacatctgt tttgacagag acacagccta aaaacagcag caaacaagcc | 900 |
| taaaggaatc acccaaaaac aacaaccaaa agtacagagg aaaacaaaag aatccctgtt | 960 |

```
accaccaagc tgaaaaaag aaaataaaac tcaactttg gcaataaaaa ccctcctacc    1020
ctcaacccct aaccacgcaa caatcagcaa tactccaagc aaccattttc cttacaagtt    1080
tgttttcctt gtgattaatc catatggcta gctccatgtc ccttaagctt gcatgtctgc    1140
tagtgttgtg catggtggtg ggtgcacccc tggctcaagg ggacgtaacc cgtgctgatg    1200
gcgtagtcac ccttccacgc tgccttcctt tattgatagg gaatggtaat ggtgctgatg    1260
ctgatgttga tgcccagct tgctgcgaca tcgtcagggg tctcttgagc tcgctgctct    1320
gtggtggtgt ttaggaaccg atctagcttg aaatcgggtt cggatacggg tggagtttca    1380
aattggtgtg ttatggaatc ccaacttaat cgtgtttagg ggtgggatcc aattgtgtga    1440
tacattacag agcatggttg tggattgttt tctcatatgt tttgattgac ttgcttgata    1500
cattggatga ttcgataagg tgaccggttt acctgggtat ccaaccatca tccgattact    1560
ttttaataat tatttgtttc ttctttatgt tgtctgtctt tttgtttctt gatctataac    1620
attatatttg cccaaatttt cgcattttcc atatgtagct tatatatgta tatatatatt    1680
caataaagta tattgattta gcagatgatt tgtgtatata tttaaatcaa atcaaacatt    1740
aatgatcatt cactagcgtc ttaatcttga aaaattcatc aacggttatc ctttgcagca    1800
tatataaaaa aaattgccaa ccctatgctt ttacacctaa ttcaagggat aacataagtc    1860
gattaaaacg a                                                         1871

<210> SEQ ID NO 17
<211> LENGTH: 1871
<212> TYPE: DNA
<213> ORGANISM: Gossypium Hirsutum
<220> FEATURE:
<221> NAME/KEY: CDS
<222> LOCATION: (1104)..(1331)

<400> SEQUENCE: 17
gggcattcca cacgaccatg tgtcccctat ttccaggcat tttgagactt cacctaaact      60
tctagagttg tttcaaatta gcccctattt gttcttaaat catttttagga tcttgtaaac     120 tcgtatttag gactaaatgt gtaatttata ctttaattat gattgattaa ttgattgatt     180
tngtagtaat gcccgtgacc ctaatccgtt agcgaagagg ggttaggggt tagggggtttt     240 attattattt tttagatatt gtataactct tgttttattt ttaattttgt tactatttca     300
aaggcatttg tttgtagtgt tatttcgagt aggttttatg ggtgaacaac ccttgaccgc     360
caaatcaatc acaagagttc aacattttat ttattttgaa atgtattaaa aatcgttaat     420
ctatatattc gccccattat tgggattaaa tattcacaag ggtttagacc gtcatgagac     480
agattagttt tatcttactg atggtcacat cacaatagta attcaactta atacgagagg     540
aaccattgat tcacgcaatt ggtcatcgca cttagttgaa aagctagggg tgcgaagcta     600
ccgtacgctg gattatgatt gaacacctct aagtcagaat ccgaattaga aacaatgcac     660
gtgtccgttg cctgattgcc aacccccaata cacgtgttg taggtttaac catgtttatg     720
aaagataagg ttttttttt tataagcaag caactatagg ggtttacttc cgtgcgcaaa     780 ttttttaggtt acctatttg ggaggggga ttatgattca agtgaaagaa agttggcaca     840
cacacaatca gtacatctgt tttgacagag acacagccta aaacagcag caaacaagcc     900 taaaggaatc acccaaaaac aacaaccaaa agtacagagg aaaacaaaag aatccctgtt     960
accaccaagc tgaaaaaaag aaaataaaac tcaactttg gcaataaaaa ccctcctacc    1020
ctcaacccct aaccacgcaa caatcagcaa tactccaagc aaccattttc cttacaagtt    1080
```

-continued

```
tgttttctt gtgattaatc cat atg gct agc tcc atg tcc ctt aag ctt gca    1133
                        Met Ala Ser Ser Met Ser Leu Lys Leu Ala
                         1               5                  10 tgt ctg cta gtg ttg tgc atg gtg gtg ggt gca ccc ctg gct caa ggg    1181
Cys Leu Leu Val Leu Cys Met Val Val Gly Ala Pro Leu Ala Gln Gly
             15                  20                  25 gac gta acc cgt gct gat ggc gta gtc acc ctt cca cgc tgc ctt cct    1229
Asp Val Thr Arg Ala Asp Gly Val Val Thr Leu Pro Arg Cys Leu Pro
         30                  35                  40 tta ttg ata ggg aat ggt aat ggt gct gat gct gat gtt gat gcc cca    1277
Leu Leu Ile Gly Asn Gly Asn Gly Ala Asp Ala Asp Val Asp Ala Pro
     45                  50                  55 gct tgc tgc gac atc gtc agg ggt ctc ttg agc tcg ctg ctc tgt ggt    1325
Ala Cys Cys Asp Ile Val Arg Gly Leu Leu Ser Ser Leu Leu Cys Gly
 60                  65                  70 ggt gtt taggaaccga tctagcttga aatcgggttc ggatacgggt ggagtttcaa    1381
Gly Val
 75 attggtgtgt tatggaatcc caacttaatc gtgtttaggg gtgggatcca attgtgtgat    1441 acattacaga gcatggttgt ggattgtttt ctcatatgtt ttgattgact tgcttgatac    1501 attggatgat tcgataaggt gaccggttta cctgggtatc caaccatcat ccgattactt    1561 tttaataatt atttgtttct tctttatgtt gtctgtcttt ttgtttcttg atctataaca    1621 ttatatttgc ccaaatttc gcattttcca tatgtagctt atatatgtat atatatattc    1681 aataaagtat attgatttag cagatgattt gtgtatatat ttaaatcaaa tcaaacatta    1741 atgatcattc actagcgtct taatcttgaa aaattcatca acggttatcc tttgcagcat    1801 atataaaaaa aattgccaac cctatgcttt tacacctaat tcaagggata acataagtcg    1861 attaaaacga                                                          1871

<210> SEQ ID NO 18
<211> LENGTH: 76
<212> TYPE: PRT
<213> ORGANISM: Gossypium Hirsutum

<400> SEQUENCE: 18

Met Ala Ser Ser Met Ser Leu Lys Leu Ala Cys Leu Leu Val Leu Cys
 1               5                  10                  15

Met Val Val Gly Ala Pro Leu Ala Gln Gly Asp Val Thr Arg Ala Asp
             20                  25                  30

Gly Val Thr Leu Pro Arg Cys Leu Pro Leu Leu Ile Gly Asn Gly
         35                  40                  45

Asn Gly Ala Asp Ala Asp Val Asp Ala Pro Ala Cys Cys Asp Ile Val
     50                  55                  60

Arg Gly Leu Leu Ser Ser Leu Leu Cys Gly Gly Val
 65                  70                  75
```